(12) United States Patent
Walker et al.

(10) Patent No.: US 11,554,174 B2
(45) Date of Patent: Jan. 17, 2023

(54) METHODS FOR IMPROVED PROTECTION AND DELIVERY OF AMINOTHIOLS AND ANALOGS THEREOF

(71) Applicant: THE BURLINGTON HC RESEARCH GROUP, INC., Jericho, VT (US)

(72) Inventors: Dale M. Walker, Jericho, VT (US); Vernon E. Walker, Jericho, VT (US); Tsvetelina I. Lazarova, Brookline, MA (US); Steven W. Riesinger, Boston, MA (US)

(73) Assignee: THE BURLINGTON HC RESEARCH GROUP, INC., Jericho, VT (US)

( * ) Notice: Subject to any disclaimer, the term of this patent is extended or adjusted under 35 U.S.C. 154(b) by 11 days.

(21) Appl. No.: 16/988,239

(22) Filed: Aug. 7, 2020

(65) Prior Publication Data
US 2021/0023229 A1    Jan. 28, 2021

Related U.S. Application Data

(62) Division of application No. 15/776,674, filed as application No. PCT/US2016/062526 on Nov. 17, 2016, now Pat. No. 10,780,176.

(Continued)

(51) Int. Cl.
*A61K 31/145* (2006.01)
*A61K 47/60* (2017.01)
(Continued)

(52) U.S. Cl.
CPC ............ *A61K 47/60* (2017.08); *A61K 31/145* (2013.01); *A61P 31/14* (2018.01); *A61P 35/00* (2018.01); *A61P 35/02* (2018.01)

(58) Field of Classification Search
CPC ....... A61K 31/145; A61K 47/60; A61P 31/14; A61P 35/00; A61P 35/02
See application file for complete search history.

(56) References Cited

U.S. PATENT DOCUMENTS

| | | |
|---|---|---|
| 4,399,075 A | 8/1983 | Yoshida et al. |
| 5,846,958 A | 12/1998 | Capizzi et al. |
| (Continued) | | |

FOREIGN PATENT DOCUMENTS

| | | |
|---|---|---|
| JP | 2015-507605 | 3/2015 |
| JP | 2015-516465 | 6/2015 |
| (Continued) | | |

OTHER PUBLICATIONS

PubChem CID 5387490 (Year: 2005).*

(Continued)

*Primary Examiner* — Shengjun Wang
(74) *Attorney, Agent, or Firm* — Troutman Pepper Hamilton Sanders LLP (Rochester)

(57) ABSTRACT

In one aspect, the present application relates to an aminothiol-conjugate of formula (I):

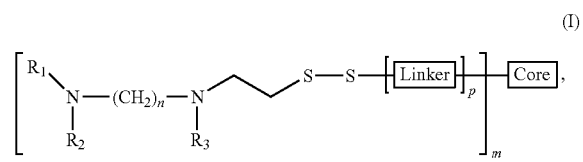

wherein Core, Linker, $R_1$, $R_2$, $R_3$, m, n, and p are as described above. The present invention also relates to a (Continued)

method of treating a subject in need of aminothiol therapy using an aminothiol-conjugate of formula (I).

18 Claims, 5 Drawing Sheets

Related U.S. Application Data

(60) Provisional application No. 62/256,545, filed on Nov. 17, 2015.

(51) Int. Cl.
*A61P 31/14* (2006.01)
*A61P 35/02* (2006.01)
*A61P 35/00* (2006.01)

(56) References Cited

U.S. PATENT DOCUMENTS

| | | | |
|---|---|---|---|
| 9,585,849 B2 | 3/2017 | Walker et al. |
| 9,849,143 B2 | 12/2017 | Walker et al. |
| 10,780,176 B2 | 9/2020 | Walker et al. |
| 2004/0096507 A1 | 5/2004 | Kwang et al. |
| 2009/0239817 A1 | 9/2009 | Walker et al. |
| 2010/0120727 A1 | 5/2010 | Xu |
| 2011/0053894 A1 | 3/2011 | Walker et al. |
| 2013/0040291 A1 | 2/2013 | Walker et al. |
| 2013/0131283 A1 | 5/2013 | Wang et al. |
| 2013/0230490 A1 | 9/2013 | Ho |
| 2013/0244975 A1 | 9/2013 | Baldwin |
| 2013/0337046 A1 | 12/2013 | Walker et al. |
| 2015/0140065 A1 | 5/2015 | Zimmerman et al. |
| 2016/0374967 A1 | 12/2016 | Walker et al. |
| 2017/0028071 A1 | 2/2017 | Walker et al. |
| 2018/0344751 A1 | 12/2018 | Walker et al. |
| 2019/0083630 A1 | 3/2019 | Walker et al. |
| 2020/0093841 A1 | 3/2020 | Walker et al. |

FOREIGN PATENT DOCUMENTS

| | | | |
|---|---|---|---|
| WO | 1999/056755 A1 | 11/1999 |
| WO | 2007/123868 A2 | 11/2007 |
| WO | 2011/046901 A2 | 4/2011 |
| WO | 2011/130331 A2 | 10/2011 |
| WO | 2012/163290 A1 | 12/2012 |
| WO | 2013/188737 A2 | 12/2013 |
| WO | 2015/035260 A1 | 3/2015 |
| WO | 2017/087668 A1 | 5/2017 |

OTHER PUBLICATIONS

Navath et al., "Stimuli-Responsive Star Polyethylene Glycol Conjugates for Improved Intracellular Delivery of N-Acetyl Cysteine in Neuroinflammation," NIH Public Access Author Manuscript. Published in final edited form as: J. Control Release 142(3):447-456 (2010).
International Preliminary Report on Patentability for corresponding PCT/US2016/062526, dated May 31, 2018.
Extended European Search Report for corresponding European Patent Application No. 16867136.0 (dated Apr. 24, 2019).
Ren et al., "Shell-Sheddable Micelles Based on Star-Shaped Poly(ε-caprolactone)-SS-poly(ethyl glycol) Copolymer for Intracellular Drug Release," Soft Matter 7:2329-2331 (2011).
Ma et al., "A Biocompatible Cross-Linked Fluorescent Polymer Prepared via Ring-Opening PEGylation of 4-arm PEG-Amine, Itaconic Anhydride, and an AIE Monomer," Polym. Chem. 6:3634-3640 (2015).
PCT International Search Report and Written Opinion for corresponding PCT/US2016/062526, dated Feb. 3, 2017.
Official Action for corresponding European Patent Application No. 16867136.0, 5 pages (dated May 4, 2020).

Examination Report for corresponding Indian Patent Application No. 201847022228, 6 pages (dated May 1, 2020).
Chen et al., "CCM-AMI, a Polyethylene Glycol Micelle with Amifostine, as an Acute Radiation Syndrome Protectant in C57BL/6 Mice," Health Phys. 109(3):242-248 (2015).
Gupta et al., "Regulation of CD20 Expression by Radiation-Induced Changes in Intracellular Redox Status," Free Radic. Biol. Med. 44(4):614-623 (2008).
Chang et al., "Gold Nanoparticle Extraction Followed by Capillary Electrophoresis to Determine the Total, Free, and Protein-Bound Aminothiols in Plasma," Anal. Chem. 82:2696-2702 (2010).
Buchan et al., "Suppository Formulations as a Potential Treatment for Nephropathic Cystinosis," J. Pharm. Sci. 101(10):3729-38 (2012).
Li et al., "Well-Defined, Reversible Disulfide Cross-Linked Micelles for On-Demand Paclitaxel Delivery," Biomaterials 32:6633-6645 (2011).
Zhan et al., "Acid-Activatable Prodrug Nanogels for Efficient Intracellular Doxorubicin Release," Biomacromolecules 12: 3612-3620 (2011).
Adeli et al., "Synthesis of New Hybrid Nanomaterials: Promising Systems for Cancer Therapy," Nanomedicine: NBM 7:806-817 (2011).
Chen et al., "pH and Reduction Dual-Sensitive Copolymeric Micelles for Intracellular Doxorubicin Delivery," Biomacromolecules 12:3601-3611 (2011).
Edinger & Wagner, "Bioresponsive Polymers for the Delivery of Therapeutic Nucleic Acids," WIREs Nanomed. Nanobiotechnol. 3(1):33-46 (2011).
Cai et al., "Inhibition of Influenza Infection by Glutathione," Free Radical Biol. & Med. 34(7):928-936 (2003).
Notice of Reasons for Rejection and Search Report for corresponding Japan Patent Application No. 2018-545133 (dated Sep. 14, 2020) (English Translation).
File Registry on STN, RN: 1053054-90-2, Entered STN: Sep. 25, 2008.
File Registry on STN, RN: 1052514-77-8, Entered STN: Sep. 25, 2008.
File Registry on STN, RN: 1049697-51-9, Entered STN: Sep. 17, 2008.
First Office Action and Search Report for corresponding China Patent Application No. 201680070616.3 (dated Jul. 29, 2020) (English Translation).
U.S. Appl. No. 17/009,881 to Walker et al. filed Sep. 2, 2020.
Restriction Requirement in U.S. Appl. No. 15/776,674 (dated Feb. 20, 2019).
Office Action in U.S. Appl. No. 15/776,674 (dated Oct. 15, 2019).
Hearing Notice in corresponding Indian Patent Application No. 201847022228, 2 pages (dated May 13, 2021).
Wang et al., "Chelating Complex Micelles for Delivering Cytoprotectant Amifostine and its Application in Radiation Protection," J. Pharmacovigilance 6(3):263-269 (2018).
Yu et al., "The Radioprotective Agent, Amifostine, Suppresses the Reactivity of Intralysomal Iron," Redox Report 8(6):347-355 (2003).
Fatome et al., "Radioprotective Activity of Ethylcellulose Microspheres containing WR 2721, after Oral Administration," Int. J. Radiat. Biol. Relat. Stud. Phys. Chem. Med. 52(1):21-29 (1987).
Fatome et al., "Some Recent Data on Chemical Protection Against Ionizing Radiation," Adv. Space Res. 12(2-3):213-221 (1992).
Mandal et al., "Development of Biodegradable Microcapsules as Carrier for Oral Controlled Delivery of Amifostine," Drug Dev. Ind. Pharm 28(3):339-344 (2002).
Pamujula et al., "Preparation and in vitro Characterization of Amifostine Biodegradable Microcapsules," Eur. J. Pharm Biopharm 57(2):213-218 (2004).
Pamujula et al., "Oral Delivery of Spray Dried PLGA/Amifostine Nanoparticles," J. Pharm. Pharmacol. 56(9):1119-1125 (2004).
Pamujula et al., "Radioprotection in Mice Following Oral Delivery of Amifostine Nanoparticles," Int. J. Radiat. Biol. 81(3):251-257 (2005).
Pamujula et al., "Preparation of Polylactide-Co-Glycolide and Chitosan Hybrid Microcapsules of Amifostine using Coaxial Ultrasonic Atomizer with Solvent Evaporation," J. Pharm. Pharmacol. 60(3):283-289 (2008).

(56) References Cited

OTHER PUBLICATIONS

Praetorius and Mandal, "Alternate Delivery Route for Amifostine as a Radio-/Chemo-Protecting Agent," J. Pharm. Pharmacol. 60(7):809-815 (2008).
Pamujula et al., "Radioprotection in Mice Following Oral Administration of WR-1065/PLGA Nanoparticles," Int. J. Radiat. Biol. 84(11):900-908 (2008).
Lu et al., "Preparation of Amifostine Polylactide-Co-Glycolide Microspheres and its Irradiation Protective to Mouse through Oral Administration," Drug Dev. Ind. Pharm. 37(12):1473-1480 (2011).
Samiei et al., "Ion-Pair Strategy for Enabling Amifostine Oral Absorption: Rat in Situ and in Vivo Experiments," Eur. J. Pharm. Sci. 49(4):499-504 (2013).
Gula et al., "Design and Evaluation of Biodegradable Enteric Microcapsules of Amifostine for Oral Delivery," Int. J. Pharm. 453(2):441-447 (2013).
Yang et al., "Improvement of the in Vitro Safety Profile and Cytoprotective Efficacy of Amifostine Against Chemotherapy by PEGylation Strategy," Biochem. Pharmacol. 108:11-21 (2016).
Wu et al., "Sustained-Release Microspheres of Amifostine for Improved Radio-Protection, Patient Compliance, and Reduced Side Effects," Drug Deliv. 23(9):3704-3711 (2016).
Anselmo and Mitragotri, "Nanoparticles in the Clinic," Bioeng. Transl. Med. 1(1):10-29 (2016).
Ranganathan et al., "Novel Formulation Strategy to Improve the Feasibility of Amifostine Administration," Pharm. Res. 35(5):99 (2018).
Antonadou et al., "Effect of Amifostine on Toxicities Associated with Radiochemotherapy in Patients with Locally Advanced Non-Small-Cell Lung Cancer," Int J. Radiat. Oncol. Biol. Phys. 57:402-408 (2003).
Blasiak et al., "Amifostine Differentially Modulates DNA Damage Evoked by Idarubicin in Normal and Leukemic Cells," Leuk. Res. 26:1093-1096 (2002).
Boccia et al., Assessment and Management of Cutaneous Reactions With Amifostine Administration: Findings of the Ethyol (Amifostine) Cutaneous Treatment Advisory Panel (ECTAP), Int. J. Radiat. Oncol. Biol.Phys. 60(1):302-309 (2004).
Bottcher-Friebertshauser et al., "Activation of Influenza Viruses by Proteases From Host Cells and Bacteria in the Human Airway Epithelium," Pathog. Dis. 69:87-100 (2013).
Booth et al., "Radioprotective Thiolamines WR-1065 and WR-33278 Selectively Denature Nonhistone Nuclear Proteins," Radiat. Res. 153(6):813-822 (2000).
Capizzi RL, "The Preclinical Basis for Broad-Spectrum Selective Cytoprotection of Normal Tissues from Cytotoxic Therapies by Amifostine (Ethyol®)," Eur. J. Cancer 32A(Suppl. 4):S5-S16 (1999).
Clark et al., "Hprt Mutations in Human T-Lymphocytes Reflect Radioprotective Effects of the Aminothiol, WR-1065," Carcinogenesis 17:2647-2653 (1996).
Copp et al., "Radioprotective Efficacy and Toxicity of a New Family of Aminothiol Analogs," Int. J. Radiat. Biol. 89:485-92 (2013).
Dedieu et al., "The Cytoprotective Drug Amifostine Modifies Both Expression and Activity of the Pro-Angiogenic Factor VEGF-A," BMC Med. 8:19 (2010).
Fahey et al., "The Effects of Counter-ion Condensation and Co-ion Depletion Upon the Rates of Chemical Repair of Poly(U) Radicals by Thiols," Int J Radiat Biol 59:885-99 (1991).
Fiorentini et al., "Amifostine (Ethyol) as Modulator of Hepatic and Biliary Toxicity From Intraarterial Hepatic Chemoembolization: Results of a Phase I Study," Hepatogastroenterology 48:313-6 (2001).
Foster-Nora and Siden "Amifostine for Protection From Antineoplastic Drug Toxicity," Am. J. Health. Syst. Pharm. 54:787-800 (1997).
Gaugas JM, "Possible Association of Radioprotective and Chemoprotective Aminophosphorothioate Drug Activity With Polyamine Oxidase Susceptibility," J Natl Cancer Inst 69:329-32 (1982).
Glover et al., "WR-2721 and High-dose Cisplatin: An Active Combination in the Treatment of Metastatic Melanoma," J. Clin. Oncol. 5:574-8 (1987).
Go et al., "Analysis of the Disulfide Bond Arrangement of the HIV-1 Envelope Protein CON-S gp140 ΔCFI Shows Variability in the V1 and V2 Regions," J. Proteome Res. 10(2):578-591 (2011).
Ho et al., "Cystamine Inhibits HIV Type 1 Replication in Cells of Monocyte/Macrophage and T Cell Lineages," AIDS Res Hum Retroviruses. 11(4):451-459 (1995).
Hoffmann et al., "Structure-Activity Analysis of the Lymphocytes," Environ Mol Mutagen 37:117-27 (2001).
Holwitt et al., "Enhancement of Topoisomerase I-Mediated Unwinding of Supercoiled DNA by the Radioprotector WR-33278," Radiat. Res. 124:107-109 (1990).
Kalebic and Schein, "Organic Thiophosphate WR-151327 Suppresses Expression of HIV in Chronically Infected Cells," AIDS Res. Hum. Retroviruses. 10(6):727-733 (1994).
Kataoka et al., "Relationship Between Phosphorylated Histone H2AX Formation and Cell Survival in Human Microvascular Endothelial Cells (HMEC) as a Function of Ionizing Radiation Exposure in the Presence or Absence of Thiol-Containing Drugs," Radiat. Res. 168:106-114 (2007).
Korst et al., "Pharmacokinetics of Amifostine and its Metabolites in the Plasma and Ascites of a Cancer Patient," Cancer Chemother Pharmacol 39:162-166 (1996).
Koseva et al., "Polymer Complex of WR 2721. Synthesis and Radioprotective Efficiency," Eur. J. Pharm. Sci. 65:9-14 (2014).
Koukourakis et al., "Postoperative Pelvic Hypofractionated Accelerated Radiotherapy with Cytoprotection (HypoARC) for High-Risk or Recurrent Prostate Cancer," Anticancer Res. 32:4561-4568 (2012).
Koukourakis et al., "Radical Hypofractionated Accelerated Radiotherapy with Cytoprotection for Invasive Bladder Cancer," Urology 69:245-250 (2007).
Koukourakis et al., "Hypofractionated and Accelerated Radiotherapy with Cytoprotection (HypoARC): a Short, Safe, and Effective Postoperative Regimen for High-Risk Breast Cancer Patients," Int. J. Radiat. Oncol. Biol. Phys. 52:144-155 (2002).
List AF, "Use of Amifostine in Hematologic Malignancies, Myelodysplastic Syndrome, and Acute Leukemia," Semin Oncol 26:61-5 (1999).
Li et al., "Intercapsomeric Disulfide Bonds in Papillomavirus Assembly and Disassembly," J. Virol. 72(3):2160-2167 (1998).
Mangel and San Martin, "Structure, Function and Dynamics in Adenovirus Maturation," Viruses 6:4536-4570 (2014).
Meier and Issels, "Degradation of 2-(3-Aminopropylamino)-ethanethiol (WR-1065) by Cu-Dependent Amine Oxidases and Influence on Glutathione Status of Chinese Hamster Ovary Cells," Biochem Pharmacol 50:489-496 (1995).
Nagvekar, A., "Development and Characterization of Nanoparticle Delivery System for the Radioprotectant Drug Amifostine," Thesis, Creighton University 2008.
Newton et al., "Transport of Aminothiol Radioprotectors Into Mammalian Cells: Passive Diffusion Versus Mediated Uptake," Radiat. Res. 146:206-215 (1996).
Newton et al., "Binding of Radioprotective Thiols and Disulfides in Chinese Hamster V79 Cell Nuclei," Radiat. Res. 146:298-305 (1996).
Nishimura and Yamaya, "A Synthetic Serine Protease Inhibitor, Nafamostat Mesilate, is a Drug Potentially Applicable to the Treatment of Ebola Virus Disease," Tohoku J. Exp. Med. 237:45-50 (2015).
North et al., "Restoration of Wild-Type Conformation and Activity of a Temperature-Sensitive Mutant of p53 (p53 (V272M)) by the Cytoprotective Aminothiol WR1065 in the Esophageal Cancer Cell Line TE-1," Mol. Carcinog. 33(3):181-188 (2002).
Parrott et al., "Role of Conserved Cysteines in the Alphavirus E3 Protein," J. Virol. 83(6):2584-2591 (2009).
Peebles et al., "ROS-Scavenger and Radioprotective Efficacy of the New PrC-210 Aminothiol," Radiat Res 178:57-68 (2012).
Peters et al., Supportive Use of Amifostine in Patients With Head and Neck Tumors Undergoing Radio-chemotherapy. Is it Possible to

(56) References Cited

OTHER PUBLICATIONS

Limit the Duration of the Application of Amifostine? Strahlenther Onkol 175 Suppl 4:23-6 (1999) (abstract only).
Poirier et al., "Antiretroviral Activity of the Aminothiol WR1065 Against Human Immunodeficiency Virus (HIV-1) in Vitro and Simian Immunodeficiency Virus (SIV) Ex Vivo," AIDS Res Ther. 6:24. (2009).
Pluquet et al., "Activation of p53 by the Cytoprotective Aminothiol WR1065: DNA-Damage-Independent Pathway and Redox-dependent Modulation of p53 DNA-binding Activity," Biochem Pharmacol. 65(7):1129-37 (2003).
Rivoire, M. "Cancers of the Colon and the Rectum: News in 1992," Pathol. Biol .(Paris) 40:943-948 (1992) (English Abstract only).
Sagowski et al., "The Radioprotectors Amifostine and Sodium Selenite Do Not Modify the Radiosensitivity of Rat Rhabdomyosarcomas," Onkologie 27:54-7 (2004).
Santini, V., "Amifostine: Chemotherapeutic and Radiotherapetic Protective Effects," Expert Opin Pharmacother 2:479-89 (2001).
Segal et al., "Disulfide Bond Formation During the Folding of Influenza Virus Hemagglutinin," J. Cell Biol. 118(2):227-244 (1992).
Smoluk et al., "Radioprotection of Cells in Culture by WR-2721 and Derivatives: Form of the Drug Responsible for Protection," Cancer Res. 48:3641-3647 (1988).
Sodicoff et al., "Transdermal Absorption of Radioprotectors Using Permeation-Enhancing Vehicles," Radiat. Res. 121:212-9 (1990).
Soref et al., A New Orally Active, Aminothiol Radioprotector-Free of Nausea and Hypotension Side Effects at its Highest Radioprotective Doses, Int. J. Radiat. Oncol. Biol. Phys. 82:e701-707 (2012).
Swain et al., "Assessment of Cell Line Models of Primary Human Cells by Raman Spectral Phenotyping," Biophys J. 98:1703-1711 (2010).
Szczepaniak et al., "Disulfide Bond Formation Contributes to Herpes Simplex Virus Capsid Stability and Retention of Pentons," J. Virol. 85(17):8625-8634 (2011).
Tabachnik et al., "Protein Binding of N-2-Mercaptoethyl-1,3-diaminopropane via Mixed Disulfide Formation After Oral Administration of WR 2721," J. Pharmacol. Exp. Ther. 220(2):243-246 (1982).
Taylor et al., "Amifostine Protects Normal Tissues From Paclitaxel Toxicity While Cytotoxicity Against Tumour Cells is Maintained," Eur. J. Cancer 33:1693-1698 (1997).
Treskes et al., "The Reversal of Cisplatin-Protein Interactions by the Modulating Agent WR2721 and its metabolites WR1065 and WR33278," Cancer Chemother. Pharmacol. 29:467-470 (1992).
Treskes et al., "Effects of the Modulating Agent WR2721 on Myelotoxicity and Antitumour Activity in Carboplatin-Treated Mice," Eur. J. Cancer 30A(2):183-187 (1994).
Treskes et al., "Effects of the Modulating Agent WR2721 and its Main Metabolites on the Formation and Stability of Cisplatin-DNA Adducts in vitro in Comparison to the Effects of Thiosulphate and Diethyldithiocarbamate," Biochem Pharmacol 43:1013-9 (1992).
Yuhas et al., "Treatment of Tumours With the Combination of WR-2721 and cis-Dichlorodiammineplatinum (II) or Cyclophosphamide," Br. J. Cancer 42:574-585. (1980).
Van Laar et al., "Effect of WR-2721 on the Toxicity and Antitumor Activity of the Combination of Carboplatin and 5-Fluorouracil," Cancer Chemother. Pharmacol. 31:97-102. (1992).
Wahid et al., "Disulfide Bonds in Hepatitis C Virus Glycoprotein E1 Control the Assembly and Entry Functions of E2 Glycoprotein," J. Virol. 87(3):1605-1617 (2013).
Walker et al., "WR1065 Mitigates AZT-ddl-Induced Mutagenesis and Inhibits Viral Replication," Environ. Mol. Mutagen. 50(6):460-472 (2009).
Webster et al., "The Adenovirus Protease is Activated by a Virus-Coded Disulphide-Linked Peptide," Cell 72:97-104 (1993).
Whiteside et al., "Properties of Selected S-Nitrosothiols Compared to Nitrosylated WR-1065," Radiation Research 157(5):578-88 (2002).

* cited by examiner

METHODS FOR IMPROVED PROTECTION AND DELIVERY OF AMINOTHIOLS AND ANALOGS THEREOF

This application is a divisional of U.S. patent application Ser. No. 15/776,674, filed May 16, 2018, now U.S. Pat. No. 10,780,176, issued Sep. 22, 2020, which is a national stage application under 35 U.S.C. § 371 of International Application No. PCT/US2016/062526, filed Nov. 17, 2016, which claims priority benefit of U.S. Provisional Patent Application No. 62/256,545, filed Nov. 17, 2015, each of which is hereby incorporated by reference in its entirety.

FIELD OF THE INVENTION

The present invention relates to aminothiol-conjugates, compositions, and methods for making and using them. The conjugates are useful in the treatment of subjects in need of aminothiol therapy (e.g., those in need of treatment with an antiviral agent, a chemoprotectant, a cytoprotectant, a radio-protectant, an anti-fibrotic agent, an anti-tumor agent, an antioxidant, or an antimicrobial or antiparasitic agent).

BACKGROUND OF THE INVENTION

In the current aminothiol drug formulations referred to as the phosphorothioates, protection of the biologically-active aminothiol moiety relies upon conjugation of the aminothiol to a phosphate group. In this formulation, the phosphate group is bound to the sulfhydryl moiety of the aminothiol and it serves the purpose of protecting the active metabolite from adventitious reactivity during the process of drug delivery to target and non-target cells. In the vicinity of cell membranes, the phosphate group is removed by cell membrane-bound alkaline phosphatase. Then the active metabolite (the aminothiol) is taken into the cell by passive diffusion or, under some conditions, active transport by the polyamine transport system.

Delivery of the phosphorothioates to normal cells is successful because many/most non-stressed/non-diseased cells produce alkaline phosphatase that is localized in the cell membrane. However, the same prodrugs are not as effective or are ineffective for the treatment of stressed or diseased cells for several reasons including (i) rapid clearance from circulation, (ii) inability of some cells, and especially stressed or diseased cells, to metabolize the phosphorothioates to their active forms, (iii) vulnerability to metabolism distal to target cells, and (iv) vulnerability to conversion to toxic byproducts (Block et al., "Commentary: the Pharmacological Antioxidant Amifostine—Implications of Recent Research for Integrative Cancer Care," Integr. Cancer Ther. 4:329-351 (2005); Calabro-Jones et al., "The Limits to Radioprotection of Chinese Hamster V79 cells by WR-1065 under Aerobic Conditions," Radiat. Res. 149:550-559 (1998); Meier et al., "Degradation of 2-(3-aminopropylamino)-ethanethiol (WR-1065) by Cu-dependent Amine Oxidases and Influence on Glutathione Status of Chinese Hamster Ovary Cells," Biochem. Pharmacol. 50:489-496 (1995), each of which is hereby incorporated by reference in its entirety). Other limitations include (i) the inability to take advantage of multiple different drug absorption mechanisms, which can differ between diseased versus normal cells and between diseased cells with differing pathologies, (ii) the inability to target cell uptake or transport systems to enhance drug uptake into cells, (iii) the inability to target or exclude specific cell types, (iv) the inability to alter drug circulation or retention times, and (v) the inability to target or exclude specific drug clearance mechanisms. New drug formulations for the aminothiols are needed to overcome these problems and limitations.

The present invention is directed to overcoming these and other deficiencies in the art.

SUMMARY OF THE INVENTION

One aspect of the present invention relates to an aminothiol-conjugate of formula (I):

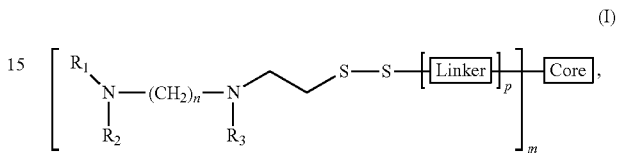

where [Core] is an atom, a molecule, or a macromolecule; [Linker] is a linker group, where the linker group is a polymer, a section of a polymer, an arm of a polymer, an arm of a copolymer, a branch of a dendrimer, or a molecule; $R_1$, $R_2$, and $R_3$ are independently selected from hydrogen and $C_{1-6}$ alkyl;
m is 1 to 100,000;
n is 1 to 10; and
p is 0 to 2500.

Another aspect of the present invention relates to a method of treating a subject in need of aminothiol therapy. The method involves administering to the subject (i) an aminothiol-conjugate of formula (I):

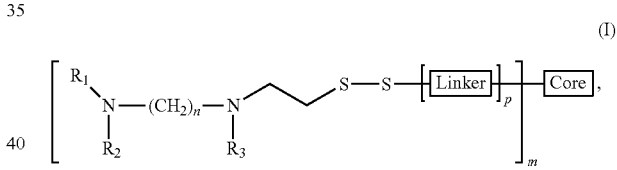

where [Core] is an atom, a molecule, or a macromolecule; [Linker] is a linker group, where the linker group is a polymer, a section of a polymer, an arm of a polymer, an arm of a copolymer, a branch of a dendrimer, an atom, or a molecule; $R_1$, $R_2$, and $R_3$ are independently selected from hydrogen and $C_{1-6}$ alkyl;
m is 1 to 100,000;
n is 1 to 10; and
p is 0 to 2500,
or (ii) a pharmaceutical composition including the aminothiol-conjugate.

The disclosure relates generally to the field of drug delivery that involves the use of polymeric carrier(s) in which a carrier molecule is covalently bound to a molecule of interest. The general purpose of this drug delivery system is to achieve one or more of the following: (i) increased water solubility, (ii) stability against degrading enzymes or reduction of uptake by the reticulo-endothelial system, (iii) targeted delivery of drugs to specific sites. It also relates to reformulating aminothiol drugs for the purpose of protecting one or more active moieties and for enhancing the pharmacokinetics and pharmacodynamics of the reformulated entity for delivery to humans and other animals. As set forth in the Examples below, unexpected drug effects have been shown for the aminothiol-conjugates described herein.

DETAILED DESCRIPTION OF THE INVENTION

The present application relates to improved methods of achieving protection of the active moiety(ies) of phosphorothioate compounds (i.e., aminothiols), delivery of the protected compounds, and activation at desired sites in vivo in humans and animals.

The present application also relates to methods for achieving increased drug efficacy and reduced of toxicity. The present application relates to methods for achieving improved therapeutic efficacy and lower toxicity of aminothiols, their metabolites, analogs thereof, dimers and heterodimers of the aforementioned through use of the aminothiol conjugates described herein. Such protected drugs can be delivered without the use of additional delivery methods or modules, or can be combined with drug delivery systems that achieve intracellular, intracytoplasmic, active or passive targeted cell delivery or exclusion, and/or intra-subcellular organelle delivery.

As used herein, "active moiety" refers to reactive groups such as —SH and/or —NH and the compounds bearing these groups that make up part of the structure of the active metabolites of amifostine, phosphonol, and structurally-related compounds and analogs.

As used herein, "amifostine" refers to the name given to the phosphorothioate form of WR-1065, WR-1065 being the biologically active moiety and physiological metabolite of amifostine.

Figure 1:
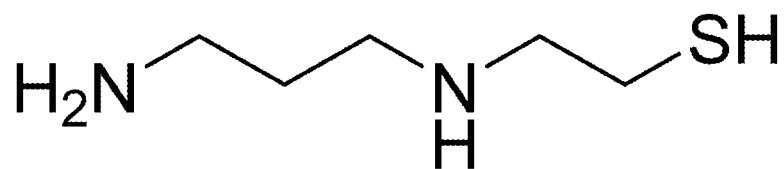
FIG. 1 shows the structure of WR1065, the active moiety of amifostine. The linear formula is $NH_2(CH_2)_3NH(CH_2)_2SH$.
Figure 2:
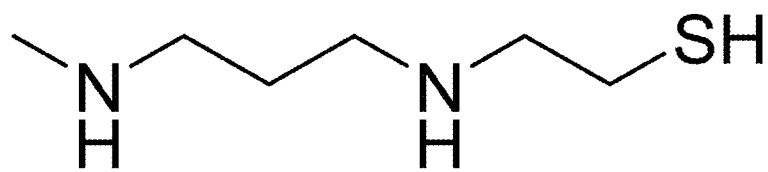
FIG. 2 shows the structure of WR255591, the active moiety of phosphonol. The linear formula is $CH_3NH(CH_2)_3NH(CH_2)_2SH$.
Figure 3A:
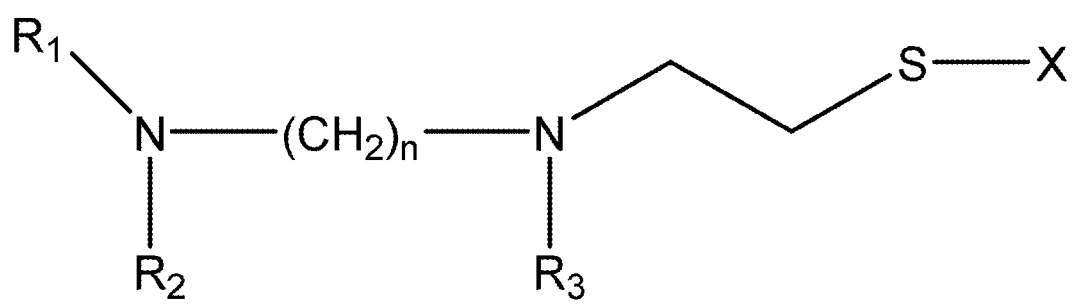
FIGS. 3A-3B shows two generic structures of an aminothiol (and analogues thereof), wherein X is selected from the group consisting of —$PO_3H_2$, hydrogen, sulfhydryl, sulfur, acetyl, isobutyryl, pivaloyl, and benzoyl, wherein each of $R_1$, $R_2$, and $R_3$ is independently selected from hydrogen and $C_{1-6}$ alkyl, wherein n is an integer of from 1 to 10, and (in FIG. 3B) wherein n' is an integer of from 1 to 10. Two exemplary structures of active moieties of the generic aminothiols shown in FIGS. 3A-3B are wherein X is hydrogen.
Figure 3B:
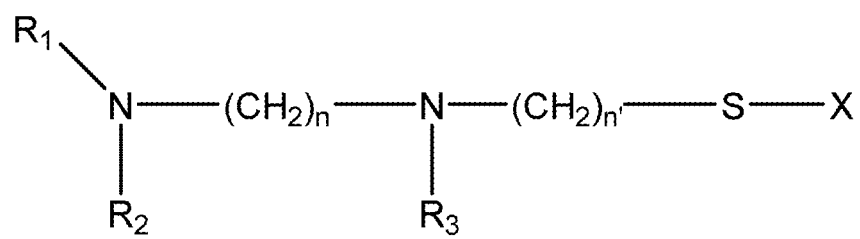

As used herein, "aminothiol" refers to any molecule having the structure shown in FIG. 3.

As used herein, "aminothiol prodrug" refers to a therapeutically inactive prodrug that is composed in part of an aminothiol or aminothiol analog bonded to a conjugate molecule via a bioreducible disulfide bond. Under the appropriate conditions the disulfide bond is reduced, resulting in release of the aminothiol so that its therapeutic benefits can be realized.

As used herein, "bioreducible" or "bioreducible disulfide bond" refers to a bond or disulfide bond that can be reduced by processes, enzymes, reactions, or other mechanisms that are present in vivo, in organ systems, and/or inside of cells.

As used herein, "conjugate" refers to any synthetic or naturally occurring polymer, copolymer, dendrimer, other conjugate, molecule, chemical or combination of the aforementioned that is bound to or conjugated to a therapeutically active aminothiol or aminothiol analog.

As used herein, "dendrimer" refers to any synthetic polymer with a branching, tree-like architecture.

As used herein, "PEG" is the abbreviated form of 'polyethylene glycol'.

As used herein, "phosphonol" is the name given to the phosphorothioate WR-3789, with WR-255591 being the biologically active moiety and metabolite of phosphonol.

As used herein, "phosphorothioate" refers to the general name given to aminothiols that have a phosphate group bound to the sulfhydryl moiety.

As used herein, "polyethylene glycol" (also poly(ethylene glycol); polyethylene oxide) is the name given to molecules with the general structure of H—(O—CH$_2$—CH$_2$)$_n$—OH. Note that PEG (see below) can have alternative groups, such as sulfhydryl moieties, which are not shown in this general formula (see also en.wikipedia.org/wiki/Polyethylene_glycol). Examples of such other alternative groups include —COOH, —OH, and NH$_2$.

Figure 11A:
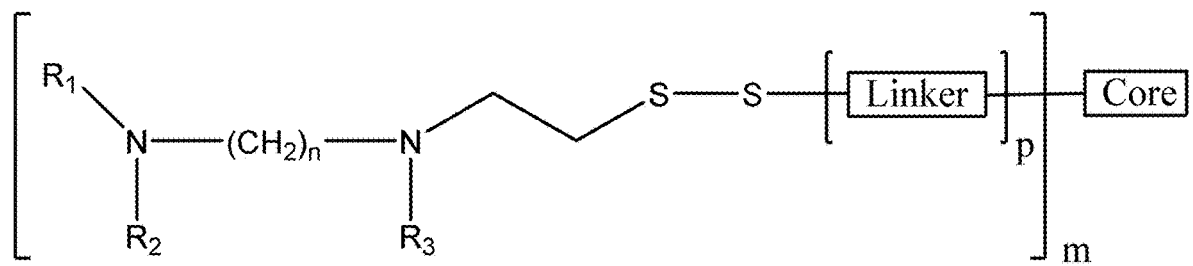
FIGS. 11A-11B show general structures of an aminothiol-conjugate as described herein. Note that the conjugate may include any structure as shown in FIGS. 3 through 10, and can vary with the drug delivery and drug activation conditions and needs of the stress condition or disease for which therapeutic intervention is desired. Also note that two conjugates can be combined; for example folic acid can be linked to a PEG-containing polymer that then is linked to the aminothiol via a disulfide bond. Also contemplated are embodiments in which the length of the carbon chain between the sulfur moiety and the first nitrogen of the aminothiol can vary in length (see FIG. 3B, supra), as shown in FIG. 11B.

As used herein, "prodrug" refers to an inactive drug derivative that is converted to an active form inside of cells and/or the body and preferably at the site of action. One example is the aminothiol-conjugate of formula (I) (see FIG. 11A). Another example is that shown in FIG. 11B.

As used herein, "4SP65" is the abbreviation used to designate the trifluoroactic acid salt of the prodrug composed of WR-1065 conjugated by a disulfide bond to 4-arm star PEG, molecular weight 10,000 Daltons (see SigmaAldrich.com PEG Dendrimers and Multi-arm PEGs, which is hereby incorporated by reference in its entirety).

As used herein, "WR-1065" is the name given to the active moiety of amifostine. It is used here as representative of the active moieties of phosphorothioate drugs.

As used herein, "WR-2721" is a synonym for amifostine.

As described herein, metabolites of phosphorothioates include compounds described as aminothiols, tethered forms of the aminothiols, cysteamine, and cystamine. The aminothiols include, but are not limited to, the active metabolites of the phosphorothioates referred to as amifostine (WR-2721), phosphonol (WR-3689), WR-131527, structurally-related phosphorothioates, analogs of the aminothiols or phosphorothioates, their dephosphorylated active metabolites, and agents as described U.S. Pat. No. 6,489,312 to Stogniew, which is hereby incorporated by reference in its entirety.

The present application also relates to methods for protecting the sulfhydryl moiety of these drugs during the delivery process. For example, the present application relates to the use of polymers or copolymers composed entirely or in part of polyethylene glycol (PEG), other conjugates, or combinations thereof (referred to hence as 'conjugates'). The molecular weight of these conjugates can vary as desired to optimize the drug formulation for a specific purpose, and the polymer can have any shape, including linear, multi-armed (star), or branching, tree-like (as in dendrimers) (Balogh, "Dendrimer 101" *Adv. Exp. Med. Biol.* 620:136-155 (2007); Mintzer et al., "Exploiting Dendrimer Multivalency to Combat Emerging and Re-Emerging Infectious Diseases," *Molecular Pharmaceutics* 9:342-354 (2012), each of which is hereby incorporated by reference in its entirety), or can be of irregular shape. The conjugate also can be selected for its ability to interact with cell surface receptors and/or to enhance compound uptake by a cell-mediated active transport system. The conjugate is bound to the aminothiol through formation of a disulfide bonding to the sulfhydryl moiety of the aminothiol. The disulfide bond is bioreducible in the presence of appropriate intracellular conditions, enzymes, reaction pathways, or combinations thereof.

One aspect of the present invention relates to an aminothiol-conjugate of formula (I):

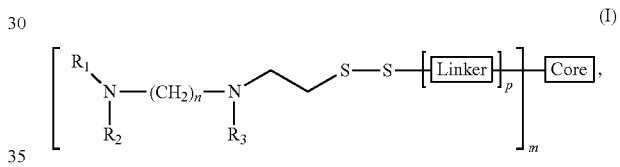

where Core an atom, a molecule, or a macromolecule;

Linker is a linker group, where the linker group is a polymer, a section of a polymer, an arm of a polymer, an arm of a copolymer, a branch of a dendrimer, an atom, or a molecule;

$R_1$, $R_2$, and $R_3$ are independently selected from hydrogen and $C_{1-6}$ alkyl;

m is 1 to 100,000;

n is 1 to 10; and p is 0 to 2500.

Figure 11B:
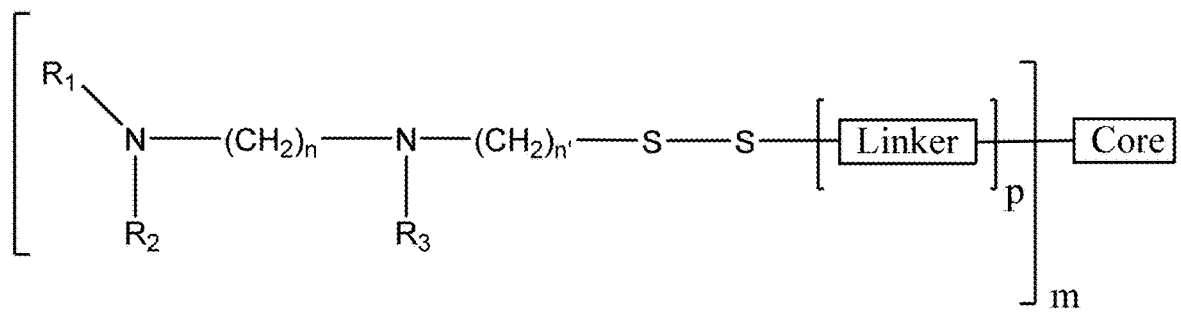

Another aspect of the present invention relates to an aminothiol-conjugate of the Core formula shown in FIG. 11B (formula IV), where Core is an atom, a molecule, or a macromolecule;

Linker is a linker group, where the linker group is a polymer, a section of a polymer, an arm of a polymer, an arm of a copolymer, a branch of a dendrimer, an atom, or a molecule;

$R_1$, $R_2$, and $R_3$ are independently selected from hydrogen and $C_{1-6}$ alkyl;

m is 1 to 100,000;

n is 1 to 10;

n' is 1 to 10; and p is 0 to 2500.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "halo" or "halogen" means fluoro, chloro, bromo, or iodo.

Exemplary aminothiol-conjugates include the following:

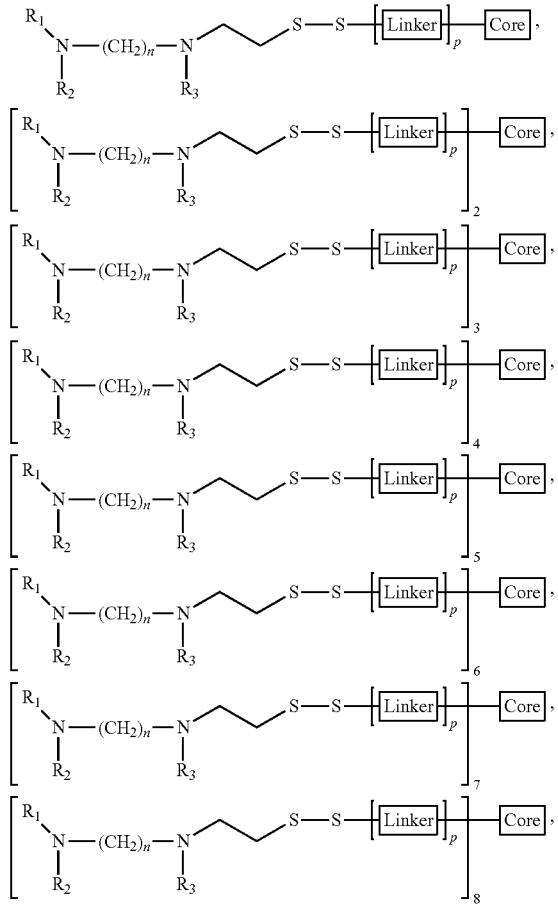

and so on up to

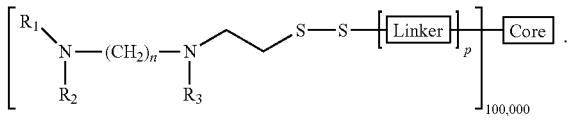

In one embodiment, the molecular weight of the aminothiol-conjugate is 100,000 daltons or less. The molecular weight of the aminothiol-conjugate may be about 100,000 daltons; 20,000 daltons; 10,000 daltons; 5,000 daltons; 3,000 daltons; 2,000 daltons; or 1,000 daltons. In one embodiment, the molecular weight of the aminothiol-conjugate is about 10,000 daltons. In certain embodiments, the molecular weight of the aminothiol-conjugate is about 9,000 to about 11,000 daltons. In certain embodiments, the molecular weight of the aminothiol-conjugate is about 9,000 to about 11,000 daltons.

According to the present invention [Linker] is a linker group, wherein the linker group is a polymer, a section of a polymer, an arm of a polymer, an arm of a copolymer, or a branch of a dendrimer, an atom, or a molecule. In certain embodiments the section of a polymer refers to a repeating unit of a polymer.

Linker may be a moiety with a molecular weight of 100,000 daltons or less; 20,000 daltons or less; 10,000 daltons or less; 5,000 daltons or less; 3,000 daltons or less; 2,000 daltons or less; 1,000 daltons or less; 500 daltons or less; 400 daltons or less; or 200 daltons or less. Linker may be a moiety with a molecular weight of 200 daltons to 100,000 daltons; 200 daltons to 20,000 daltons; 200 daltons to 10,000 daltons; 200 daltons to 5,000 daltons; 200 daltons to 3,000 daltons; 200 daltons to 2,000 daltons; 200 daltons to 1,000 daltons; 200 daltons to 500 daltons; or 200 daltons to 400 daltons. Linker may be a moiety with a molecular weight of 400 daltons to 100,000 daltons; 400 daltons to 20,000 daltons; 400 daltons to 10,000 daltons; 400 daltons to 5,000 daltons; 400 daltons to 3,000 daltons; 400 daltons to 2,000 daltons; 400 daltons to 1,000 daltons; or 400 daltons to 500 daltons. Linker may be a moiety with a molecular weight of 500 daltons to 100,000 daltons; 500 daltons to 20,000 daltons; 500 daltons to 10,000 daltons; 500 daltons to 5,000 daltons; 500 daltons to 3,000 daltons; 500 daltons to 2,000 daltons; or 500 daltons to 1,000 daltons. Linker may be a moiety with a molecular weight of 1,000 daltons to 100,000 daltons; 1,000 daltons to 20,000 daltons; 1,000 daltons to 10,000 daltons; 1,000 daltons to 5,000 daltons; 1,000 daltons to 3,000 daltons; or 1,000 daltons to 2,000 daltons. Linker may be a moiety with a molecular weight of 2,000 daltons to 100,000 daltons; 2,000 daltons to 20,000 daltons; 2,000 daltons to 10,000 daltons; 2,000 daltons to 5,000 daltons; or 2,000 daltons to 3,000 daltons. Linker may be a moiety with a molecular weight of 3,000 daltons to 100,000 daltons; 3,000 daltons to 20,000 daltons; 3,000 daltons to 10,000 daltons; or 3,000 daltons to 5,000 daltons. Linker may be a moiety with a molecular weight of 5,000 daltons to 100,000 daltons; 5,000 daltons to 20,000 daltons; or 5,000 daltons to 10,000 daltons. Linker may be a moiety with a molecular weight of 10,000 daltons to 100,000 daltons; 10,000 daltons to 20,000 daltons. Linker may be a moiety with a molecular weight of 20,000 daltons to 100,000 daltons. Linker may be a moiety with a molecular weight of about 100,000 daltons; 20,000 daltons; 10,000 daltons; 5,000 daltons; 3,000 daltons; 2,000 daltons; 1,000 daltons; 500 daltons; 400 daltons; or 200 daltons.

Polymers as described herein include polyethylene glycol (PEG), branched PEG, polysialic acid (PSA), polysaccharides, pullulane, chitosan, hyaluronic acid, chondroitin sulfate, dermatan sulfate, starch, dextran, carboxymethyl-dextran, polyalkylene oxide (PAO), copolymers of polyalkylene oxides, polyoxamer (such as PLURONIC), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyethylene-co-maleic acid anhydride, polystyrene-co-maleic acid anhydride, poly(l-hydroxymethylethylene hydroxymethylformal) (PHF), and 2-methacryloyloxy-2'-ethyltrimethylammonium phosphate (MPC)), spermine polymer (Zhang and Vinogradov "Short biodegradable polyamine for gene delivery and transfection of brain capillary endothelial cells" *J Control Release* 143:359-366 (2010), which is hereby incorporated by reference in its entirety), and other polymers.

In some embodiments, Linker is selected from the group consisting of polyethylene glycol (polyethylene oxide); thiol-terminated polyethylene glycol (polyethylene oxide); folic acid derivative; a conjugate of folic acid derivative with PEG; spermine; and a polymer of spermine.

Figure 4:
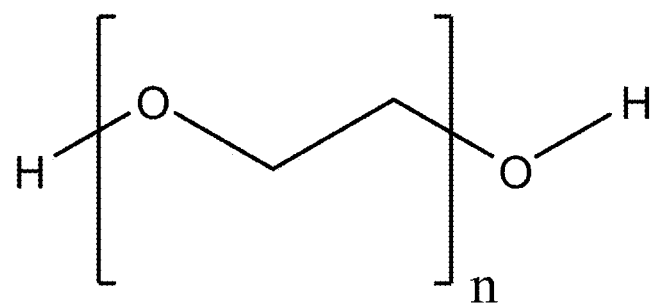
FIG. 4 shows the general structure of polyethylene glycol (polyethylene oxide), wherein 'n' can be any integer from 1 or greater. The linear formula is H—(O—$CH_2$—$CH_2$)$_n$—OH, where in 'n' can be any integer, with a range of 1 to 2500 being most desirable for the applications presented here. Commonly used variants include monomethoxy PEG or dihydroxyl PEG. See, e.g., suitable monomethoxy Poly (ethylene glycol) or dihydroxyl Poly(ethylene glycol) at Sigmaaldrich.com, which is hereby incorporated by reference in its entirety.

In some embodiments, Linker is polyethylene glycol (polyethylene oxide) or polyethylene glycol (polyethylene oxide) derivative (see, e.g., FIG. 4). In one embodiment, Linker is polyethylene glycol (polyethylene oxide), wherein 'n' can be any integer from 1 or greater. The linear formula is H—(O—CH$_2$—CH$_2$)$_n$—OH, where in 'n' can be any integer, with a range of 1 to 2500 being most desirable for the applications presented here. PEG may include a terminal end group, for example, PEG may terminate in a hydroxyl, a thiol, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, or alkoxyamine moieties.

Figure 5A:
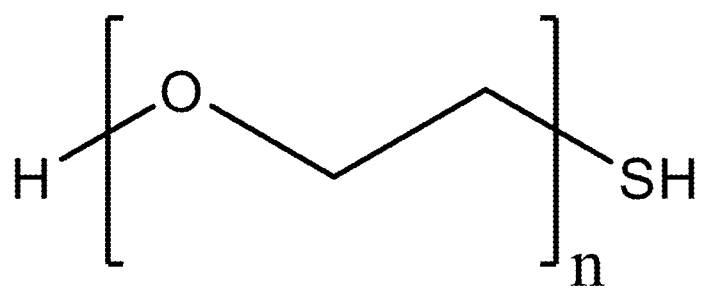
FIGS. 5A-5B show the general structure of thiol-terminated polyethylene glycol (polyethylene oxide) wherein 'n' can be any integer from 1 to 2500. See, e.g., suitable Poly(ethylene glycol) dithiols at Sigmaaldrich.com, Homobifunctional PEGs, which is hereby incorporated by reference in its entirety.
Figure 5B:
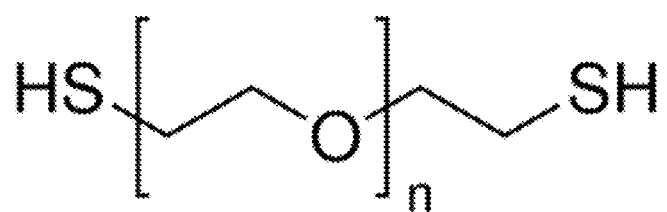

A suitable Linker may also be thiol-terminated polyethylene glycol (polyethylene oxide) wherein 'n' can be any integer from 1 to 2500 (see exemplary structures shown in FIGS. 5A-5B). Exemplary suitable Poly(ethylene glycol) dithiols are described at Sigmaaldrich.com, Homobifunctional PEGs, which is hereby incorporated by reference in its entirety. FIG. 4 shows a general structure of polyethylene glycol (polyethylene oxide), and FIGS. 5A-5B show the general structure of thiol-terminated polyethylene glycol (polyethylene oxide) wherein 'n' can be any integer from 1 to 2500

Figure 9:
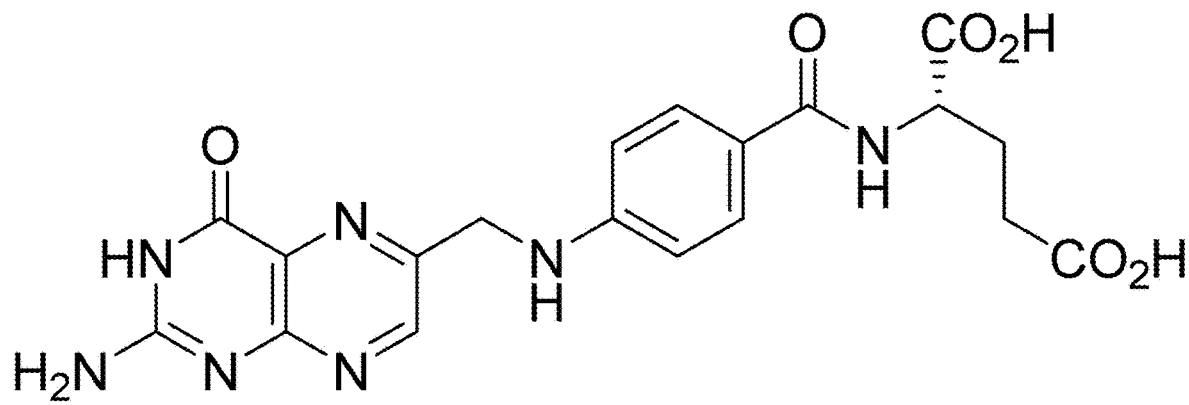
FIG. 9 shows the general structure for folate (folic acid). The linear formula is $C_{19}H_{19}N_7O_6$. By altering the terminal carboxyl group to the appropriate moiety (e.g., SH) and then carrying out the addition of an aminothiol or PEG, respectively, a conjugate of folic acid with an aminothiol or PEG can be synthesized (Chen et al., "Folate-mediated intracellular drug delivery increases the anticancer efficacy of nanoparticulate formulation of arsenic trioxide," Mol Cancer Ther 8(7):1955-63 (2009); Kang et al., "Folic acid-tethered Pep-1 peptide-conjugated liposomal nanocarrier for enhanced intracellular drug delivery to cancer cells: conformational characterization and in vitro cellular uptake evaluation," Int J Nanomed 8:1155-65 (2013), each of which is hereby incorporated by reference in its entirety). The folic acid conjugate offers the advantage that it can interact with the folic acid receptor on the surface of cells and trigger active transport of the prodrug into the cell cytosol.

As noted above, Linker and/or Core may also be a conjugate of folic acid derivative with or without PEG. The general structure for folate (folic acid) is shown in FIG. 9. By altering the terminal carboxyl group to the appropriate moiety (e.g., SH) and then carrying out the addition of an aminothiol or PEG, respectively, a conjugate of folic acid with an aminothiol or PEG can be synthesized (Chen et al., "Folate-mediated intracellular drug delivery increases the anticancer efficacy of nanoparticulate formulation of arsenic trioxide," *Mol Cancer Ther* 8(7):1955-63 (2009); Kang et al., "Folic acid-tethered Pep-1 peptide-conjugated liposomal nanocarrier for enhanced intracellular drug delivery to cancer cells: conformational characterization and in vitro cellular uptake evaluation," *Int Nanomed* 8:1155-65 (2013), each of which is hereby incorporated by reference in its entirety). The folic acid conjugate offers the advantage that it can interact with the folic acid receptor on the surface of cells and trigger active transport of the prodrug into the cell cytosol.

Figure 10:
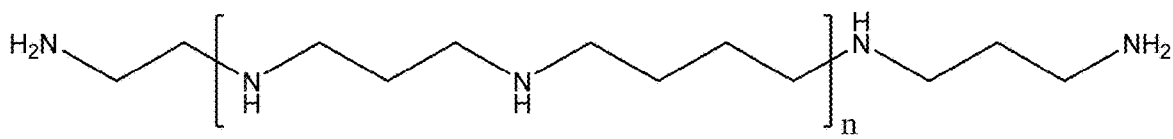
FIG. 10 shows the general structure of spermine polymer. The linear formula is $NH_2C_2H_4(NC_3H_6NHC_4H_8)_n$—$NHC_3H_6NH_2$, wherein 'n' can be any integer equal to or greater than 1. By altering a terminal NH— group to the appropriate moiety (e.g., SH) and then carrying out the addition of an aminothiol or PEG, respectively, a conjugate of spermine with an aminothiol or PEG can be synthesized. The spermine polymer conjugate offers the advantage that it can interact with the polyamine receptor on the surface of cells and trigger active transport of the prodrug into the cell cytosol. (Zhang and Vinogradov, "Short biodegradable polyamine for gene delivery and transfection of brain capillary endothelial cells", J Control Release 143:359-366 (2010) which is hereby incorporated by reference in its entirety)

As noted above, Linker and/or Core may also be spermine or a polymer of spermine. By altering a terminal NH(2) group to the appropriate moiety (e.g., SH) and then carrying out the addition of an aminothiol or PEG, respectively, a conjugate of spermine polymer with an aminothiol or PEG can be synthesized. The general structure of spermine polymer is shown in FIG. 10. The linear formula is NH$_2$C$_2$H$_4$(NC$_3$H$_6$NHC$_4$H$_8$)$_n$—NHC$_3$H$_6$NH$_2$, wherein 'n' can be any integer equal to or greater than 1. The spermine polymer conjugate offers the advantage that it can interact with the polyamine receptor on the surface of cells and trigger active transport of the prodrug into the cell cytosol.

Figure 6:
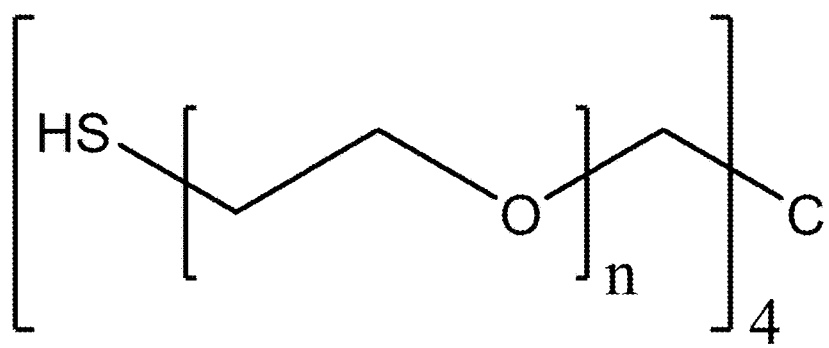
FIG. 6 shows the general structure of 4-arm, thiol-terminated, star polyethylene glycol, wherein 'n' can be any integer, with a range from 1 to 2500 being most desirable for the applications presented here. See, e.g., suitable PEG polymers and dendrimers at Sigmaaldrich.com, PEG Dendrimers and Multi-arm PEGs, which is hereby incorporated by reference in its entirety.
Figure 8:
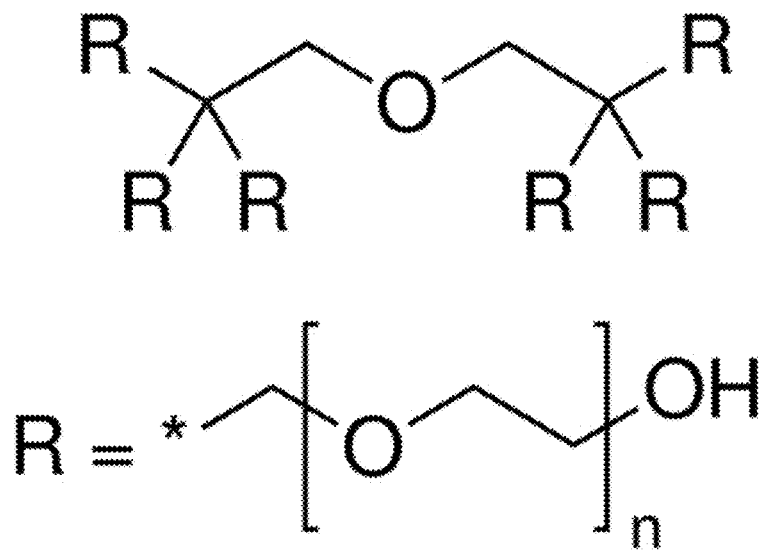
FIG. 8 shows the general structure of 6-arm-PEG. See, e.g., suitable PEG polymers and dendrimers at Sigmaaldrich.com, PEG Dendrimers and Multi-arm PEGs, which is hereby incorporated by reference in its entirety. Note that this general design can be expanded further to create an 8-arm star PEG scaffold, for example.

In certain embodiments, Linker can be attached to the core to form thiol-terminated, polyethylene glycol (see, e.g., FIGS. 6 and 8). In certain embodiments, Linker can be attached to the core to form one arm of a multi-armed thiol-terminated, polyethylene glycol (see, e.g., FIGS. 6 and 8). In certain embodiments, the aminothiol-conjugate is a thiol-terminated, star polyethylene glycol having from 1 to 8 arms. For instance, Linker can be attached to the core to form thiol-terminated 2-arm-PEG, 3-arm-PEG, 4-arm-PEG, 6-arm-PEG, and 8-arm-PEG. See e.g., suitable PEG polymers and dendrimers at Sigmaaldrich.com, PEG Dendrimers and Multi-arm PEGs, which is hereby incorporated by reference in its entirety.

Figure 7:
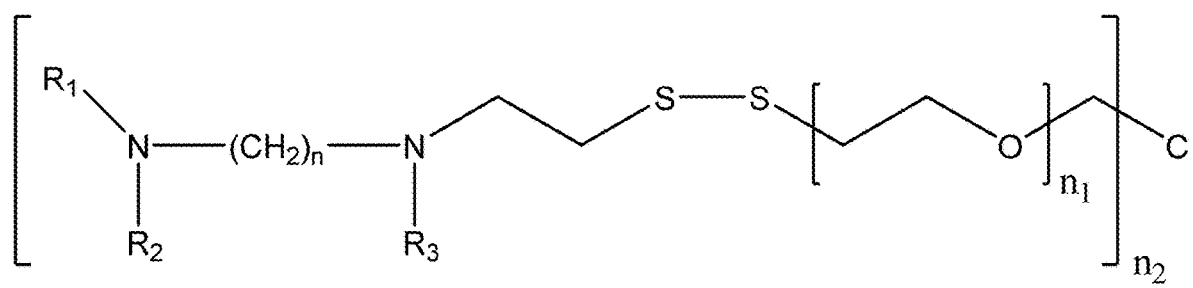
FIG. 7 shows the general structure a thiol-terminated polyethylene glycol conjugated via a disulfide bond to an aminothiol, wherein '$n_1$' can be any integer from 1 to 4 and '$n_2$' can be any integer from 1 to 4. See, e.g., suitable PEG polymers and dendrimers at Sigmaaldrich.com, PEG Dendrimers and Multi-arm PEGs, which is hereby incorporated by reference in its entirety. As described herein, the conjugate according to certain embodiments of the present invention is a 4-arm, thiol-terminated, star polyethylene glycol conjugated via a disulfide bond to an aminothiol and has the structure shown in FIG. 7, where '$n_2$' is 4.

An exemplary structure of a thiol-terminated polyethylene glycol conjugated via a disulfide bond to an aminothiol is shown in FIG. 7, wherein 'n$_1$' can be any integer from 1 to 2500 and 'n$_2$' can be any number of arms that can be accommodated around a core without inducing undesirable steric hindrance or interference. In one embodiment, 'n$_1$' can be any integer from 1 to 2500 and 'n$_2$' can be any integer from 1 to 8. In certain embodiments, the thiol-terminated polyethylene glycol conjugated via a disulfide bond to an aminothiol is shown in FIG. 7, wherein 'n$_1$' can be any integer from 1 to 4 and 'n$_2$' can be any integer from 1 to 4. See, e.g., suitable PEG polymers and dendrimers at Sigmaaldrich.com, PEG Dendrimers and Multi-arm PEGs, which is hereby incorporated by reference in its entirety. In one embodiment, the aminothiol-conjugate is a 4-arm, thiol-terminated, star polyethylene glycol conjugated via a disulfide bond to an aminothiol. In this embodiment, the 4-arm, thiol-terminated, star polyethylene glycol conjugated via a disulfide bond to an aminothiol has the structure shown in FIG. 7, wherein 'n$_2$' is 4.

As described herein, the prodrug described herein is an aminothiol-conjugate. The aminothiol portion of the aminothiol-conjugate of formula I has the following formula:

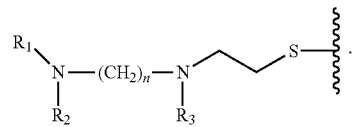

where each R$_1$, R$_2$, and R$_3$ is independently selected from hydrogen and C$_{1-6}$ alkyl, and wherein n is an integer of from 1 to 10. Aminothiols (and analogues thereof) that may be used to synthesize aminothiol-conjugates described herein include those of the exemplary generic structures shown in FIGS. 3A and 3B. For instance, a generic structure of an aminothiol is:

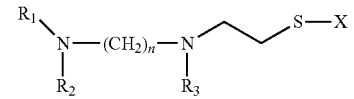

where X is selected from the group consisting of —PO$_3$H$_2$, hydrogen, sulfhydryl, sulfur, acetyl, isobutyryl, pivaloyl, and benzoyl; and each of R$_1$, R$_2$, and R$_3$ is independently selected from hydrogen and C$_{1-6}$ alkyl, and wherein n is an integer of from 1 to 10. Further, two exemplary structures of active moieties of the generic aminothiols shown in FIGS. 3A-3B that may be used to synthesize aminothiol-conjugates described herein are where X is hydrogen. In certain embodiments, the aminothiol is an active moiety of amifostine (NH$_2$(CH$_2$)$_3$NH(CH$_2$)$_2$SH) or phosphonol (CH$_3$NH(CH$_2$)$_3$NH(CH$_2$)$_2$SH).

Another aspect of the present invention relates to the aminothiol-conjugate, wherein [Core] is a polymer core, a dendrimer core, a dendrimer core with an interior dendritic structure (i.e., branches), a therapeutic agent, or a derivative of a therapeutic agent.

In one embodiment, the molecular weight of the Core is 100,000 daltons or less.

Dendrimers have been extensively studied as vehicles for the delivery of therapeutics or as carriers for in vivo imaging (Lee et al., "Designing Dendrimers for Biological Applications," *Nat. Biotech.* 23(12):1517-26 (2005); Esfand & Tomalia, "Poly(amidoamine) (PAMAM) Dendrimers: From Biomimicry to Drug Delivery and Biomedical Applications," *Drug Discov. Today* 6(8):427-36 (2001); Sadler & Tam, "Peptide Dendrimers: Applications and Synthesis," *Rev. Mol. Biotechnol.* 90:195-229 (2002); Cloninger, "Biological Applications of Dendrimers," *Curr. Opin. Chem. Biol.* 6:742-48 (2002); Niederhafner et al., "Peptide Dendrimers," *J. Peptide Sci.* 11:757-88 (2005); Tekade et al., "Dendrimers in Oncology: An Expanding Horizon," *Chem. Rev.* 109(1):49-87 (2009), each of which is hereby incorporated by reference in its entirety). Dendrimers are highly branched macromolecules with well defined three-dimensional architectures (GEORGE R. NEWKOME ET AL., DENDRIMERS AND DENDRONS: CONCEPTS, SYNTHESIS, APPLICATIONS (2001), which is hereby incorporated by reference in its entirety). The appeal of dendrimers lies in their unique perfectly branched architectures, which affords them different properties than corresponding linear polymers of the same composition and molecular weights (Lee et al., "Designing Dendrimers for Biological Applications," *Nat. Biotech.* 23(12):1517-26 (2005), which is hereby incorporated by reference in its entirety). As dendrimers increase in generation, they exponentially increase the number of termini, while only linearly increasing in radius; thus, the termini become more densely packed giving the entire structure a globular shape, where the termini radiate outwards from a central core. Various types of amide dendrimer cores have been described in the art. Suitable cores include those described in Tarallo et al., *Int'l J. Nanomed.* 8:521-34 (2013); Carberry et al., *Chem. Eur. J.* 1813678-85 (2012); Jung et al., *Macromolecules* 44:9075-83 (2011); Ornelas et al., *J. Am. Chem. Soc.* 132:3923-31 (2010); Ornelas et al., *Chem. Commun.* 5710-12 (2009); Goyal et al., *Adv. Synth. Catal.* 350:1816-22 (2008); and Yoon et al., *Org. Lett.* 9:2051-54 (2007), each of which is hereby incorporated by reference in its entirety.

The use of any type of dendrimer is contemplated, including but not limited to poly(amidoamine) (PAMAM) dendrimers such as dense star polymers and Starburst polymers, poly(amidoamine-organosilicon) (PAMAMOS) dendrimers, (Poly (Propylene Imine)) (PPI) dendrimers, tecto dendrimers, multilingual dendrimers, chiral dendrimers, hybrid dendrimers/linear polymers, amphiphilic dendrimers, micellar dendrimers and Fréchet-type dendrimers.

Another aspect of the present invention relates to the aminothiol-conjugate according to claim 1, wherein [Core] is selected from the group consisting of

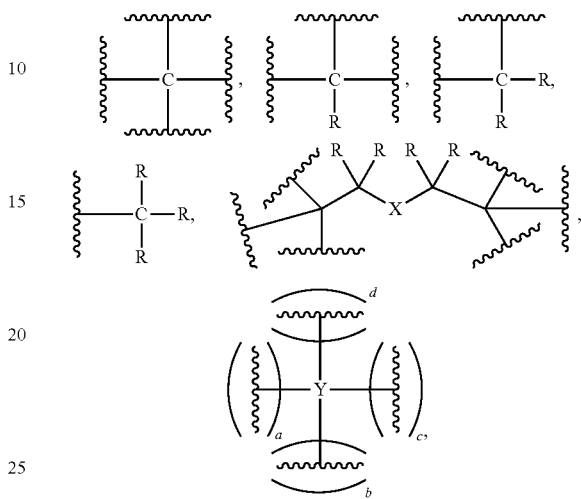

folic acid, folic acid derivative, spermine polymer, and spermine polymer derivative, wherein a is 0 to 2500; b is 0 to 2500; c is 0 to 2500; d is 0 to 2500; R is independently selected from hydrogen, $C_{1-6}$ alkyl, and halogen; X is an atom, a molecule, or a macromolecule; and Y is a multivalent group, molecule, or atom.

Yet another aspect of the present invention relates to the aminothiol-conjugate, wherein X is O, S, $C(R_4)_2$, or $NR_4$, wherein $R_4$ is hydrogen or $C_{1-6}$ alkyl.

A further aspect of the present invention relates to the aminothiol-conjugate having the following structure:

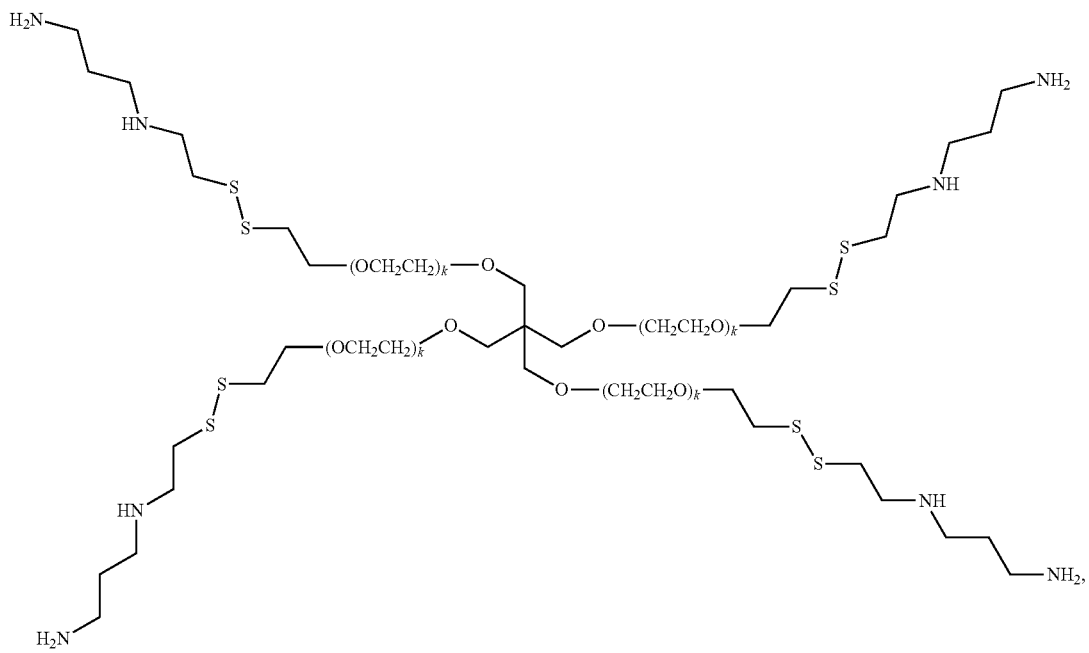

wherein k is 1 to 2500.

Another aspect of the present invention relates to the aminothiol-conjugate according to Formula I, where m is 2 to 100,000.

In one embodiment, the aminothiol conjugate has the following structure:

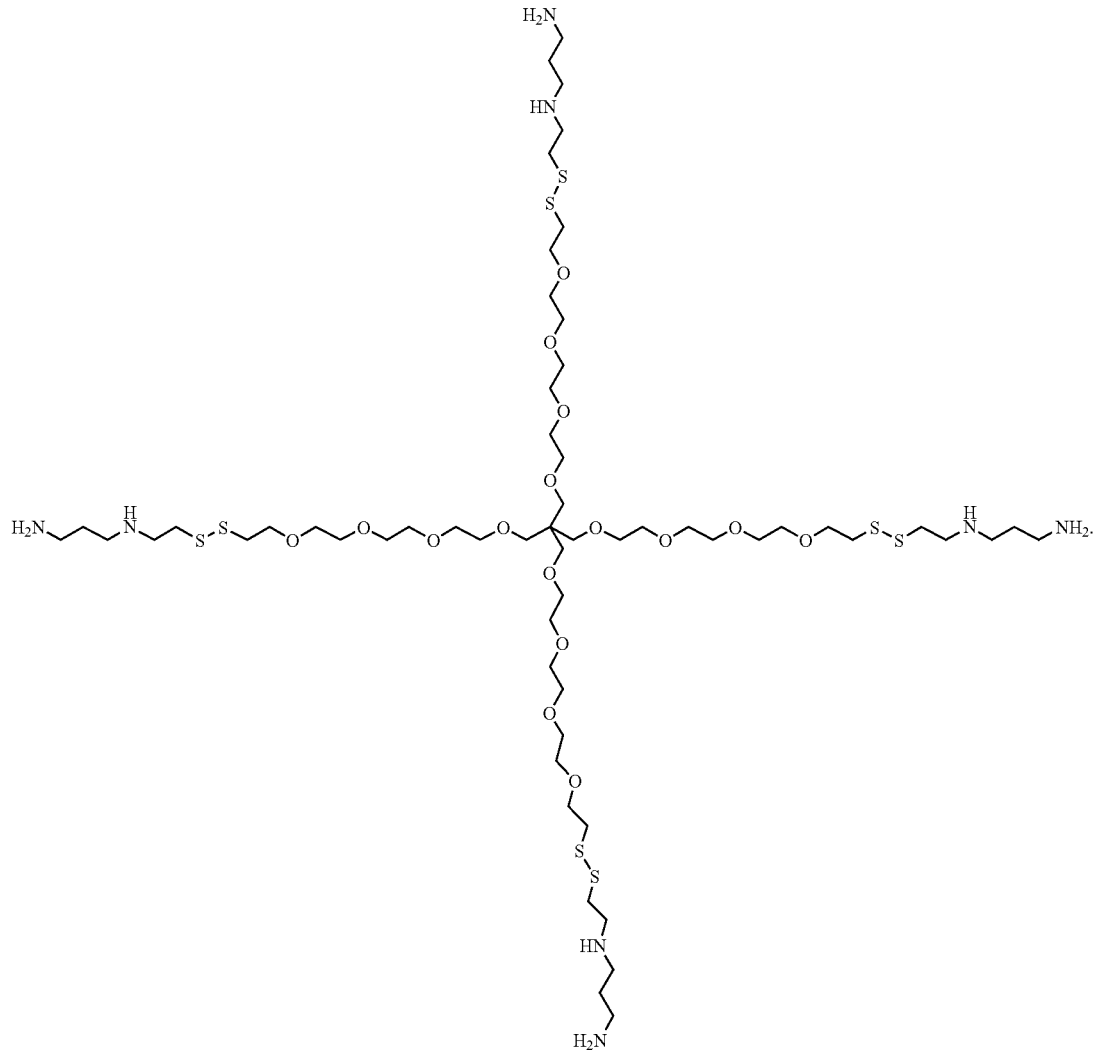 [SMILES: NCCCNCCSSCCOCCOCCOCCOCC(COCCOCCOCCOCCSSCCNCCCN)(COCCOCCOCCOCCSSCCNCCCN)COCCOCCOCCOCCSSCCNCCCN]

In certain embodiments, the aminothiol-conjugate according to the present invention is not a compound of Formula (V) or Formula (VI) below:

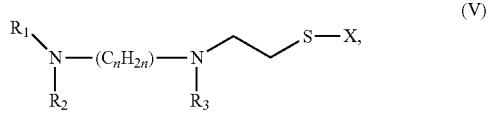

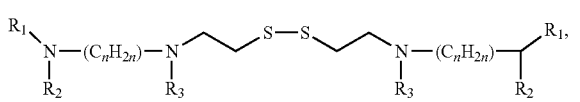

wherein X is selected from the group consisting of —PO$_3$H$_2$, hydrogen, acetyl, isobutyryl, pivaloyl, and benzoyl, wherein each of $R_1$, $R_2$, and $R_3$ is independently selected from the group consisting of hydrogen and $C_{1-6}$ alkyl, wherein n is an integer having a value of from 1 to 10. In one embodiment, the aminothiol-conjugate according to the present invention is not amifostine.

In certain embodiments, the aminothiol-conjugate according to the present invention is not a compound of Formula (V) or Formula (VI), wherein X is an intracellularly-cleavable protecting group selected from the group consisting of a peptide, a sulfur-containing amino acid, glutathione, a sulfur-containing antioxidant, an oxygen-containing antioxidant, a photoreversible thiol tag, and (R)-tert-butyl-2-[(tert-butoxycarbonyl)amino]-3-(trityl sulfanyl)propanoate.

In certain embodiments, the aminothiol-conjugate according to the present invention is not a compound of Formula (V) or Formula (VI), wherein X is the thiol-protected form of the aminothiol selected from the group consisting of a homodimer of the aminothiol, a heterodimer of the aminothiol and a different aminothiol, and cysteamine.

Improved sulfhydryl protecting groups combined with intracellular drug delivery system(s) for the aminothiols, their metabolites, and/or their analogs to cells where therapeutic effects are desired should meet three conditions. First, the protecting group should have the capacity to prevent adventitious reactivity of the aminothiols during drug delivery; second, the protecting group should be removable by systems or processes available in target cells and particularly within the intracellular milieu and/or within lysosomes; and third, the protecting group should be non-toxic to animal and human cells. Other desirable conditions that can be met include (i) increasing drug circulation times, (ii) making the drug amenable to cell absorption via mechanisms that are not applicable to aminothiols alone, (iii) making the drug amenable to intracellular uptake by cell receptor transport systems (the folic acid and polyamine transport systems are two examples) and (iii) altering the mechanisms by which the drug is cleared from circulation and/or the human or animal body.

The aminothiols and their analogs react readily with proteins and nucleic acids, and thus, the active moieties need to be released at or near the sites where reactivity is desired to achieve a therapeutic effect of the drug. Since the therapeutic effects of these drugs have been shown to occur intracellularly as opposed to extracellularly, intracellular delivery represents the optimal delivery site. Intracellular delivery will optimize opportunities for reactivity of the active drug metabolite with target cellular elements as opposed to reaction with targets that are not associated with therapeutic effects, including but not limited to extracellular targets.

Conjugation of a therapeutic aminothiol to another molecule for the purpose of altering the pharmacokinetics and pharmacodynamics from that of the corresponding phosphorothioate is a method that can be used to alter or enhance aminothiol delivery to, and activation in, stressed or diseased cells. Polymers or copolymers, including dendrimers, composed entirely or partially of PEG or comparable biocompatible materials designed to alter and improve drug pharmacokinetics and pharmacodynamics and that also are amenable to cell uptake and intracellular delivery of the aminothiols can be used to meet these goals. Methods are presented below for resolving these problems by using drug formulations that consist of an aminothiol moiety bound to a conjugate as described herein. Such formulations can be used alone or can be combined with additional methods to achieve optimal intracytoplasmic drug delivery and drug efficacy.

Intracellular delivery methods and compositions have been developed by others for effecting intracellular delivery of other drug molecules. Some of those methods and compositions (e.g., those explicitly described or referenced herein) can be used to effect intracellular delivery of aminothiols. However, it is believed that no others have previously proposed to use such compositions and methods in connection with aminothiols. Thus, compositions and methods that have been described by others for protecting the sulfhydryl group of an active pharmaceutical entity can be used to facilitate intracellular delivery of aminothiol compounds, even if those compositions and methods are not among those explicitly described in this disclosure.

Amifostine, as representative of the class of drugs known as phosphorothioates, is an inactive prodrug composed of the therapeutically active aminothiol WR1065 and a phosphate group that is conjugated to the aminothiol via a bond to the aminothiol's sulfhydryl group. This prodrug has specific pharmacokinetic and pharmacodynamics characteristics that make it suitable for delivery to, and activation by, many but not all normal cells (i.e. not stressed or diseased cells) of humans and other animals. However, these characteristics are not suitable for prodrug delivery to, and activation by, most stressed or diseased cells. Thus, in order to realize the therapeutic benefits of the aminothiol, new prodrugs that contain and can release the aminothiol under physiologic conditions of stress and/or disease, and to cells that are stressed or diseased, are needed.

In the following discussion, the terms 'amifostine' and 'WR-1065' (the active moiety of amifostine) will be used as representative examples of all phosphorothioates, aminothiols, their analogs, and the active metabolites of the parent drugs (prodrugs).

Amifostine is a phosphorothioate that is metabolized in vivo to its active moiety WR-1065 (Grdina et al., "Thiol and Disulfide Metabolites of the Radiation Protector and Potential Chemopreventive Agent WR-2721 are Linked to Both its Anti-Cytotoxic and Anti-Mutagenic Mechanisms of Action," *Carcinogenesis* 16:767-774 (1995); Purdie et al., "Interaction of Cultured Mammalian Cells with WR-2721 and its Thiol, WR-1065: Implications for Mechanisms of Radioprotection," *Int. J. Radiat. Biol. Relat. Stud. Phys. Chem. Med.* 43:517-527 (1983); Shaw et al., "Pharmacokinetic Profile of Amifostine," *Semin. Oncol.* 23:18-22 (1996), each of which is hereby incorporated by reference in its entirety). The sulfhydryl moiety of WR1065 is involved in its therapeutic effects (Grdina et al., "Amifostine: Mechanisms of Action Underlying Cytoprotection and Chemoprevention," *Drug Metabol. Drug Interact.* 16:237-279 (2000); Grdina et al., "Differential Activation of Nuclear Transcription Factor Kappab, Gene Expression, and Proteins by Amifostine's Free Thiol in Human Microvascular Endothelial and Glioma Cells," *Semin. Radiat. Oncol.* 12:103-111 (2002); Grdina et al., "Relationships between Cytoprotection and Mutation Prevention by WR-1065," *Mil Med* 167: 51-53 (2002); Grdina et al. "Radioprotectors: Current Status and New Directions," *Radiat. Res.* 163:704-705 (2002), each of which is hereby incorporated by reference in it's entirety), and thus, this moiety requires protection from adventitious reactively during drug delivery and until the drug is taken up into the intracellular environment, and this protection in the case of amifostine, is provided by the phosphate group. The phosphate group is removed when the drug is brought into close proximity to cell plasma membranes and/or the drug is taken up into the plasma membrane. The dephosphorylation step is carried out by membrane-bound alkaline phosphatase, an enzyme that is produced by many, but not all human and animal cells. After removal of the phosphate group, the active moiety is taken up into the intracellular milieu from which it can be distributed further to subcellular organelles or to other cells, and where therapeutic effects are induced. Cellular uptake of many, but not all forms of the aminothiols occurs by passive diffusion, but some drug forms are taken up by active transport through the polyamine transport system, and active transport of other drug forms may occur at some drug concentrations but not others (Grdina et al., "Differential Activation of Nuclear Transcription Factor Kappab, Gene Expression, and Proteins By Amifostine's Free Thiol in Human Microvascular Endothelial and Glioma Cells," *Semin. Radiat. Oncol.* 12:103-111 (2002); Grdina et al., "Relationships between Cytoprotection and Mutation Prevention by WR-1065," *Mil Med* 167: 51-53 (2002); Grdina et al. "Radioprotectors: Current Status and New Directions," *Radiat. Res.* 163:704-705 (2002), each of which is hereby incorporated by reference in its entirety). For cells that cannot take up the drug and/or cannot metabolize the drug, the active form can be delivered to these cells via cell- and tissue-distribution processes. Previously known methods for administering phosphorothioates to a human or animal include, but are not limited to, oral delivery, intraperitoneal injection, subcutaneous injection, intravenous injection, inhalation, incorporation into nanoparticles (Pamujula et al., "Oral Delivery of Spray Dried PLGA/Amifostine Nanoparticles," *J. Pharm. Pharmacol.* 56:1119-1125 (2004); Pamujula et al., "Preparation and In Vitro Characterization of Amifostine Biodegradable Microcapsules," *Eur. J. Pharm. Biopharm.* 57:213-218 (2004); Pamujula et al., "Radioprotection in Mice Following Oral Delivery of Amifostine Nanoparticles," *Int. J. Radiat. Biol.* 81:251-257 (2005), each of which is hereby incorporated by reference in its entirety.), or using other drug delivery systems (Gu et al., "Tailoring Nanocarriers for Intracellular Protein Delivery," *Chem. Soc. Rev.* 40:3638-3655 (2011); Hoffman et al., "The Origins and Evolution of "Controlled" Drug Delivery Systems," *J. of Controlled Release* 132:153-163 (2008); Imbuluzqueta et al., "Novel Bioactive Hydrophobic Gentamicin Carriers for the Treatment of Intracellular Bacterial Infections," *Acta. Biomater.* 7:1599-1608 (2011); Leucuta et al., "Systemic and Biophase Bioavailability and Pharmacokinetics of Nanoparticulate Drug Delivery Systems," *Curr. Drug Del.* 10:208-240 (2013); Patel et al., "Recent Developments in Protein and Peptide Parenteral Delivery Approaches," *Ther. Delivery* 5:337-365 (2014); Patel et al., "Particle Engineering to Enhance or Lessen Particle Uptake by Alveolar Macrophages and to Influence the Therapeutic Outcome," *Eur. J. Pharm. Biopharm.* 89:163-174 (2015); Sakagami, "Systemic Delivery of Biotherapeutics through the Lung: Opportunities and Challenges for Improved Lung Absorption," *Ther. Del.* 4:1511-1525 (2013); Torchilin, "Recent Approaches to Intracellular Delivery of Drugs and DNA and Organelle Targeting," *Ann. Rev. Biomed. Eng.* 8:343-375 (2006), each of which is hereby incorporated by reference in its entirety).

Amifostine is inactive until metabolized by cell membrane-bound alkaline phosphatase, which removes the phosphate group, thereby, releasing WR1065 with its free thiol for uptake into cells (Capizzi, "The Preclinical Basis for Broad-Spectrum Selective Cytoprotection of Normal Tissues from Cytotoxic Therapies by Amifostine (Ethyol)," *Eur. J. Cancer* 32A:Suppl 4: S5-16 (1996); Shaw et al., "Pharmacokinetic Profile of Amifostine," *Semin. Oncol.* 23:18-22 (1996); Yu et al., "The Radioprotective Agent, Amifostine, Suppresses the Reactivity of Intralysosomal Iron," *Redox Report: Communications in Free Radical Research* 8:347-355 (2003), each of which is hereby incorporated by reference in its entirety). Amifostine has little to no activity in diseased or stressed cells because many diseased cells, including pathogen-infected cells, tumor cells, and cells in the microenvironment of metastatic cells, produce little to no membrane-bound enzyme but can and often do produce significant amounts of various alkaline phosphatase isoenzymes (Guerreiro et al., "Distinct Modulation of Alkaline Phosphatase Isoenzymes by 17beta-Estradiol and Xanthohumol in Breast Cancer MCF-7 Cells", *Clin. Biochem.* 40:268-273 (2007); Kato et al., "Effect of Hyperosmolality on Alkaline Phosphatase and Stress-Response Protein 27 of MCF-7 Breast Cancer Cells," *Breast Cancer Res Treat.* 23:241-249 (1992); Van Hoof et al., "Interpretation and Clinical Significance of Alkaline Phosphatase Isoenzyme Patterns," *Crit. Rev. in Clin. Lab. Sci.* 31:197-293 (1994); Walach et al., "Leukocyte Alkaline Phosphatase, CA15-3, CA125, and CEA in Cancer Patients," *Tumori* 84:360-363, each of which is hereby incorporated by reference in its entirety) that are released into the extracellular milieu or circulation so that amifostine bioactivation is remote to target cells. Plasma-membrane bound alkaline phosphatase is a GPI-anchored protein (Marty et al., "Effect of Anti-Alkaline Phosphatase Monoclonal Antibody on B Lymphocyte Function," *Immunol. Lett.* 38:87-95 (1993), which is hereby incorporated by reference in its entirety) that is expressed by some, but not all, cell types. Defects in GPI-anchor synthesis can result from mutations or epigenetic alterations in key genes essential for GPI-anchor synthesis and high rates of mutation induction and epigenetic alterations are common in cancer and have been reported to occur in critical GPI-anchor synthesis genes (Dobo et al., "Defining EMS and ENU Dose-Response Relationships using the Pig-a Mutation Assay in Rats," *Mutat. Res.* 725:13-21 (2011); Dobrovolsky et al., "Detection of In Vivo Mutation in the Hprt and Pig-a Genes of Rat Lymphocytes," *Methods Mol. Biol.* 1044:79-95 (2013), each of which is hereby incorporated by reference in its entirety). Alkaline phosphatase also is present intracellularly in the rough endoplasmic reticulum where it is synthesized, in the Golgi apparatus where additional processing may occur, in Golgi-derived vesicles, in some lysosomes, and around the nuclear envelope (Tokumitsu et al., "Alkaline Phosphatase Biosynthesis in the Endoplasmic Reticulum and its Transport Through the Golgi Apparatus to the Plasma Membrane: Cytochemical Evidence," *J. Histochem. Cytochem.* 31:647-655 (1983), which is hereby incorporated by reference in its entirety). Its localization varies with cell cycle in activated B lymphocytes (Souvannavong et al., "Expression and Visualization During Cell Cycle Progression of Alkaline Phosphatase in B Lymphocytes from C3H/HeJ Mice," *J. Leukocyte Biol.* 55:626-632 (1994), which is hereby incorporated by reference in its entirety), with synthesis occurring around the mitotic phase of the cell cycle (Tokumitsu et al., "Immunocytochemical Demonstration of Intracytoplasmic Alkaline Phosphatase in HeLa TCRC-1 Cells," *J. Histochem. Cytochem.* 29:1080-1087 (1981), which is hereby incorporated by reference in its entirety). Plasma membrane-bound alkaline phosphatase is dependent upon correct microtubule organization to achieve its correct orientation in the cell membrane (Gilbert et al., "Microtubular Organization and its Involvement in the Biogenetic Pathways of Plasma Membrane Proteins in Caco-2 Intestinal Epithelial Cells," *J. Cell. Biol.* 113:275-288 (1991), which is hereby incorporated by reference in its entirety), and microtubule organization can be altered in cancer cells and cells infected with viruses (Nyce, "Drug-Induced DNA Hypermethylation and Drug Resistance in Human Tumors," *Cancer Res.* 49:5829-5836 (1989); Oshimura et al., "Chemically Induced Aneuploidy in Mammalian Cells: Mechanisms and Biological Significance in Cancer," *Environ. Mutagen.* 8:129-159 (1986), which is hereby incorporated by reference in its entirety).

Alkaline phosphatase localization and expression is not uniform across all cell types or across all cell states or conditions, but instead is highly variable. Some cells to which drug delivery is desired do not produce membrane-bound alkaline phosphatase, or produce it only under limited conditions, or only produce it during developmental stages that are of limited duration. In some disease states, such as during inflammation, infection, or neoplastic transformation, membrane-bound alkaline phosphatase expression and localization are altered. Alkaline phosphatase is released into the extracellular milieu during some infectious conditions as a generalized response to pathogens (Murthy et al., "Alkaline Phosphatase Band-10 Fraction as a Possible Surrogate Marker for Human Immunodeficiency Virus Type 1 Infection in Children," *Arch. Path. & Lab. Med.* 118:873-877 (1994), which is hereby incorporated by reference in its entirety). Activated B lymphocytes can shed alkaline phosphatase into the surrounding cellular milieu (Burg et al., "Late Events in B Cell Activation. Expression Of Membrane Alkaline Phosphatase Activity," *J. Immunol.* 142:381-387 (1989), which is hereby incorporated by reference in its entirety) and alkaline phosphatase also is present in serum. Alkaline phosphatase is not expressed in quiescent B lymphocytes; it also is not expressed in active and inactive T-lymphocytes. Release of alkaline phosphatase into the extracellular milieu can result in metabolism of phosphorothioates to their active metabolites at a distance from cell membranes. This phenomenon reduces uptake by cells, increases the availability of metabolites for participation in non-therapeutic reactions, and makes the active moieties available for further metabolism to aldehydes and other compounds with cytotoxic effects.

The active form of amifostine (WR-1065) must be present inside of cells for beneficial effects to be observed. WR-2721 (amifostine), WR-1065, WR-33278, WR-1065-cysteine, and other disulfide forms of the parent compound WR-2721 did not show evidence of activity if present outside of V79 cells (Smoluk et al., "Radioprotection of Cells in Culture by WR-2721 and Derivatives: Form of the Drug Responsible for Protection," *Cancer Res.* 48:3641-3647 (1988), which is hereby incorporated by reference in its entirety). In contrast, intracellular levels of WR-1065 correlated with significant protection against gamma-radiation. Results were similar for HeLa cells, me-180 cells, Ovary 2008 cells, HT-29/SP-1d cells, and Colo 395 tumor cell lines (Smoluk et al., "Radioprotection of Cells in Culture by WR-2721 and Derivatives: Form of the Drug Responsible for Protection," *Cancer Res.* 48:3641-3647 (1988), which is hereby incorporated by reference in its entirety). For optimal cytoprotection, sufficient and sustained intracellular levels of WR-1065, the active form of amifostine, were necessary (Souid et al., "Determination of the Cytoprotective Agent WR-2721 (Amifostine, Ethyol) and its Metabolites in Human Blood using Monobromobimane Fluorescent Labeling and High-Performance Liquid Chromatography," *Cancer Chemother. Pharmacol.* 42:400-406 (1998), which is hereby incorporated by reference in its entirety). If the cells were transferred to drug-free medium for 4 hours before exposure to radiation, the intracellular levels of WR-1065 and WR-33278 decreased markedly along with cytoprotection from radiation damage (Grdina et al., "Thiol and Disulfide Metabolites of the Radiation Protector and Potential Chemopreventive Agent WR-2721 are Linked to Both its Anti-Cytotoxic and Anti-Mutagenic Mechanisms of Action," *Carcinogenesis* 16:767-774 (1995), which is hereby incorporated by reference in its entirety). In vivo tissue levels of WR-1065 were similar in monkeys and in humans and tissue levels of drug were informative for cytoprotective effects (Cassatt et al., "Preclinical Modeling of Improved Amifostine (Ethyol) use in Radiation Therapy," *Semin. Radiat. Oncol.* 12:97-102 (2002); Shaw et al., "Metabolic pathways of WR-2721 (ethyol, amifostine) in the BALB/c mouse," *Drug Metab Dispos.* 22:895-902 (1994), each of which is hereby incorporated by reference in its entirety).

In summary, reliance upon the drug formulations known as the phosphorothioates for delivery of their therapeutically active metabolites, the aminothiols, is associated with several significant problems including (1) inability to metabolize the drug to its active form by some cell types, including but not limited to stressed or diseased cells, (2) inability to activate/metabolize the drug under some physiological or disease conditions, (3) activation of the drug in milieus where its activity is not desired, (4) activation of the drug at a distance from the optimal cellular or subcellular milieu, (5) activation in milieus where the products are vulnerable to metabolism to toxins, and (6) lack of ability to achieve targeted cell delivery or targeted cell exclusion. These problems adversely affect the ability to obtain a therapeutic effect in stressed or diseased cells.

Taken together, these findings support the conclusion that reliance upon a phosphate group for protection of the sulfhydryl moiety of an aminothiol during delivery, and reliance upon alkaline phosphatase for metabolism of the parent drug to its active moiety have significant disadvantages that can affect drug efficacy adversely. The above considerations demonstrate the need for new drug formulations. Methods for achieving these results are described herein.

Three criteria should be satisfied to address the above described problems. Sulfhydryl groups are highly reactive moieties that will form covalent bonds with a variety of moieties present in the bodies and cells of living organisms. Thus, therapeutic drugs that contain one or more sulfhydryl groups that have roles in the pharmacological effects of those drugs require protection of the sulfhydryl moiety during delivery to prevent reactivity with neighboring molecules not related to the drug's desired therapeutic effects. To achieve this protection, any molecular group can be used if it meets the requirements that (i) it achieves the desired protective effect during delivery, (ii) it is amenable to cellular uptake into the cytosol, (iii) it can be removed intracellularly, (iv) it is not toxic to cells (either before or after removal from the active aminothiol moiety), and (v) it achieves intracellular therapeutic aminothiol levels in a time frame that can be achieved given the half-life of the prodrug in circulation (i.e. within an acceptable time frame).

Any method that achieves intracellular drug delivery at therapeutic intracellular levels within an acceptable time frame, including but not limited to delivery into intracellular organelles, will serve the purpose of delivering aminothiol drugs to a milieu where their activity is desired and where they will have a beneficial effect. That is, the observations made in this disclosure relate importantly to realization that intracellular delivery of an intracellularly-cleavable aminothiol-protecting-moiety conjugate beneficially affects administration of aminothiols. The observations made in this disclosure also relate to realization that intracellular delivery-however achieved-of an aminothiol compound having a reactive active moiety is advantageous relative to extracellular delivery of the corresponding phosphorothioate of the aminothiol compound.

Targeted cell delivery and/or targeted cell exclusion is desirable because of the recognized toxicity of aminothiols. For delivery by certain methods, such as oral delivery or inhalation delivery, the delivery method or system should be one that has the capacity to protect the drug from degradation by, and/or reactivity with, enzymes found in the lumen of organs through which the drug will pass. Thus, for oral delivery the methods must achieve protection from luminal enzymes and factors of the gastrointestinal tract, and for inhalation delivery, the methods must protect against degradation by respiratory tract exudates/secretions.

Targeted drug delivery can be either passive or active (Banerjee et al., "Poly(ethylene glycol)-prodrug conjugates: concept, design, and applications," *J Drug Deliv* 2012:1-17 (2012), which is hereby incorporated by reference in its entirety). The enhanced permeability and retention (EPR) effect achieves passive drug targeting by releasing, or causing the accumulation of, drug outside the target site, and it relies upon altered environmental conditions. The EPR effect takes advantage of the hyperpermeable vasculature and reduced lymphatic drainage of tumors and inflamed areas to increase drug accumulation in these areas, thereby, providing passive targeting. Active targeting is based upon taking advantage of potential interactions between a ligand-receptor, antigen-antibody, enzyme substrate (biological pairs). Targeting agents are attached to the surface of the prodrug by conjugation chemistries. Examples of common targeting moieties include peptide ligands, sugar residues, antibodies, or aptamers that have as their biological pair receptors, selectins, antigens, or mRNAs expressed by cells or organs. For example, luteinizing hormone-releasing hormone peptide is used to target receptors overexpressed by several cancer cells. Added groups can be ones that serve as ligands for receptors and/or that trigger receptor-mediated endocytosis.

Finally, to achieve drug activation, any group used to protect the sulfhydryl group of the aminothiol must be one that can be released or removed once the drug has been successfully delivered into the cytoplasm of target and/or non-target cells.

As described herein, the active form of the drug is protected during delivery and it is desirable to obtain release of the aminothiol once delivery has been completed. In general, any compositions or method(s) that provide protection of the sulfhydryl group of the aminothiols during delivery, that result in intracellular release of the active form of the drug following delivery to the desired site(s), and that result in therapeutic intracellular drug levels can be used. Protection of the sulfhydryl moiety of the aminothiols prior to intracellular delivery is essential for obtaining therapeutic benefits of these drugs. Because protection systems should have the characteristic of being able to release the active moiety of the drug once intracytoplasmic delivery has been achieved, systems that address both protection during delivery and release after delivery are discussed together.

For the conjugates described herein, common characteristics include the following. The aminothiol is bound to the conjugate via a bioreducible disulfide bond between the sulfhydryl group of the aminothiol and a sulfhydryl group on the conjugate, or at the end of one or more arms, for multi-arm polymers/copolymers, or at the end of one or more branches, for branching dendrimers. The disulfide bonds are reducible by thiol-disulfide exchange reactions that function primarily in the cytosol and in the cytosolic conditions of target cells, but not extracellularly or in circulation conditions (Navath et al., "Stimuli-Responsive Star Poly(Ethylene Glycol) Drug Conjugates for Improved Intracellular Delivery of the Drug in Neuroinflammation," *J Controlled Release* 142:447-456 (2010), which is hereby incorporated by reference in its entirety). Bonds to sulfhydryl groups that link the aminothiol to the conjugate and that are reducible by cellular processes, reactions, enzymes, or other elements can be used. Reduction of the disulfide bond or other linking bonds results in the release of the aminothiol so that its therapeutic effects can be realized. The conjugate can have a linear, branched or dendrimeric architecture and the molecular weight of the conjugate can vary from low to high, based upon the number of repeating units in the polymer/copolymer and/or the number of branches and repeating units in the dendrimer. Conjugates may or may not have biologic activity.

Conjugates that meet these conditions include the following:

(i) A conjugate that is composed, entirely or in part, of polyethylene oxide (PEG) (Bondar et al., "Lipid-Like Tri-functional Block Copolymers of Ethylene Oxide and Propylene Oxide: Effective and Cytocompatible Modulators of Intracellular Drug Delivery," *Int. J. Pharm.* 461:97-104. (2014); Khorsand et al., "Intracellular Drug Delivery Nanocarriers of Glutathione-Responsive Degradable Block Copolymers Having Pendant Disulfide Linkages," *Biomacromolecules* 14:2103-2111 (2013), each of which is hereby incorporated by reference in its entirety). Other characteristics as described above apply.

(ii) A conjugate composed entirely or in part of folic acid.

(iii) A conjugate composed entirely or in part of spermine or a polymer of spermine.

(iv) A biocompatible moiety that contains a sulfhydryl moiety that can be conjugated via a reducible disulfide bond to the sulfhydryl group of the aminothiol. It should be noted that the number of differing moieties that can be conjugated to the sulfhydryl moiety of an aminothiol and that can meet the above conditions and requirements potentially is very large, and can continue to expand in the future as a result of new research. From this large group, moieties with the following characteristics can serve as protecting groups for conjugation to a therapeutic aminothiol: (a) moieties with a molecular weight of 100,000 daltons or less, (b) moieties composed of biocompatible, non-toxic materials, (c) moieties amenable to cellular uptake at a rate that achieves intracellular levels of aminothiol in the range of 1 micromole or less per $10^6$ cells within the circulating half-life of the prodrug, and (d) moieties that are not amenable to conversion to toxins or that have low toxicity at dose levels that result in therapeutic effects of the aminothiol.

(v) It should be noted that the above listed drug delivery systems can be used in combination with each other. They also can be engineered further to provide targeted cell or tissue type delivery or targeted cell/tissue-type exclusion. In addition, new nanoscopic delivery systems are being developed frequently, and a variety of materials for use in the formation of nanoscopic drug delivery vehicles is expanding rapidly.

Methods for Synthesis of a Prodrug Composed of an Aminothiol or Aminothiol Analog and a PEG Polymer, PEG-Containing Copolymer or a Dendrimer are described below.

In general, the following steps must be completed to bond a conjugate to the sulfhydryl group of an aminothiol or aminothiol analog. First, it is necessary to protect the amine groups of the aminothiol from reactivity; this process is referred to as 'bocing' and can be carried out using a variety of different protecting groups. The one condition that must be met is that the protecting groups must be removable as the last step of the synthesis by mechanisms that do not damage the polymer, copolymer or dendrimer or the aminothiol components of the prodrug. In the second step the sulfhydryl group of the aminothiol is bound to an intermediate via a disulfide bond between the sulfhydryl group of the conjugate and the sulfhydryl group of the aminothiol. In the third step this disulfide is reacted with a polymer, copolymer, or dendrimer. These conjugates must have at least one sulfhydryl group at one end of the molecule (for a linear polymer or copolymer) or at the ends of one or more arms (for a multi-arm polymer or copolymer) or at the end of the branches of a dendrimer. In the last step, the amine protecting groups must be removed using methods that do not damage the structure of the newly synthesized prodrug.

An aminothiol-conjugate of the present invention can be prepared according to Schemes outlined below.

Scheme 1.

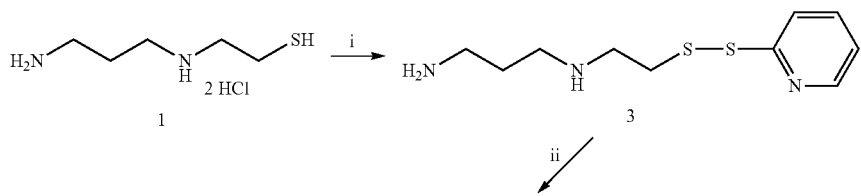

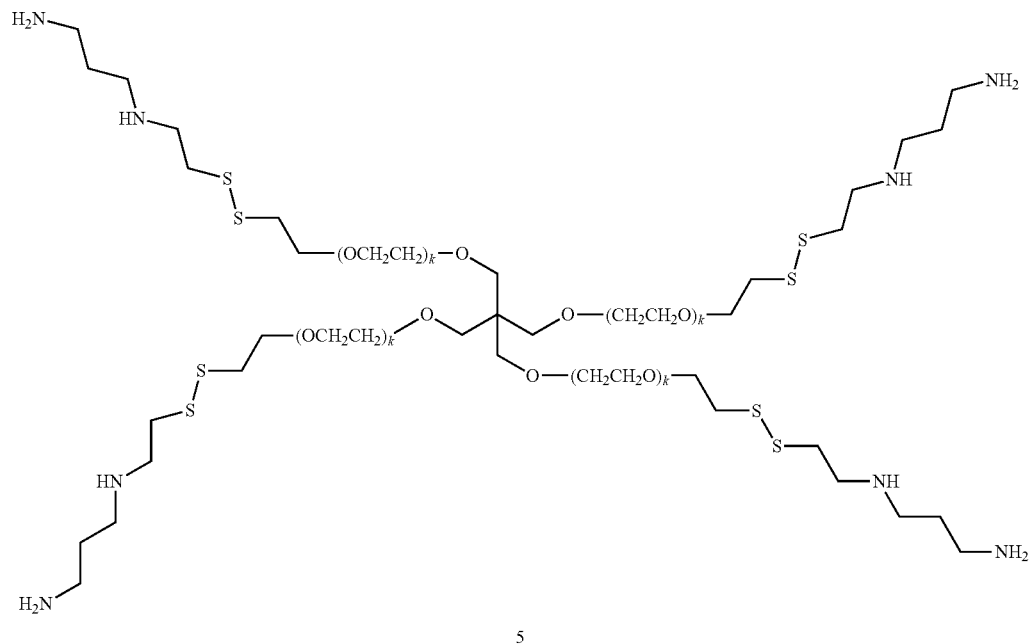

i) Dithiopyridine (TP-TP) (2); ii) 4-arm-PEG-thiol (MW 10 kDal) (4).

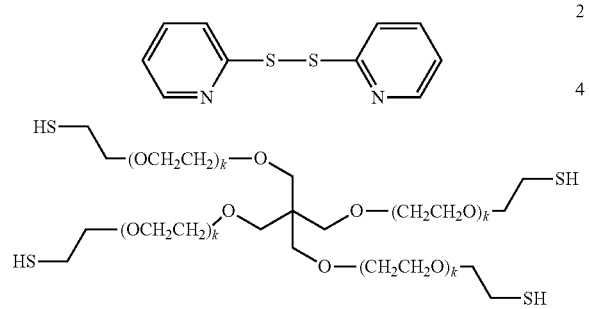

Synthesis of 4-star-PEG-S-S-WR1065 conjugate (5) is shown in Scheme 1. WR1065 dihydrochloride (1) was reacted with dithiopyridine (TP-TP) (2) to form WR1065-S-TP at room temperature. The intermediate (3) was reacted with 4-arm-PEG-thiol (MW 10 kDal) (4) to form the 4-star-PEG-S-S-WR1065 conjugate (5) of Mw 10.536 kDal. The above scheme does not show steps to protect and then deprotect the nitrogens in WR1065 during the synthesis of 4-star-PEG-S-S-WR1065 conjugate (5). The nitrogens on WR1065 (1) had to be protected and in the last step the protecting groups had to be removed (Schemes 2-5).

Scheme 2.

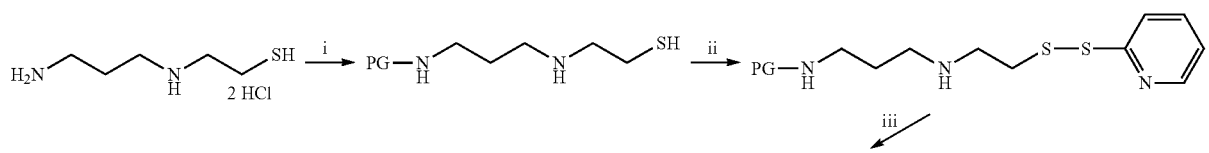

-continued
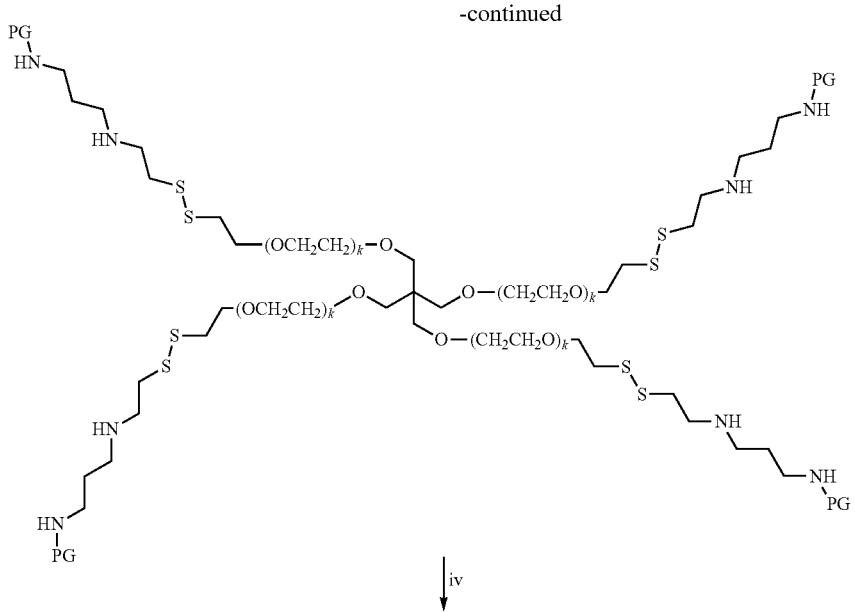
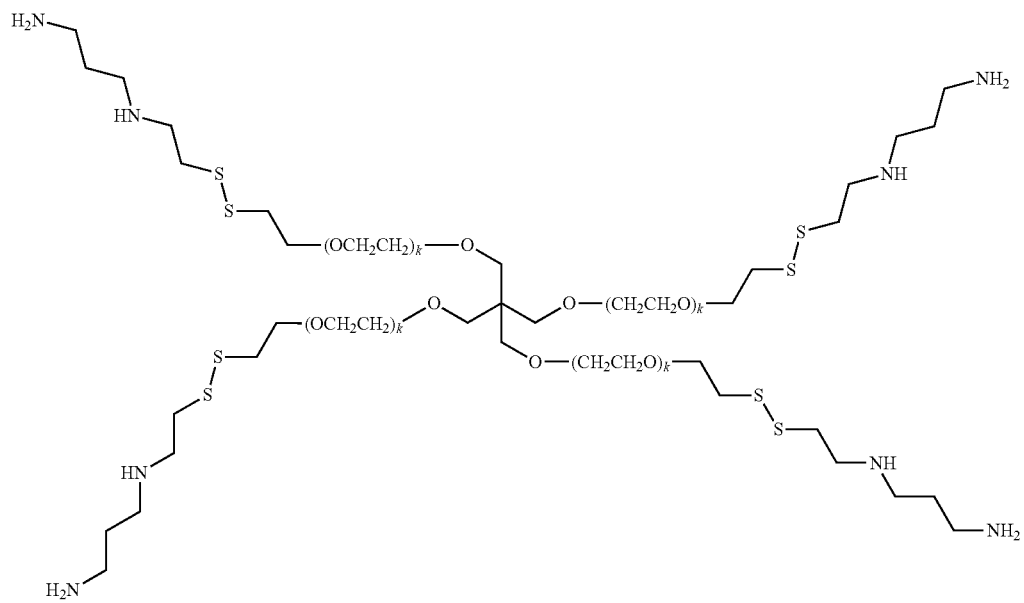
i) introduction of the protecting group (PG); ii) reaction with dithiopyridine (TP-TP) (2); iii) reaction with 4-arm-PEG-thiol (MW 10 kDal) (4); iv) deprotection.
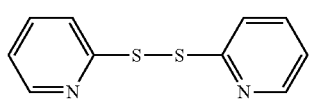
2
-continued
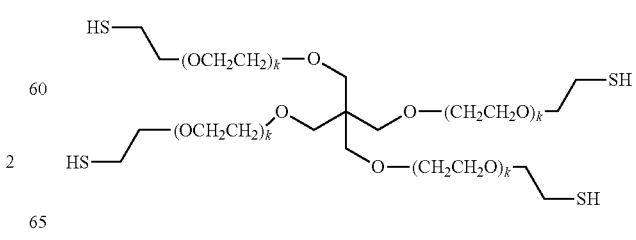
PG is any suitable protecting group.

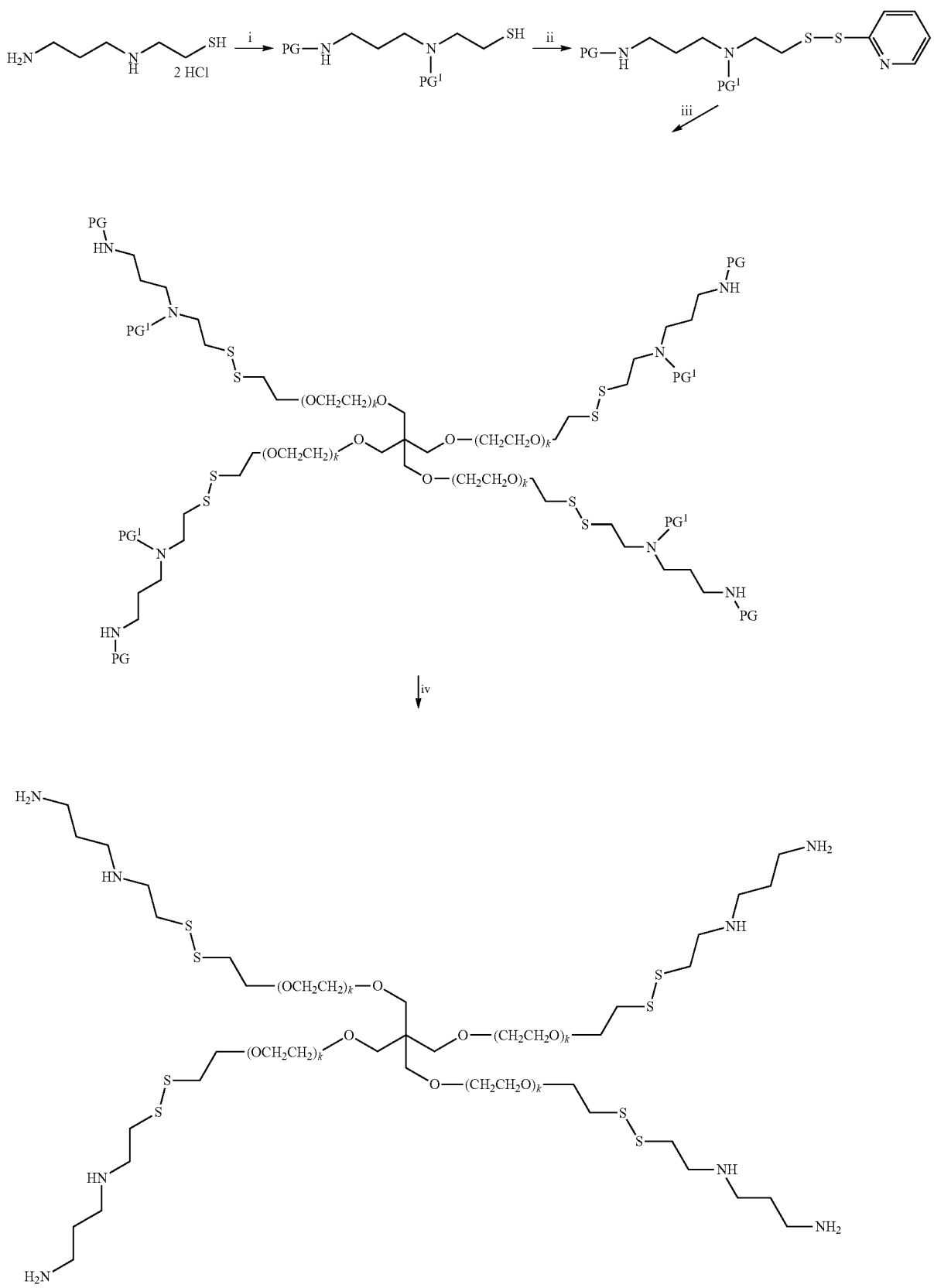
Scheme 3.

i) introduction of the protecting group (PG); ii) reaction with dithiopyridine (TP-TP) (2); iii) reaction with 4-arm-PEG-thiol (Mw 10 kDal) (4); iv) deprotection.
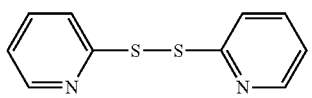
2
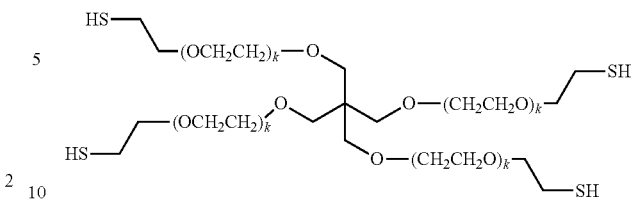
4
PG and PG$^1$ are each a suitable protecting group. PG and PG$^1$ can be the same or different.
Scheme 4.
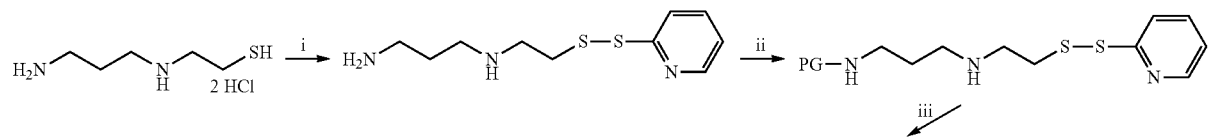
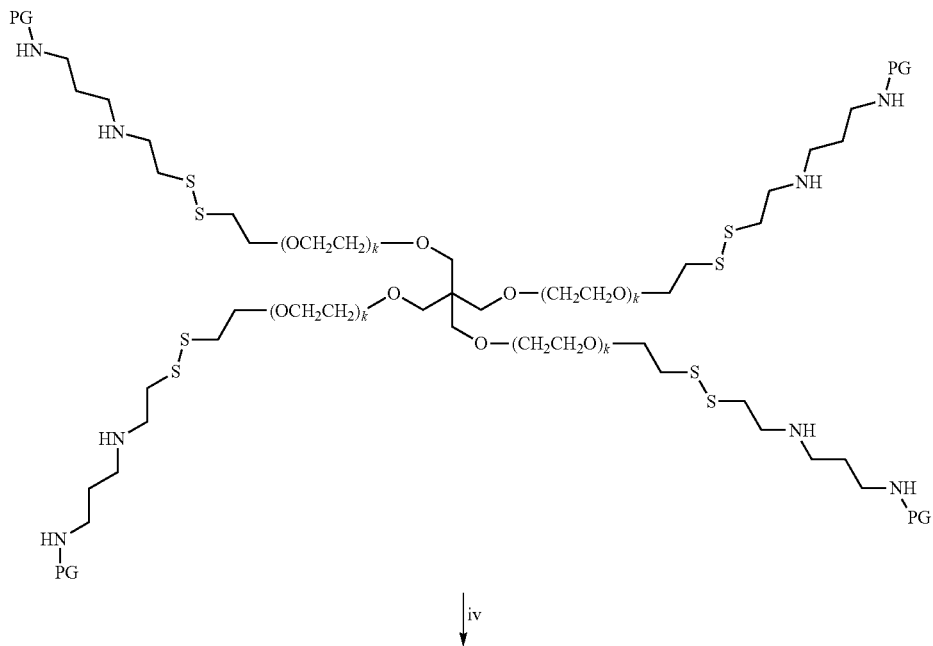

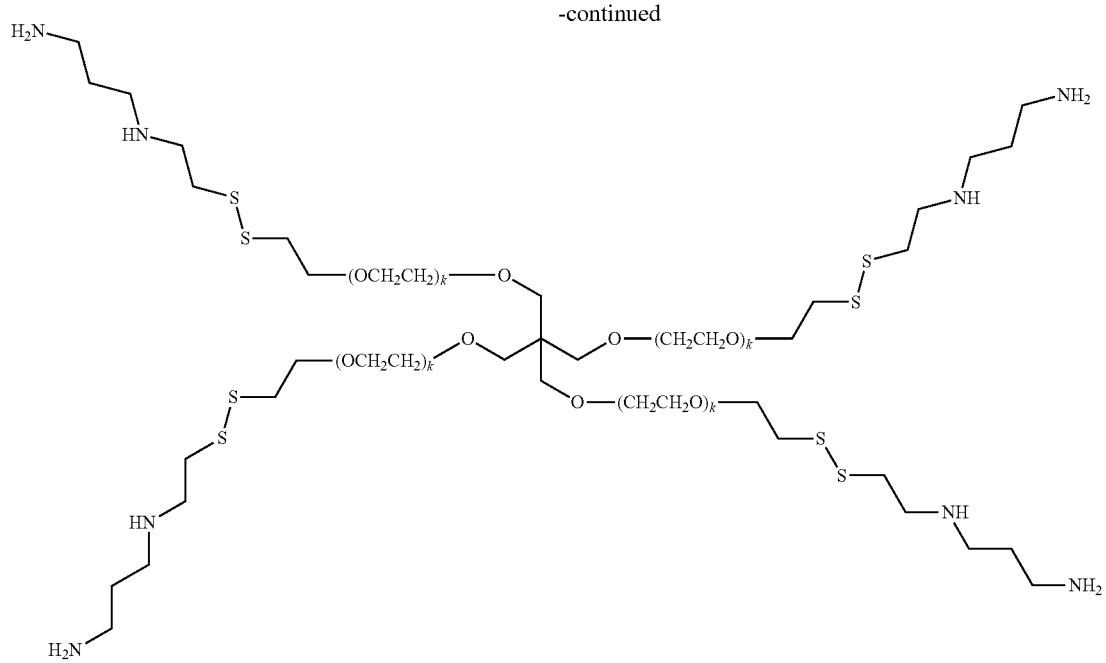
i) introduction of the protecting group (PG) (2); ii) reaction with dithiopyridine (TP-TP); iii) reaction with 4-arm-PEG-thiol (Mw 10 kDal) (4); iv) deprotection.
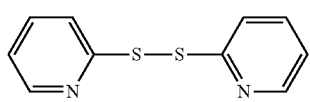
2
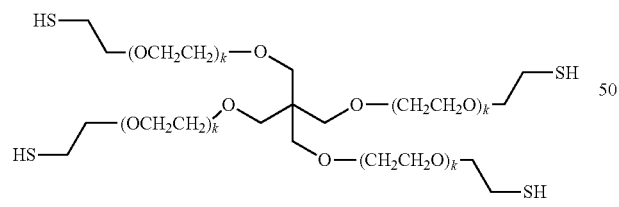
4
PG is any suitable protecting group.
Scheme 5.
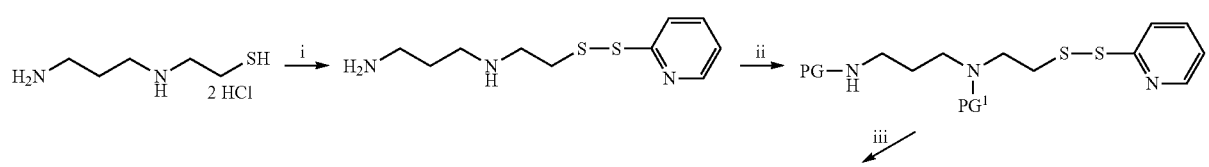

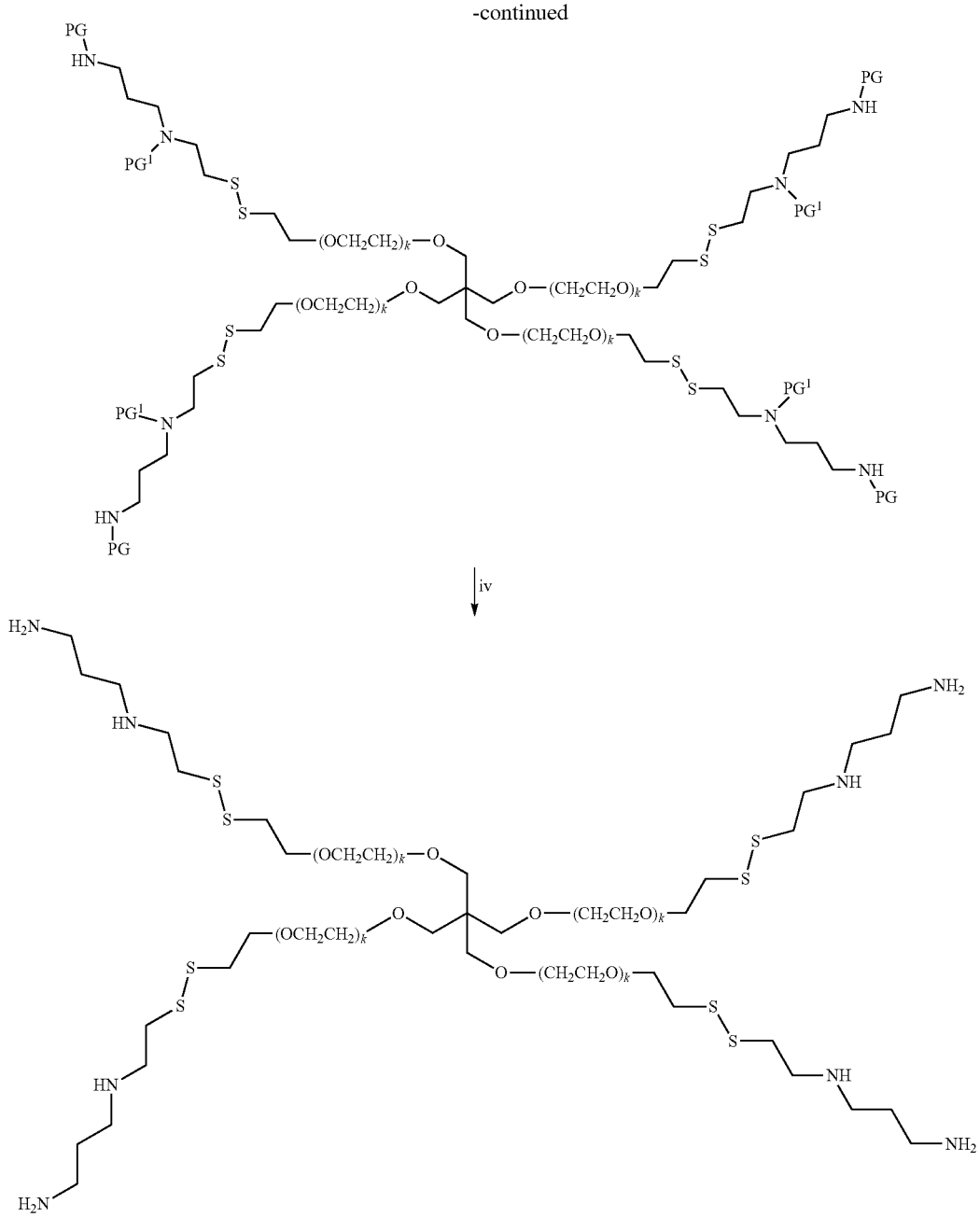
i) introduction of the protecting group (PG) (2); ii) reaction with dithiopyridine (TP-TP); iii) reaction with 4-arm-PEG-thiol (Mw 10 kDal) (4); iv) deprotection.
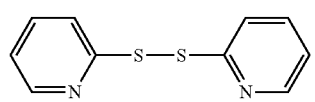
2
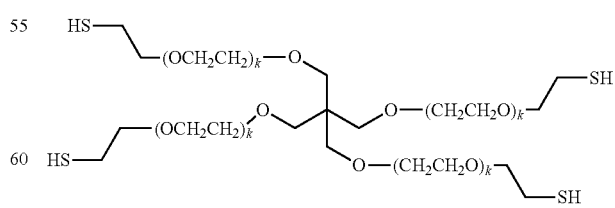
PG and PG¹ are each a suitable protecting group. PG and PG¹ can be the same or different.
Schemes 1-5 describe the synthesis of an exemplary aminothiol-conjugate of formula (I). Synthesis described in Schemes 1-5 can be modified to prepare aminothiol-Core Linker conjugates of formula (I) where [Core], [Linker] $R_1$, $R_2$, $R_3$, m, n, and p are different from the ones exemplified in the schemes above. Accordingly, aminothiol-conjugates of formula (I) can also be prepared using protocols that are modified from the ones described in Scheme 6.

Aminothiol-conjugates of the present invention can be produced according to known methods. For example, aminothiol-conjugates of formula (I) can be prepared according to Scheme 6 outlined below.

Scheme 6.

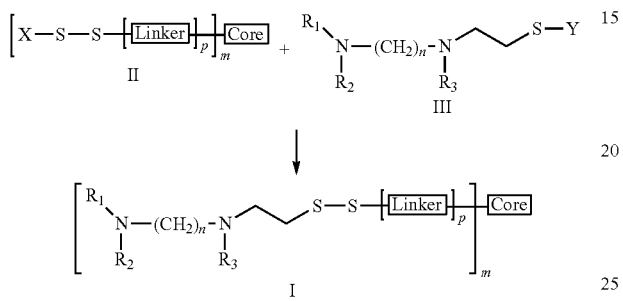

X and Y are each H, a suitable leaving group, or suitable activating group. X and Y can be the same or different.

Reaction of the disulfide (II) with amine compound (III) leads to formation of the aminothiol-conjugate (I). The reaction can be carried out in a variety of solvents, for example in water, buffer, methanol (MeOH), ethanol (EtOH), dimethylformamide (DMF), or other such solvents or in the mixture of such solvents. The reaction can be carried out at a temperature of 0° C. to 100° C., at a temperature of 0° C. to 40° C., or at a temperature of 0° C. to 25° C. During the reaction process, amino groups in the compound of formula III can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (Boc), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Any suitable commercially available disulfide (II) can be used according to the present invention. Alternatively, disulfide (II) can be prepared according to known methods.

The PEG-SH molecule used as a scaffold for conjugation of WR1065 can be a linear PEG polymer of differing length and molecular weight or a multi-arm polymer with differing numbers of arms (e.g., 4 arms as shown above (4) or 6, 8, etc. arms) and molecular weight.

Exemplary aminothiol-conjugates include the following:

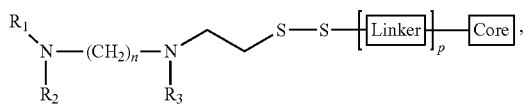

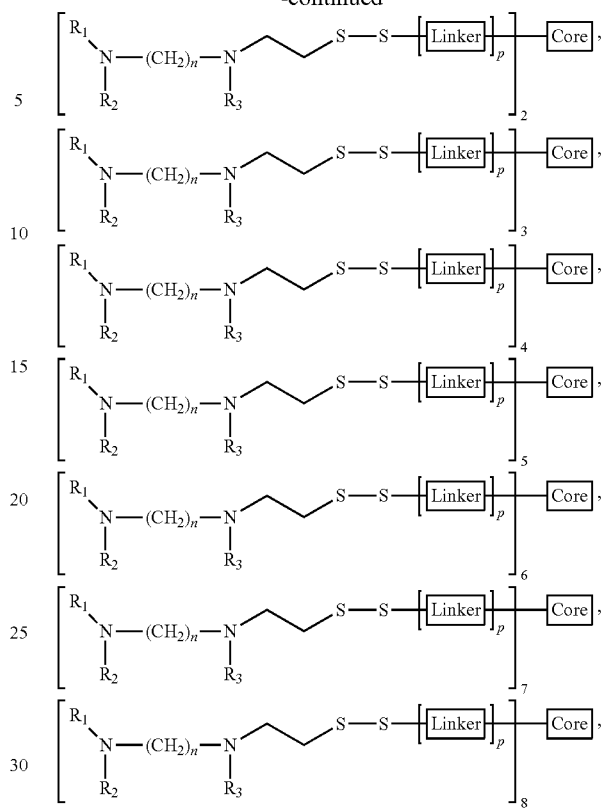

and so on up to

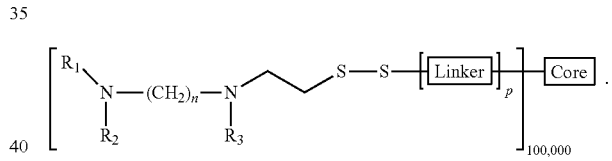

According to the present invention [Linker] is a linker group, wherein the linker group is a polymer, a section of a polymer, an arm of a polymer, an arm of a copolymer, a branch of a dendrimer, an atom, or a molecule. In certain embodiments the section of a polymer refers to a repeating unit of a polymer.

The conjugated prodrug (or active moiety thereof) may be delivered intracellularly or intracytoplasmically to cells (e.g., target cells). In general, any method described in the literature or developed in the future that has characteristics that allow the release of the aminothiol by any biologic or cellular mechanism can be used. Thus, to achieve enhanced drug delivery, the conjugated prodrug can be delivered in combination with other drug delivery modules as presented below. Targeted drug delivery and targeted drug exclusion are desirable but not necessary.

A variety of particulate carriers for intracellular drug delivery have been developed and/or described. Nanoparticles also are referred to as nanovesicles, nanocarriers, or nanocapsules and include lysosomes, micelles, capsules, polymersomes, nanogels, dendritic and macromolecular drug conjugates, and nanosized nucleic acid complexes. A summary of categories into which nanoparticles are sometimes divided includes the following items (1)-(18).

(1) Cell penetrating agents such as amphiphilic polyproline helix P11LRR (such as those described in Li et al., "Cationic Amphiphilic Polyproline Helix P11LRR Targets Intracellular Mitochondria," *J. Controlled Release* 142:259-266 (2010), which is hereby incorporated by reference in its entirety) or peptide-functionalized quantum dots, such as those described in (Liu et al., "Cell-Penetrating Peptide-Functionalized Quantum Dots for Intracellular Delivery," *J. Nanosci. Nanotechnol.* 10:7897-7905 (2010), which is hereby incorporated by reference in its entirety).

(2) Carriers responsive to pH, such as carbonate apatite (Hossain et al., "Carbonate Apatite-Facilitated Intracellularly Delivered siRNA for Efficient Knockdown of Functional Genes," *J. Controlled Release* 147:101-108 (2010), which is hereby incorporated by reference in its entirety).

(3) C2-streptavidin delivery systems, which have been used to facilitate drug delivery to macrophages and T-leukemia cells (such as those described in Fahrer et al., "The C2-Streptavidin Delivery System Promotes the Uptake of Biotinylated Molecules in Macrophages and T-leukemia cells," *Biol. Chem.* 391, 1315-1325 (2010), which is hereby incorporated by reference in its entirety).

(4) CH(3)-TDDS drug delivery systems.

(5) Hydrophobic bioactive carriers (such as those described in Imbuluzqueta et al., "Novel Bioactive Hydrophobic Gentamicin Carriers for the Treatment of Intracellular Bacterial Infections," *Acta. Biomater.* 7:1599-1608 (2011), which is hereby incorporated by reference in its entirety).

(6) Exosomes (such as those described in Lakhal et al., "Intranasal Exosomes for Treatment of Neuroinflammation? Prospects and Limitations," *Mol. Ther.* 19:1754-1756 (2011); Zhang et al., "Newly Developed Strategies for Multifunctional Mitochondria-Targeted Agents In Cancer Therapy," *Drug Discovery Today* 16:140-146 (2011), each of which is hereby incorporated by reference in its entirety).

(7) Lipid-based delivery systems (such as those described in Bildstein et al., "Transmembrane Diffusion of Gemcitabine by a Nanoparticulate Squalenoyl Prodrug: An Original Drug Delivery Pathway," *J. Controlled Release* 147:163-170 (2010); Foged, "siRNA Delivery with Lipid-Based Systems: Promises and Pitfalls," *Curr. Top. Med. Chem.* 12:97-107 (2012); Holpuch et al., "Nanoparticles for Local Drug Delivery to the Oral Mucosa: Proof of Principle Studies," *Pharm. Res.* 27:1224-1236 (2010); Kapoor et al., "Physicochemical Characterization Techniques for Lipid Based Delivery Systems for siRNA," *Int. J. of Pharm.* 427, 35-57 (2012), each of which is hereby incorporated by reference in its entirety), including microtubules, such as those described in (Kolachala et al., "The Use of Lipid Microtubes as a Novel Slow-Release Delivery System for Laryngeal Injection," *The Laryngoscope* 121:1237-1243 (2011), which is hereby incorporated by reference in its entirety).

(8) Liposome or liposome-based delivery systems.

(9) Micelles, including disulfide cross-linked micelles, such as those described in (Li et al., "Delivery of Intracellular-Acting Biologics in Pro-Apoptotic Therapies," *Curr. Pharm. Des.* 17:293-319 (2011), which is hereby incorporated by reference in its entirety). Carriers with disulfide bonds can be formulated so that one or more disulfide bonds link to the aminothiol. A variety of micelles have been described, such as phospholipid-polyaspartamide micelles for pulmonary delivery.

(10) Microparticles, such as those described in (Ateh et al., "The Intracellular Uptake of CD95 Modified Paclitaxel-Loaded Poly(Lactic-Co-Glycolic Acid) Microparticles," *Biomater.* 32:8538-8547 (2011), which is hereby incorporated by reference in its entirety).

(11) Molecular carriers, such as those described in (Hettiarachchi et al., "Toxicology and Drug Delivery by Cucurbit [n]uril Type Molecular Containers," *PloS One* 5:e10514 (2010), which is hereby incorporated by reference in its entirety).

(12) Nanoparticles referred to as 'nanocarriers', such as those described in (Gu et al., "Tailoring Nanocarriers for Intracellular Protein Delivery," *Chem. Soc. Rev.* 40:3638-3655 (2011), which is hereby incorporated by reference in its entirety), some of which have been formulated for delivery of agents to HIV infected cells, such as those described in (Gunaseelan et al., "Surface Modifications of Nanocarriers for Effective Intracellular Delivery of Anti-HIV Drugs," *Adv. Drug Delivery Rev.* 62:518-531 (2010), which is hereby incorporated by reference in its entirety).

(13) Nanoscopic multi-variant carriers.

(14) Nanogels (such as those described in Zhan et al., "Acid-Activatable Prodrug Nanogels for Efficient Intracellular Doxorubicin Release," *Biomacromolecules* 12:3612-3620 (2011) and Zhang et al., "Folate-Mediated poly(3-hydroxybutyrate-co-3-hydroxyoctanoate) Nanoparticles for Targeting Drug Delivery," *Eur. J. Pharm. Biopharm.* 76:10-16 (2010), each of which is hereby incorporated by reference in its entirety).

(15) Hybrid nanocarrier systems, which consist of components of two or more particulate delivery systems (such as those described in Pittella et al., "Enhanced Endosomal Escape of siRNA-Incorporating Hybrid Nanoparticles from Calcium Phosphate and PEG-Block Charge-Conversional Polymer for Efficient Gene Knockdown With Negligible Cytotoxicity," *Biomater.* 32:3106-3114 (2011), which is hereby incorporated by reference in its entirety). Copolymeric micelle nanocarrier (such as those described in Chen et al., "pH and Reduction Dual-Sensitive Copolymeric Micelles for Intracellular Doxorubicin Delivery," *Biomacromolecules* 12:3601-3611 (2011), which is hereby incorporated by reference in its entirety); liposomal nanocarriers, (such as those described in (Kang et al., "Design of a Pep-1 Peptide-Modified Liposomal Nanocarrier System for Intracellular Drug Delivery: Conformational Characterization and Cellular Uptake Evaluation," *J. of Drug Targeting* 19:497-505 (2011), which is hereby incorporated by reference in its entirety).

(16) Nanoparticles can be constructed with a variety of nanomaterials (such as those described in Adeli et al., "Synthesis of New Hybrid Nanomaterials: Promising Systems for Cancer Therapy," *Nanomed. Nanotechnol. Biol. Med.* 7:806-817 (2011); Al-Jamal et al., "Enhanced Cellular Internalization and Gene Silencing with a Series of Cationic Dendron-Multiwalled Carbon Nanotube:siRNA Complexes," *FASEB J* 24:4354-4365 (2010); Bulut et al., "Slow Release and Delivery of Antisense Oligonucleotide Drug by Self-Assembled Peptide Amphiphile Nanofibers," *Biomacromolecules* 12:3007-3014 (2011), each of which is hereby incorporated by reference in its entirety).

(17) Peptide-based drug delivery systems, which include a variety of cell penetrating peptides and including (but not limited to) TAT-based delivery systems (such as those described in Johnson et al., "Therapeutic Applications of Cell-Penetrating Peptides," *Methods Mol. Biol.* 683:535-551 (2011), which is hereby incorporated by reference in its entirety).

(18) Polymers or copolymer-based delivery systems, such as those described in (Edinger et al., "Bioresponsive Polymers for the Delivery of Therapeutic Nucleic Acids," *Wiley*

*Interdisc. Rev. Nanomed. and Nanobiotechnol.* 3:33-46 (2011), which is hereby incorporated by reference in its entirety).

Additional intracellular drug delivery systems that may be considered to fall into the category of nanoparticles include the following items (a)-(u).

(a) Aptamers (such as those described in Orava et al., "Delivering Cargoes into Cancer Cells Using DNA Aptamers Targeting Internalized Surface Portals," *Biochim. Biophys. Acta.* 1798:2190-2200 (2010), which is hereby incorporated by reference in its entirety).

(b) Bacterial drug delivery systems (such as those described in Pontes et al., "*Lactococcus Lactis* as a Live Vector: Heterologous Protein Production and DNA Delivery Systems," *Protein Expression Purif.* 79:165-175 (2011), which is hereby incorporated by reference in its entirety).

(c) Protein-based, self-assembling intracellular bacterial organelles (bacterial shells) (such as those described in Corchero et al., "Self-Assembling, Protein-Based Intracellular Bacterial Organelles: Emerging Vehicles for Encapsulating, Targeting And Delivering Therapeutical Cargoes," *Microb. Cell Factories* 10:92 (2011), which is hereby incorporated by reference in its entirety).

(d) Blended systems (such as those described in Lee et al., "Lipo-Oligoarginines as Effective Delivery Vectors to Promote Cellular Uptake," *Mol. Biosyst.* 6:2049-2055 (2010), which is hereby incorporated by reference in its entirety).

(e) Covalently modified proteins (such as those described in Muller, "Oral Delivery of Protein Drugs: Driver for Personalized Medicine," *Curr. Molec. Bio.* 13:13-24 (2011), which is hereby incorporated by reference in its entirety).

(f) Drug-loaded irradiated tumor cells (such as those described in Kim, et al., "Delivery of Chemotherapeutic Agents Using Drug-Loaded Irradiated Tumor Cells to Treat Murine Ovarian Tumors," *J. Biomed. Sci.* 17:61 (2010), which is hereby incorporated by reference in its entirety).

(g) Dual loading using micellplexes (such as those described in Yu et al., "Overcoming Endosomal Barrier by Amphotericin B-Loaded Dual pH-Responsive PDMA-b-PDPA Micelleplexes for siRNA Delivery," *ACS Nano* 5:9246-9255 (2011), which is hereby incorporated by reference in its entirety).

(h) Ethosomes (such as those described in Godin et al., "Ethosomes: New Prospects in Transdermal Delivery," *Crit. Rev. Ther. Drug Carrier Syst.* 20:63-102 (2003), which is hereby incorporated by reference in its entirety).

(i) Inhalation-based delivery systems (such as those described in Patton et al., "The Particle Has Landed—Characterizing the Fate of Inhaled Pharmaceuticals," *J. of Aerosol Medicine and Pul. Drug Del.* 23:Suppl 2: S71-87 (2010), which is hereby incorporated by reference in its entirety).

(j) Irradiated tumor cell-based delivery system (such as those described in Kim, et al., "Delivery of Chemotherapeutic Agents Using Drug-Loaded Irradiated Tumor Cells to Treat Murine Ovarian Tumors," *J. Biomed. Sci.* 17:61 (2010), which is hereby incorporated by reference in its entirety).

(k) Lipid-based carriers.

(l) Liposheres, such as acoustically active liposheres.

(m) Microencapsulated drug delivery (such as those described in Oettinger et al., "Microencapsulated Drug Delivery: A New Approach to Pro-Inflammatory Cytokine Inhibition," *J. Microencapsulation* (2012), which is hereby incorporated by reference in its entirety).

(n) A delivery system referred to as molecular umbrellas (such as those described in Cline et al., "A Molecular Umbrella Approach to the Intracellular Delivery of Small Interfering RNA," *Bioconjugate Chem.* 22:2210-2216 (2011), which is hereby incorporated by reference in its entirety).

(o) Niosomes (non-ionic surfactant-based liposomes).

(p) Photo-activatible drug delivery systems.

(q) Polymeric microcapsule (such as those described in Pavlov et al., "Neuron Cells Uptake of Polymeric Microcapsules and Subsequent Intracellular Release," *Mac. Bio.* 11:848-854 (2011), which is hereby incorporated by reference in its entirety).

(r) Self-emulsifying drug delivery system (such as those described in Lei et al., "Development of a Novel Self-Microemulsifying Drug Delivery System for Reducing HIV Protease Inhibitor-Induced Intestinal Epithelial Barrier Dysfunction," *Mol. Pharmaceutics* 7:844-853 (2010), which is hereby incorporated by reference in its entirety).

(s) Trojan horse delivery systems.

(t) Vesicles including but not limited to reduction sensitive vesicles (such as those described in Park et al., "Reduction-Sensitive, Robust Vesicles with a Non-Covalently Modifiable Surface as a Multifunctional Drug-Delivery Platform," *Small* 6:1430-1441 (2010), which is hereby incorporated by reference in its entirety).

(u) Viral vectors and viral-like systems (such as those described in Bacman et al., "Organ-Specific Shifts in mtDNA Heteroplasmy Following Systemic Delivery of a Mitochondria-Targeted Restriction Endonuclease," *Gene Ther.* 17:713-720 (2010); Chailertvanitkul et al., "Adenovirus: a Blueprint for Non-Viral Gene Delivery," *Curr. Opin. Biotech.* 21:627-632 (2010), each of which is hereby incorporated by reference in its entirety).

It should be noted that the above listed drug delivery systems can be used in combination with each other. They also can be engineered further to provide target cell or tissue type delivery or targeted cell/tissue-type exclusion. In addition, new nanoscopic delivery systems are being developed frequently, and a variety of materials for use in the formation of nanoscopic drug delivery vehicles is expanding rapidly.

The above delivery systems can be used in combination with enhanced delivery techniques. Examples of such techniques include the following items (I)-(XV).

(I) Amphotercin B-mediated drug delivery enhancement.

(II) Ultrasound-mediated techniques (such as those described in Grimaldi et al., "Ultrasound-Mediated Structural Changes in Cells Revealed by FTIR Spectroscopy: a Contribution to the Optimization of Gene and Drug Delivery," *Spectrochim. Acta Part A* 84:74-85 (2011); Yudina et al., "Ultrasound-Mediated Intracellular Drug Delivery Using Microbubbles and Temperature-Sensitive Liposomes," *J. Controlled Release* 155:442-448 (2011), each of which is hereby incorporated by reference in its entirety).

(III) Temperature-sensitive delivery and/or release systems.

(IV) pH-sensitive delivery and/or release systems.

(V) Redox-responsive delivery systems, such as those described in (Zhao et al., "A Novel Human Derived Cell-Penetrating Peptide in Drug Delivery," *Mol. Biol. Rep.* 38:2649-2656 (2011), which is hereby incorporated by reference in its entirety).

(VI) Bioreducible delivery systems (such as those described in Liu et al., "Bioreducible Micelles Self-Assembled from Amphiphilic Hyperbranched Multiarm Copolymer for Glutathione-Mediated Intracellular Drug Delivery," *Biomacromolecules* 12: 1567-1577 (2011), which is hereby incorporated by reference in its entirety).

(VII) Methods to enhance endolysomal escape (such as those described in Paillard et al., "The Importance of Endo-Lysosomal Escape with Lipid Nanocapsules for Drug Subcellular Bioavailability," *Biomaterials* 31:7542-7554 (2010), which is hereby incorporated by reference in its entirety).

(VIII) Inhalation methods (such as those described in Zhuang et al., "Treatment of Brain Inflammatory Diseases by Delivering Exosome Encapsulated Anti-Inflammatory Drugs from the Nasal Region to the Brain," *Mol. Ther.* 19:1769-1779 (2011), which is hereby incorporated by reference in its entirety).

(IX) Methods to enhance oral delivery (such as those described in Muller, "Oral Delivery of Protein Drugs: Driver for Personalized Medicine," *Curr. Molec. Bio.* 13:13-24 (2011), which is hereby incorporated by reference in its entirety).

(X) Targeted cell delivery systems, some of which have been developed for use in the delivery of anti-HIV drugs (such as those described in Bronshtein et al., "Cell Derived Liposomes Expressing CCR5 as a New Targeted Drug-Delivery System for HIV Infected Cells," *J. Controlled Release* 151:139-148 (2011); Gunaseelan et al., "Surface Modifications of Nanocarriers for Effective Intracellular Delivery of Anti-HIV Drugs," *Adv. Drug Delivery Rev.* 62:518-531 (2010); Kelly et al., "Targeted Liposomal Drug Delivery to Monocytes and Macrophages.," *J. Drug Delivery* 727241 (2011), each of which is hereby incorporated by reference in its entirety).

(XI) Slow or on-demand release systems (such as those described in Hu et al., "Multifunctional Nanocapsules for Simultaneous Encapsulation of Hydrophilic and Hydrophobic Compounds and On-Demand Release," *ACS Nano* 6:2558-2565 (2012), which is hereby incorporated by reference in its entirety).

(XII) Targeted delivery to one or more receptors (such as those described in Ming, "Cellular Delivery of siRNA and Antisense Oligonucleotides via Receptor-Mediated Endocytosis," *Expert Opin. on Drug Delivery* 8:435-449 (2011), which is hereby incorporated by reference in its entirety).

(XIII) Targeted delivery to one or more different subcellular organelles (such as those described in Paulo et al., "Nanoparticles for Intracellular-Targeted Drug Delivery," *Nanotechnol.* 22:494002 (2011); Zhang et al., "Newly Developed Strategies for Multifunctional Mitochondria-Targeted Agents In Cancer Therapy," *Drug Discovery Today* 16:140-146 (2011), which is hereby incorporated by reference in its entirety).

(XIV) Methods to improve or to regulate drug uptake (such as those described in Lorenz, S et al., "The Softer and More Hydrophobic the Better: Influence of the Side Chain Of Polymethacrylate Nanoparticles for Cellular Uptake," *Macromol. Bioscience* 10:1034-1042 (2010); Ma et al., "Distinct Transduction Modes of Arginine-Rich Cell-Penetrating Peptides for Cargo Delivery into Tumor Cells," *Int. J. Pharm.* 419:200-208 (2011), each of which is hereby incorporated by reference in its entirety).

(XV) Methods that use erythrocytes as drug carriers as described in, e.g., Millan et al., "Drug, Enzyme and Peptide Delivery using Erythrocytes As Carriers," *J. Control Release* 95:27-49 (2004), which is hereby incorporated by reference in its entirety.

Although delivery of amifostine (the phosphorothioate) using nanoparticles has been reported previously (Pamujula et al., "Oral Delivery of Spray Dried PLGA/Amifostine Nanoparticles," *J. Pharm. Pharmacol.* 56:1119-1125 (2004); Pamujula et al., "Preparation and In Vitro Characterization of Amifostine Biodegradable Microcapsules," *Eur. J. Pharm. Biopharm.* 57:213-218 (2004); Pamujula et al., "Radioprotection in Mice Following Oral Delivery of Amifostine Nanoparticles," *Int. J. Radiat. Biol.* 81:251-257 (2005); (Pamujula et al., "Radioprotection of mice following oral administration of WR-1065.PLGA nanoparticles," *Int. J. Radiat. Biol.* 84:900-908 (2008), each of which is hereby incorporated by reference in its entirety), this delivery system was different than the aminothiol-conjugates and compositions described herein and does not resolve the problems associated with dependence upon alkaline phosphatase for drug activation. Unlike aminothiol-conjugates described herein, such delivery systems do not resolve the problems of adventitious drug reactivity in circulation or drug release distal to target cells. This previous attempt also fails to address the potential toxicity problems associated with activation of the drug outside of cells.

Other methods that can be used to alter or improve drug delivery and/or uptake include the use of surfactants as described in U.S. Pat. No. 6,489,312 to Stogniew, which is hereby incorporated by reference in its entirety.

In certain embodiments, the active form of the aminothiol (or analogue thereof) is released intracytoplasmically to achieve therapeutic effects. In general any drug delivery system and/or drug protection method that includes the capacity to release the active form of the drug following intracytoplasmic delivery can be used. The key to the selection of one or more of the protection and delivery systems described above is to recognize that once the drug has been delivered into the cytoplasm of target cells, the delivery/protection method must allow for release of the aminothiol. Thus, binding of the conjugate to the aminothiol must be carried out so as to result in a reducible (bioreducible) disulfide bond (Benham et al., "Disulfide Bonding Patterns and Protein Topologies," *Protein Sci.* 2:41-54 (1993); Liu et al., "Disulfide Bond Structures of IgG Molecules: Structural Variations, Chemical Modifications and Possible Impacts to Stability and Biological Function," *mAbs* 4:17-23 (2012), each of which is hereby incorporated by reference in its entirety).

Another aspect of the present invention relates to a method of treating a subject in need of aminothiol therapy. The method involves administering to a subject in need thereof one or more of the aminothiol-conjugates described herein. The method may involve administering to the subject (i) an aminothiol-conjugate of formula (IV), as described above. The method may involve administering to the subject (i) an aminothiol-conjugate of formula (I), as described above.

As used herein, treatment means any manner in which one or more of the symptoms of a disease or disorder are ameliorated or otherwise beneficially altered. A therapeutically effective amount of aminothiol-conjugates as described herein can be, e.g., an amount sufficient to prevent the onset of a disease state or to shorten the duration of a disease state, or to decrease the severity of one or more symptoms. Treatment includes inhibition and attenuation of, e.g., viruses or pathogenic microorganisms in the subject.

Amifostine, phosphonol, and structurally-related phosphorothioates and analogs have been shown to have therapeutic efficacy when used as chemoprotectants, cytoprotectants, radioprotectants, anti-fibrotic agents, anti-tumor agents with anti-metastatic, anti-invasive, and anti-mutagenic effects, antioxidants, free radical scavengers, anti-viral agents, and as agents that prevent tumor induction, slow tumor cell growth, have antitumor/anticancer effects and/or enhance the efficacy of anticancer agents (Grdina et al., "Differential Activation of Nuclear Transcription Factor Kappab, Gene Expression, and Proteins By Amifostine's Free Thiol in Human Microvascular Endothelial and Glioma Cells," *Semin. Radiat. Oncol.* 12:103-111 (2002); Grdina et al., "Relationships between Cytoprotection and Mutation Prevention by WR-1065," *Mil Med* 167: 51-53 (2002); Grdina et al. "Radioprotectors: Current Status and New Directions," *Radiat. Res.* 163:704-705 (2002); Poirier et al., "Antiretroviral Activity of the Aminothiol WR1065 Against Human Immunodeficiency Virus (HIV-1) in Vitro and Simian Immunodeficiency Virus (SIV) Ex Vivo," *AIDS Res. Ther.* 6:24 (2009); Walker et al., "WR1065 Mitigates AZT-ddI-Induced Mutagenesis and Inhibits Viral Replication," *Environ. Mol. Mutagen.* 50:460-472 (2009), each of which is hereby incorporated by reference in its entirety). Experimental results have shown that WR-1065, the active metabolite of amifostine, exhibited antiviral efficacy against HIV, influenza virus A and B, and three species of adenovirus. Later studies also demonstrated efficacy against SIV (Poirier et al., "Antiretroviral Activity of the Aminothiol WR1065 Against Human Immunodeficiency Virus (HIV-1) in Vitro and Simian Immunodeficiency Virus (SIV) Ex Vivo," *AIDS Res. Ther.* 6:24 (2009), which is hereby incorporated by reference in its entirety) and a NIAID/DMID contract laboratory demonstrated efficacy against Ebola virus.

In certain embodiments, the subject is one in need of treatment with an antiviral agent, a chemoprotectant, a cytoprotectant, a radioprotectant, an anti-fibrotic agent, an anti-tumor agent, an antioxidant, or a combination thereof.

In certain embodiments, the subject is not infected with HIV.

In certain embodiments, the subject is in need of antimicrobial therapy and the aminothiol-conjugate or pharmaceutical composition comprising aminothiol-conjugate is administered under conditions effective to kill one or more pathogenic microorganisms in the subject. The microorganism may be, for example, a bacterium, a yeast, a fungus, or a parasite. The parasite may be intracellular parasite or an extracellular parasite.

In one embodiment, the subject is infected with a virus and the aminothiol-conjugate (or pharmaceutical composition including the aminothiol-conjugate) is administered under conditions effective to treat the virus. In certain embodiments, a therapeutically effective amount of the aminothiol-conjugate described herein is an amount sufficient to reduce the viral load of the target virus in the subject.

The subject may be one that is infected with HIV, orthomyxovirus, influenza virus, adenovirus, or a combination thereof. In one embodiment, the subject is not infected with HIV.

In one embodiment, the subject is one infected with influenza. The influenza virus may be, e.g., H1N1 or H3N2.

In one embodiment, the subject is one infected with adenovirus. The adenovirus may be of the species B, C, or E.

In one embodiment, the subject is one infected with Ebola virus.

As noted above, one aspect of the present invention relates to a method of treating a subject with a neoplastic condition by administering an aminothiol-conjugate or pharmaceutical composition comprising aminothiol-conjugate as described herein under conditions effective to treat the neoplastic condition. Another aspect of the present invention, relates to a method of treating a subject at risk of developing a neoplastic condition by administering an aminothiol-conjugate or pharmaceutical composition comprising aminothiol-conjugate as described herein under conditions effective to reduce the risk of developing the neoplastic condition. Such a subject at risk of developing a neoplastic condition includes, e.g., a subject receiving repeated diagnostic radiation exposures.

For instance, sensitive tumor types identified through in vitro studies include: breast cancer, ovarian cancer, malignant melanoma (Brenner et al., "Variable Cytotoxicity of Amifostine in Malignant and Non-Malignant Cell Lines," *Oncol. Rep.* 10(5):1609-13 (2003), which is hereby incorporated by reference in its entirety); ovarian cancer (Calabro-Jones et al., "The Limits to Radioprotection of Chinese Hamster V79 Cells by WR-1065 Under Aerobic Conditions," *Radiat. Res.* 149:550-559 (1998) ("Calabro-Jones"), which is hereby incorporated by reference in its entirety); cervical carcinoma cells (HeLa cells and Me-180-VCII) (see Calabro-Jones); colon carcinoma (see Calabro-Jones); lung cancer (A549 cells and H1299): (verbal communication from Dr. A. Kajon; Pataer et al., "Induction of Apoptosis in Human Lung Cancer Cells Following Treatment With Amifostine and an Adenoviral Vector Containing Wild-Type p53," *Cancer Gene Ther.* 13(8):806-14 (2006), each of which is hereby incorporated by reference in its entirety); and myelodysplastic syndrome (Ribizzi et al., "Amifostine Cytotoxicity and Induction of Apoptosis in a Human Myelodysplastic Cell Line," *Leuk. Res.* 24(6):519-25 (2000), which is hereby incorporated by reference in its entirety). Sensitive tumor types identified through in vivo studies include, for example, metastatic melanoma (Glover et al., "WR-2721 and High-Dose Cisplatin: An Active Combination in the Treatment of Metastatic Melanoma," *J. Clin. Oncol.* 5(4):574-8 (1987), which is hereby incorporated by reference in its entirety); radiation-induced tumor types (Grdina et al., "Protection Against Late Effects of Radiation by S-2-(3-aminopropylamino)-ethylphosphorothioic Acid," *Cancer Res.* 51(16):4125-30 (1991), which is hereby incorporated by reference in its entirety) (reporting that amifostine reduced the occurrence of all tumors representing 160 tumor classification codes for a wide range of radiation-induced tumor types in mice); lymphoreticular tumors (e.g., fibrosarcoma-lymph node, histiocytic leukemia, histiocytic lymphoma, lymphocytic-lymphoblastic lymphoma, myelogenous leukemia, plasma cell tumors, undifferentiated leukemia, undifferentiated lymphoma, unclassified lymphoma, mixed histiocytic-lymphocytic leukemia, and mixed histiocytic-lymphocytic lymphoma) (Grdina et al., "Protection Against Late Effects of Radiation by S-2-(3-aminopropylamino)-ethylphosphorothioic Acid," *Cancer Res.* 51(16): 4125-30 (1991), which is hereby incorporated by reference in its entirety); radiation-induced mammary tumors (Inano et al., "Inhibitory Effects of WR-2721 and Cysteamine on Tumor Initiation in Mammary Glands of Pregnant Rats by Radiation," *Radiat Res.* 153(1):68-74 (2000), which is hereby incorporated by reference in its entirety); radiation-induced sarcomas (Milas et al. "Inhibition of Radiation Carcinogenesis in Mice by S-2-(3-aminopropylamino)-ethylphosphorothioic Acid," *Cancer Res.* 44(12 Pt 1):5567-9 (1984), which is hereby incorporated by reference in its entirety); neutron-induced tumorigenicity (Grdina et al., "Protection by WR-151327 Against Late-Effect Damage From Fission-Spectrum Neutrons," *Radiat. Res.* 128(1 Suppl):S124-7 (1991) (reporting that the WR1065 analog WR151327 reduced fission-spectrum neutron-induced tumor induction in male and female mice when administered 30 min prior to irradiation) and Carnes et al., "In Vivo Protection by the Aminothiol WR-2721 Against Neutron-Induced Carcinogenesis," *Int. J. Radiat. Biol.* 61(5):567-76 (1992) (reporting that WR2721 protected against neutron-induced tumor induction in male and female B6C3F1 mice), each of which is hereby incorporated by reference in its entirety); myelodysplastic syndrome (Mathew et al., "A Phase II Study of Amifostine in Children With Myelodysplastic Syndrome: A Report From the Children's Oncology Group Study (AAML0121)," *Pediatr. Blood Cancer* 57(7): 1230-2 (2011), which is hereby incorporated by reference in its entirety); and secondary tumors induced by radiation or chemotherapy in animal models (Grdina et al., "Protection Against Late Effects of Radiation by S-2-(3-aminopropylamino)-ethylphosphorothioic Acid," *Cancer Res.* 51(16): 4125-30 (1991); Grdina et al., "Radioprotectants: Current Status and new Directions," *Oncology* 63 (Suppl. 2):2-10 (2002); Grdina et al., "Radioprotectors in Treatment Therapy to Reduce Risk in Secondary Tumor Induction," *Pharmacol. Ther.* 39(1-3):21-5 (1988), each of which is hereby incorporated by reference in its entirety).

Further, the anti-cancer effects of aminothiols (e.g., amifostine (WR2721) and WR1065) have been well-established. Exemplary anti-cancer effects include anti-neoplastic transformation, anti-mutagenesis in normal cells, anti-angiogenesis, inhibition or reduction of tumor cell growth, inhibition or reduction of tumor cell invasion, and inhibition or reduction of tumor cell metastasis. Exemplary anti-cancer effects identified through in vitro or in vivo studies are summarized below.

Anti-neoplastic transformation: In in vitro experiments, V79 cells were irradiated with gamma rays and exposed to 1 milliM WR1065 simultaneously and the incidence of neoplastic transformation was assessed (Hill et al., "2-[(Aminopropyl)amino]ethanethiol (WR1065) is Anti-Neoplastic and Anti-Mutagenic When Given During 60Co Gamma-Ray Irradiation," *Carcinogenesis* 7(4):665-8 (1986), which is hereby incorporated by reference in its entirety.) Neoplastic transformation was reduced significantly even though cell viability was not changed. In in vitro experiments, WR1065 and WR151326, at 1 milliM each, were shown to protect C3H/10T1/2 cells from neoplastic transformation induced by exposure to fission neutrons, and this effect was observed for two different radiation exposure protocols (Balcer-Kubiczek et al, "Effects of WR-1065 and WR-151326 on Survival and Neoplastic Transformation in C3H/10T1/2 Cells Exposed to TRIGA or JANUS Fission Neutrons," *Int. J. Radiat. Biol.* 63(1):37-46 (1993), which is hereby incorporated by reference in its entirety). The cells were exposed to WR1065 or WR151326 before, during, and after the radiation exposure. The protection factor for WR1065 was 3.23, while for WR151326 it was 1.8. In in vivo experiments, WR2721 administered at 100 micrograms/g body weight protected young rats from the formation of radiation-induced hepatic foci; this effect was more pronounced in female rats, the gender most susceptible to hepatocellular focus formation (Grdina et al, "Protective Effect of S-2-(3-aminopropylamino)ethylphosphorothioic Acid Against Induction of Altered Hepatocyte Foci in Rats Treated Once With Gamma-Radiation Within one day After Birth," *Cancer Res.* 45(11 Pt 1):5379-81 (1985), which is hereby incorporated by reference in its entirety). In in vivo experiments, WR2721 exposure inhibited radiation-induced cell transformation in a mouse model, with 26% of mice receiving WR2721 plus radiation developing tumors, compared to 87% of mice receiving radiation alone (Milas et al. "Inhibition of Radiation Carcinogenesis in Mice by S-2-(3-aminopropylamino)-ethylphosphorothioic Acid," *Cancer Res.* 44(12 Pt 1):5567-9 (1984), which is hereby incorporated by reference in its entirety). In vivo studies were conducted to determine if WR2721 could protect immune system cells from the damaging effects (lung colonization and increased tumor take/seeding capacity using a fibrosarcoma) of whole body irradiation plus chemotherapy with cyclophosphamide in a mouse model (Milas et al., "Protection by S-2-(3-aminopropylamino)ethylphosphorothioic Acid Against Radiation- and Cyclophosphamide-Induced Attenuation in Antitumor Resistance," *Cancer Res.* 44(6): 2382-6 (1984), which is hereby incorporated by reference in its entirety). The authors found that WR2721 almost completely eliminated the tumor-take enhancing effects of whole body irradiation in C3Hf/Kam mice. In in vivo experiments, female C57/BL/6JANL x BALB/cJANLF1 mice were exposed to 0, 206 cGy gamma rays, 417 cGy gamma rays, or the same doses of radiation with 400 mg/kg WR2721; animals were held for life(Grdina et al., "Protection Against Late Effects of Radiation by S-2-(3-aminopropylamino)-ethylphosphorothioic Acid," *Cancer Res.* 51(16):4125-30 (1991), which is hereby incorporated by reference in its entirety). 90% of the irradiated animals died of tumors; significant protection was seen for WR2721 treated mice that were irradiated with 206 cGy. Lymphoreticular tumors were particularly sensitive to the protective effect; total life expectancy was extended 65 days. In in vivo experiments, Amifostine has been shown to reduce radiation-induced mammary tumors in pregnant rats (Grdina et al., "Amifostine: Mechanisms of Action Underlying Cytoprotection and Chemoprevention," *Drug Metabol. Drug Interact.* 16(4):237-79 (2000), which is hereby incorporated by reference in its entirety).

Anti Mutagenesis In Normal Cells: In in vitro experiments, using WR1065 at 4 milliM and simultaneous gamma ray irradiation of V79 cells, HPRT mutations were reduced significantly and cell viability was increased(Hill et al., "2-[(Aminopropyl)amino]ethanethiol (WR1065) is Anti-Neoplastic and Anti-Mutagenic When Given During 60Co Gamma-Ray Irradiation," *Carcinogenesis* 7(4):665-8 (1986), which is hereby incorporated by reference in its entirety). In in vitro experiments, a dose of 4 milliM resulted in significant increases in cellular glutathione levels and cysteine levels, and these were associated with significant cytoprotection and anti-mutagenesis against 60Co gamma-photon and neutron radiation (Grdina et al., "Thiol and Disulfide Metabolites of the Radiation Protector and Potential Chemopreventive Agent WR-2721 are Linked to Both its Anti-Cytotoxic and Anti-Mutagenic Mechanisms of Action," *Carcinogenesis* 16(4):767-74 (1995), which is hereby incorporated by reference in its entirety). In in vitro experiments, WR1065 protected GO T-lymphocytes from mutation induction due to ionizing radiation, showing protection in a non-cycling cell (Clark et al., "Hprt Mutations in Human T-Lymphocytes Reflect Radioprotective Effects of the Aminothiol, WR-1065," *Carcinogenesis* 17 (12), 2647-2653(1996), which is hereby incorporated by reference in its entirety). In in vitro experiments in GO T-lymphocytes, WR1065 reduced the induction of mutations indicative of gross structural alterations (Clark et al., "The Aminothiol WR-1065 Protects T Lymphocytes From Ionizing Radiation-Induced Deletions of the HPRT Gene," *Cancer Epidemiol. Biomarkers. Prev.* 6(12):1033-7 (1997), which is hereby incorporated by reference in its entirety). In in vitro experiments, amifostine reduced cyclophosphamide-induced mutations in the HPRT gene 8-fold in mouse splenocytes (Grdina et al., "Chemopreventive Doses of Amifostine Confer no Cytoprotection to Tumor Nodules Growing in the Lungs of Mice Treated With Cyclophosphamide," *Semin. Oncol.* 26(2 Suppl 7):22-7 (1999), which is hereby incorporated by reference in its entirety). In in vitro experiments using a mouse model injected IV with fibrosarcoma cells intended to colonize the lung, the ability of WR1065 to prevent HPRT mutations due to cyclophosphamide exposure was evaluated (Kataoka et al., "Antimutagenic Effects of Amifostine: Clinical Implications," *Semin. Oncol.* 23(4 Suppl 8):53-7 (1996), which is hereby incorporated by reference in its entirety). At 100 mg/kg, WR1065 did not reduce the anticancer effectiveness of cyclophosphamide, but did reduce significantly HPRT mutation frequencies induced by this chemotherapeutic agent. In in vitro experiments, it was found that WR1065, at a concentration of 4 milliM, provided significant protection against induction of mutations in the HPRT gene due to exposure to the chemotherapeutic agent cis-DDP (Nagy et al., "Protection Against cis-diamminedichloroplatinum Cytotoxicity and Mutagenicity in V79 Cells by 2-[(aminopropyl)amino]ethanethiol," *Cancer Res.* 46(3):1132-5 (1986), which is hereby incorporated by reference in its entirety). In in vitro experiments, the ability of WR1065, at 4 milliM, to protect against mutation induction in the HPRT gene, induction of single strand breaks, and cell killing by bleomycin, nitrogen mustard, cis-DDP, or x-ray radiation was assessed (Nagy et al., "Protective Effects of 2-[(aminopropyl)amino] Ethanethiol Against Bleomycin and Nitrogen Mustard-Induced Mutagenicity in V79 Cells," *Int. J. Radiat. Oncol.* 12(8):1475-8, (1986.), which is hereby incorporated by reference in its entirety). WR1065 protected against all of these effects for each agent, but the degree of protection varied with the agent. In in vitro experiments, WR1065 and WR151326 were tested for their ability to prevent mutation induction at the HPRT gene due to exposure to fission-spectrum neutrons (Grdina et al., "Protection by WR1065 and WR151326 Against Fission-Neutron-Induced Mutations at the HGPRT Locus in V79 Cells," *Radiat. Res.* 117(3):500-10 (1989), which is hereby incorporated by reference in its entirety). Both agents protected against mutation induction, with WR1065 being more effective than WR151326 at preventing mutations. In in vivo experiments using B6C3F1 male mice, the ability of WR2721, at a dose of 400 mg/kg, to protect against mutation induction by JANUS fission-spectrum neutrons was assessed (Grdina et al., "The Radioprotector WR-2721 Reduces Neutron-Induced Mutations at the hypoxanthine-guanine Phosphoribosyl Transferase Locus in Mouse Splenocytes When Administered Prior to or Following Irradiation," *Carcinogenesis* 13(5):811-4 (1992), which is hereby incorporated by reference in its entirety). WR1065 reduced the mutant frequency when administered before, during, or after irradiation. However, the highest reduction factor was obtained when the dose administered was 50 mg/kg instead of 400 mg/kg.

Anti-Angiogenesis: Amifostine reduced the mRNA levels of VEGF isoforms VEGF(165) and VEGF(190) and angiogenesis in chicken embryo chorioallantoic membranes at doses not associated with signs of toxicity (Giannopoulou et al., "Amifostine has Antiangiogenic Properties in Vitro by Changing the Redox Status of Human Endothelial Cells," *Free Radic. Res.* 37(11):1191-9 (2003), which is hereby incorporated by reference in its entirety). WR2721 also reduced the mRNA levels of inducible nitric oxide synthase, and also reduced laminin and collagen deposition amounts in the same model "without affecting the expression of the corresponding genes." See id. MMP-2 protein levels were not affected, but gene expression was reduced. Last, plasmin activity was increased by amifostine. The authors concluded that these effects showed evidence that WR1065 inhibits angiogenesis. In another study, amifostine was shown to increase serum angiostatin levels 4-fold (Grdina et al., "Inhibition of Spontaneous Metastases Formation by Amifostine," *Int. J. Cancer* 97(2):135-41 (2002), which is hereby incorporated by reference in its entirety). Using the same in vivo mouse model system that was used in Grdina et al. (Grdina et al., "Inhibition of Spontaneous Metastases Formation by Amifostine," *Int. J. Cancer* 97(2):135-41 (2002), which is hereby incorporated by reference in its entirety), the authors found that doses of WR2721 of 200 mg/ml (instead of 50 mg/ml) did not change angiostatin levels (Grdina et al., "Antimetastatic Effectiveness of Amifostine Therapy Following Surgical Removal of Sa-NH Tumors in Mice," *Semin. Oncol.* 29(6 Suppl 19):22-8 (2002), which is hereby incorporated by reference in its entirety). The authors concluded that the mechanism for these effects was a redox driven process.

Inhibition or Reduction of Tumor Cell Growth: In a study relating to radiation-induced sarcomas, one half of mice were exposed to amifostine and 30 mins later the right hind legs of all mice (controls and amifostine-treated) were exposed to 3400 to 5700 rads (Milas et al. "Inhibition of Radiation Carcinogenesis in Mice by S-2-(3-aminopropylamino)-ethylphosphorothioic Acid," *Cancer Res.* 44(12 Pt 1):5567-9 (1984), which is hereby incorporated by reference in its entirety). Tumor cell growth rate was decreased in WR-2721 plus radiation-exposed mice when compared to mice exposed to radiation alone. In a study relating to Sa-NH sarcoma cells, C3Hf/Kam mice were injected with Sa-NH sarcoma cells and treated with WR2721 at 50 mg/kg every other day for 6 days while the tumors grew; then the tumors were removed by limb amputation and WR2721 was administered immediately after surgery and again 2 days later (Grdina et al., "Inhibition of Spontaneous Metastases Formation by Amifostine," *Int. J. Cancer* 97(2):135-41 (2002), which is hereby incorporated by reference in its entirety). Results to this point showed that amifostine was able to induce a slight delay in tumor growth, from 12 to 13 days for tumors to reach ideal size for amputation. In a study using Chinese hamster ovarian cells (CHO cells), WR1065m when administered at 4 milliM to Chinese hamster ovarian cells resulted in cell cycle delay at the G2/M phase (Grdina et al., "Inhibition of Topoisomerase II Alpha Activity in CHO K1 Cells by 2-[(aminopropyl)amino]ethanethiol (WR-1065)," *Radiat. Res.* 138(1):44-52 (1994), which is hereby incorporated by reference in its entirety.) In a further study relating to CHO cells, WR1065 exposure in the range of 4 microM to 4 millimolar for 30 min resulted in cell accumulated in G2 (Murley et al., "WR-1065, An Active Metabolite of the Cytoprotector Amifostine, Affects Phosphorylation of Topoisomerase II Alpha Leading to Changes in Enzyme Activity and Cell Cycle Progression in CHO AA8 Cells," *Cell Prolif.* 30(6-7):283-94 (1997), which is hereby incorporated by reference in its entirety). Further, it has been shown that WR1065-induced inhibition of topoisomerase II-alpha can result in alteration in cell population distribution throughout the cell cycle (Kataoka et al., "Activation of the Nuclear Transcription Factor kappaB (NFkappaB) and Differential Gene Expression in U87 Glioma Cells After Exposure to the Cytoprotector Amifostine," *Int. J. Radiat.* 53(1):180-9 (2002), which is hereby incorporated by reference in its entirety).

Inhibition or Reduction of Tumor Cell Invasion: In in vitro experiments in a model using chicken embryo chorioallantoic membranes, WR1065, at doses not associated with signs of toxicity, reduced gene expression of MMP-2 (an enzyme associated with tumor cell invasion), but protein levels were not affected (Giannopoulou et al., "Amifostine has Antiangiogenic Properties in Vitro by Changing the Redox Status of Human Endothelial Cells," *Free Radic. Res.* 37(11):1191-9 (2003), which is hereby incorporated by reference in its entirety). In in vitro experiments, WR2721 decreased the activity of matrix metalloproteinases (MMPs) -2 and -9 by 30 to 40%. WR2721 also inhibited the migration of Sa-NH cells through Matrigel in a dose dependent manner (Grdina et al., "Inhibition of Spontaneous Metastases Formation by Amifostine," *Int. J. Cancer* 97(2): 135-41 (2002), which is hereby incorporated by reference in its entirety). In in vivo experiments, C3Hf/Kam mice were injected with Sa-NH sarcoma cells and treated with WR2721 at 50 mg/kg every other day for 6 days while the tumors grew; then the tumors were removed by limb amputation and WR2721 was administered immediately after surgery and again 2 days later (Grdina et al., "Inhibition of Spontaneous Metastases Formation by Amifostine," *Int. J. Cancer* 97(2):135-41 (2002), which is hereby incorporated by reference in its entirety).

Inhibition or Reduction of Tumor Cell Metastasis: For the purpose of investigating the anti-metastatic effects of WR1065, C3Hf/Kam mice were injected with Sa-NH sarcoma cells and treated with WR2721 at 50 mg/kg every other day for 6 days while the tumors grew; then the tumors were removed by limb amputation and WR2721 was administered immediately after surgery and again 2 days later (Grdina et al., "Inhibition of Spontaneous Metastases Formation by Amifostine," *Int. J. Cancer* 97(2):135-41 (2002), which is hereby incorporated by reference in its entirety). Amifostine reduced the number of animals with metastases and the number of metastases per animal. In another study, Amifostine was shown to have paradoxical effects; pulmonary metastases were reduced significantly in animals administered 50 mg/kg. The dose of 100 mg/kg was less effective and 200 mg/kg had no effect on metastases in this study (Grdina et al., "Antimetastatic Effectiveness of Amifostine Therapy Following Surgical Removal of Sa-NH Tumors in Mice," *Semin. Oncol.* 29(6 Suppl 19):22-8 (2002), which is hereby incorporated by reference in its entirety). In a further study, it was found that WR2721 almost completely eliminated the tumor-take enhancing effects of whole body irradiation in C3Hf/Kam mice, and significantly reduced lung nodule formation in mice that received WBI with or without cyclophosphamide 5 days earlier (Milas et al., "Protection by S-2-(3-aminopropylamino)ethylphosphorothioic Acid Against Radiation- and Cyclophosphamide-Induced Attenuation in Antitumor Resistance," *Cancer Res.* 44(6):2382-6 (1984), which is hereby incorporated by reference in its entirety). Further, of the partial responses observed in patients with metastatic melanoma, 53% occurred in patients who had received prior chemotherapy, and metastatic sites that responded included subcutaneous sites, lymph nodes, lung, and liver (Glover et al., "WR-2721 and High-Dose Cisplatin: An Active Combination in the Treatment of Metastatic Melanoma," *J. Clin. Oncol.* 5(4):574-8 (1987), which is hereby incorporated by reference in its entirety). The mean response time was 4.5 months.

In addition to the anti-cancer effects described above, aminothiols (e.g., amifostine (WR2721) and WR1065) have been shown to have effects on other anti-cancer therapies. Exemplary effects on other anti-cancer therapies include enhancement of other anti-cancer therapies (e.g., enhanced cytotoxicity of chemotherapeutic agents, enhanced cytotoxic effects of radiation therapy, improved response to chemotherapy, selective radioprotective effect on non-cancerous cells). Exemplary effects on other anti-cancer therapies identified through in vitro or in vivo studies are summarized below.

Enhancement of anti-cancer therapies: In in vitro experiments, WR1065 enhanced the cytotoxicity of the chemotherapeutic agent bleomycin in human lymphocytes at the G0 stage of the cell cycle (Hoffmann et al., "Structure-Activity Analysis of the Potentiation by Aminothiols of the Chromosome-Damaging Effect of Bleomycin in G0 Human Lymphocytes," *Environ. Mol. Mutagen.* 37(2):117-27 (2001), which is hereby incorporated by reference in its entirety). In in vitro experiments, WR2721 combined with mafosfamide resulted in survival of normal myeloid and erythroid progenitor cells while increasing the degree of cell death of leukemic cells (List, "Use of Amifostine in Hematologic Malignancies, Myelodysplastic Syndrome, and Acute Leukemia," *Semin. Oncol.* 26(2 Suppl 7):61-5 (1999), which is hereby incorporated by reference in its entirety). In in vivo experiments, the combination of WR2721 and cisplatin resulted in improved partial responses compared to cisplatin alone (53% partial response versus 10%, respectively) in patients with advanced malignant melanoma (Glover et al., "WR-2721 and High-Dose Cisplatin: An Active Combination in the Treatment of Metastatic Melanoma," *J. Clin. Oncol.* 5(4):574-8 (1987), which is hereby incorporated by reference in its entirety. Minor responses were observed in an additional 3 out of 36 patients (8%). In in vivo experiments in the Canine Sarcoma Study, evidence was found that WR2721 enhanced the cytotoxic effects of radiation therapy for a subset of tumors, and did not affect the cytotoxicity of radiation in the remaining tumors (Koukourakis, "Amifostine: Is There Evidence of Tumor Protection?" *Semin. Oncol.* 30(6 Suppl. 18):18-30 (2003), which is hereby incorporated by reference in its entirety). In in vivo experiments, WR2721 had synergistic cytotoxicity when administered to mice in combination with oxygen radical-generating chemotherapeutic agents. In mice treated with WR2721, the glutathione synthesis pathway appeared to be inactivated. In addition, WR33278 was found to have strong inhibitory effects upon gamma-glutamylcysteine synthetase, which is the rate limiting enzyme in glutathione synthesis. Similar results were obtained for cysteamine and for oxygen radicals. Oxygen radicals increased the rate at which WR1065 was oxidized to WR33278 (Schor, "Mechanisms of Synergistic Toxicity of the Radioprotective Agent, WR2721, and 6-hydroxydopamine," *Biochem. Pharmacol.* 37(9):1751-62 (1988), which is hereby incorporated by reference in its entirety). In in vivo experiments, WR2721 given 30 minutes before whole body irradiation significantly increased the local radiocurability of 8 mm diameter fibrosarcoma tumors (Milas et al., "Protection by S-2-(3-aminopropylamino)ethylphosphorothioic Acid Against Radiation- and Cyclophosphamide-Induced Attenuation in Antitumor Resistance," *Cancer Res.* 44(6):2382-6 (1984), which is hereby incorporated by reference in its entirety). In in vivo experiments in mice bearing subcutaneous human ovarian carcinoma xenografts OVCAR-3, WR2721 enhanced the anti-tumor efficacy of carboplatin (Treskes et al., "Effects of the Modulating Agent WR2721 on Myelotoxicity and Anti-tumour Activity in Carboplatin-Treated Mice," *Eur. J. Cancer.* 30A(2):183-7 (1994), which is hereby incorporated by reference in its entirety). In in vivo experiments in a mouse model of two different tumor types, when amifostine was combined with MISO, additive toxicity effects were observed (Rojas et al., "Interaction of Misonidazole and WR-2721—II. Modification of Tumour Radiosensitization," *Br. J. Cancer* 47(1):65-72 (1983), which is hereby incorporated by reference in its entirety). Effects of the drugs appeared to be related to the oxygen status of the tumors and MISO can act as an oxygen-mimetic to reduce the radioprotection of WR2721. In in vivo experiments, amifostine was shown to enhance the cytotoxic effects of some chemotherapeutic agents such as cisplatin, carboplatin, and paclitaxel (Kurbacher et al., "Chemoprotection in Anticancer Therapy: The Emerging Role of Amifostine (WR-2721)," *Anticancer Res.* 18(3C):2203-10 (1998), which is hereby incorporated by reference in its entirety).

Further, it has been shown that anticancer effects occur at drug doses that lack or have minimal cytotoxic effects in normal cells, including bovine arterial endothelial cells (see Brenner et al., "Variable Cytotoxicity of Amifostine in Malignant and Non-Malignant Cell Lines," *Oncol. Rep.* 10(5):1609-13 (2003), which is hereby incorporated by reference in its entirety); liver (in vivo) (Shaw et al., "Metabolic Pathways of WR-2721 (ethyol, amifostine) in the BALB/c Mouse," *Drug Metab. Dispos.* 22(6):895-902 (1994) (no observable cytotoxicity at >7400 picomol/10(6) cells); kidney (in vivo) (Shaw et al., "Metabolic Pathways of WR-2721 (ethyol, amifostine) in the BALB/c Mouse," *Drug Metab. Dispos.* 22(6):895-902 (1994) (no observable cytotoxicity at >17,000 picomol/10(6) cells); small intestine (in vivo) (Shaw et al., "Metabolic Pathways of WR-2721 (ethyol, amifostine) in the BALB/c Mouse," *Drug Metab. Dispos.* 22(6):895-902 (1994) (no observable cytotoxicity at >3000 picomol/10(6) cells). Each of the above-cited references is hereby incorporated by reference in its entirety.

Accordingly, the subject according to the present invention may be one that is suffering from a neoplastic condition and the aminothiol-conjugate or pharmaceutical composition comprising aminothiol-conjugate is administered under conditions effective to treat the neoplastic condition. Treatment may include any anti-cancer effect in the subject, as described herein (e.g., anti-neoplastic transformation, anti-mutagenesis in normal cells, anti-angiogenesis, inhibition or reduction of tumor cell growth, inhibition or reduction of tumor cell invasion, and inhibition or reduction of tumor cell metastasis).

In one embodiment, the neoplastic condition is selected from the group consisting of breast, ovary, cervix, colon, lung, skin (malignant melanoma), lymphoreticular tumors, and combinations thereof. In one embodiment, the neoplastic condition is a myelodysplastic condition.

In one embodiment, the subject is one that receives radiation therapy, chemotherapy, or a combination thereof and the aminothiol-conjugate or pharmaceutical composition comprising aminothiol-conjugate is administered under conditions effective to reduce or decrease the adverse or undesirable side-effects of the radiation therapy, chemotherapy, or combination thereof.

In one embodiment, the subject is one that receives a cancer therapy (e.g., radiation therapy, chemotherapy, or a combination thereof) and the aminothiol-conjugate or pharmaceutical composition comprising aminothiol-conjugate is administered under conditions effective to enhance the efficacy of the cancer therapy.

In one embodiment, the subject is a mammal.

In one embodiment, the mammal is a human. In one embodiment, the mammal is a non-human animal.

The above improved drug delivery systems can be administered using any appropriate drug administration method(s) known or described in the future, including but not limited to intravenously, subcutaneously, orally, intraperitoneally, intranasally, intrarectally, topically, by inhalation and/or transdermal patch. The drugs can be encapsulated in any delivery module that achieves drug delivery to the desired target cell(s) including by encapsulation or incorporation into nanoparticles, micelles, liposomes, nanogels, or others (see above).

Drug dosing levels should be based upon the level of aminothiol (or analogue thereof) that is being delivered. Thus, the following discussion considers the dose of aminothiol being administered as opposed to the total amount of prodrug being administered. The total amount of prodrug will vary depending upon the nature of the prodrug being administered. The active moiety (the aminothiol) can be administered at dosages selected to provide the equivalent of 910 mg/m2 or less for a 60 kg BW adult human. This dosage is equivalent to 24.3 mg/kg BW for a 60 kg BW adult human being (or a total dose of 1456 mg for a 60 kg BW adult). Children have been given up to a 2700 mg/m2 total dose of aminothiol in the form of amifostine.

It can be desirable to administer the aminothiol at doses that are lower than this level when repeated dosing is needed or desired. In addition, it can be desirable to administer the compound using an initial high dose (a bolus dose) and then tapering down to lower doses to be repeated multiple times a week or administered as often as once a day. A dose of 740 mg/m$^2$ aminothiol or aminothiol equivalent is associated with fewer side effects (List et al., "Stimulation of Hematopoiesis by Amifostine in Patients with Myelodysplastic Syndrome," *Blood* 90:3364-3369 (1997), which is hereby incorporated by reference in its entirety), and is thus generally preferred. For daily dosing, 200-340 mg/m$^2$ of amifostine (544 mg total dose for a 60 kg BW adult) is generally preferred (Santini et al., "The Potential of Amifostine: from Cytoprotectant to Therapeutic Agent," *Haematologica* 84:1035-1042 (1999); Schuchter, "Guidelines for the Administration of Amifostine," *Semin Oncol* 23:40-43 (1996), each of which is hereby incorporated by reference in its entirety). WR2065, given by injection at 500-910 mg/m$^2$, has a plasma $T_{1/2}$ of ~10 minutes and has a peak plasma level of ~100 µM.

Rodent studies suggest the use of higher dosages. For example, the maximally tolerated dose (MTD) for WR-1065 (in the form of amifostine) in mice was 432 mg/kg BW administered i.p. and 720 mg/kg BW administered p.o., and the 100% effective radioprotective dose was about one half of the MTD. For aminothiol delivered in the form of phosphonol, the MTD was 893 mg/kg BW administered i.p. and 1488 mg/kg BW administered p.o., and the 100% effective radioprotective dose was about one half of the MTD. All of the aminothiols have MTDs in rodents of greater than 400 mg/kg BW.

Aminothiols including WR-1065 can be efficacious at very low concentrations, for example, down to 0.4 micromolar concentrations in some in vitro studies.

While it is generally preferred to formulate aminothiol-conjugate drugs for oral administration, the drugs can be formulated so as to allow them to be administered by other routes. It can be desirable in certain embodiments to formulate the drug for intravenous administration in order to maximize efficacy. Because of the structural similarities between WR-1065 and WR-255591, especially the similarities in the sulfhydryl ends of the molecules, WR-255591 is expected to behave in a manner similar to WR-1065.

An unusual feature of the aminothiols, and especially WR1065, is that intracellular levels of the aminothiol can be determined (Bai et al., "New Liquid Chromatographic Assay with Electrochemical Detection for the Measurement of Amifostine and WR1065," *J. Chromatogr. B. Analyt. Technol. Biomed. Life. Sci.* 772:257-265 (2002); Elas et al., "Oral Administration is as Effective as Intraperitoneal Administration of Amifostine in Decreasing Nitroxide EPR Signal Decay In Vivo. *Biochim. Biophys. Acta.* 1637:151-155 (2003); Shaw et al., "Pharmacokinetic Profile of Amifostine," *Semin. Oncol.* 23:18-22 (1996), each of which is hereby incorporated by reference in its entirety). This makes it possible to use intracellular aminothiol levels as a guide to drug administration. For anticancer effects, prodrug administration at levels that result in 30 to 100 nanomoles aminothiol per $10^6$ cells are recommended. For some tumor types, lower intracellular levels are equally effective and can be used. For breast cancers that fall into the same classification as MDA-MB-468 cells and/or that have the same or similar genetic, epigenetic and gene expression changes, intracellular levels in the range of 0.001 to 30 nanomoles aminothiol per $10^6$ cells are effective. For antiviral effects, administering the prodrug at dose levels that result in intracellular levels in the range of 0.001 to 30 nanomoles aminothiol per $10^6$ cells also is recommended.

To obtain the optimal therapeutic effects of the aminothiols, it can be desirable to administer the prodrug more than once. For multi-day or multi-week dosing, administration of the prodrug at dose levels that result in 0.000001 to 30 nanomoles aminothiol per $10^6$ cells is recommended. For all other therapeutic effects, including radioprotective and cytoprotective effects, the prodrug can be administered at dose levels that result in intracellular levels in that range from 1 to 100 nanomoles aminothiol per $10^6$ cells.

It should be noted that the levels of prodrug that are administered will vary considerably based upon the structure of the prodrug and the nature of the target cells for which therapeutic effects are sought. For target cells that express the polyamine or folic acid transport system, prodrugs designed to take advantage of these active transport systems generally can be administered at lower amounts that the amounts needed to obtain a comparable intracellular level using a prodrug that is not actively transported into the cell. In addition, the levels of expression of active transport systems can vary between diseased or stressed cells, and can be affected by prodrug treatment, with the result that lower prodrug doses may be sufficient to obtain a therapeutic effect when multiple doses are being administered over time.

Also contemplated are combination therapies including the aminothiol-conjugate prodrug described herein and one or more other agents. The prodrugs described herein can be administered in combination with other agents employed to obtain the therapeutic benefits of the aminothiols. One of the benefits of such combination therapies is that lower doses of the therapeutic agents can be administered and/or greater therapeutic effects can be achieved. Such lower dosages can be particularly advantageous for antiretroviral drugs known to have genotoxicity and mitochondrial toxicity.

The aminothiol-conjugates described herein (including derivatives, isomers, metabolites, or pharmaceutically acceptable esters, salts, and solvates thereof) can be incorporated into a pharmaceutically acceptable carrier, including incorporation into nanoparticles, for administration to an individual in need of the therapeutic effects of an aminothiol.

One aspect of the present invention relates to a pharmaceutical composition comprising an aminothiol-conjugate as described herein. In one embodiment, the aminothiol-conjugate has formula (IV), as described above. In one embodiment, the aminothiol-conjugate has formula (I), as described above.

The pharmaceutical composition may further include an intracellular delivery system. The intracellular delivery system may be selected from the group consisting of: (a) systems comprising a cell penetrating agent, (b) pH-responsive carriers, (c) C2-streptavidin delivery systems, (d) CH(3)-TDDS drug delivery systems, (e) hydrophobic bioactive carriers, (f) exosomes, (g) lipid-based delivery systems, (h) liposome-based delivery systems, (i) micellar delivery systems, (j) microparticles, (k) molecular carriers, (l) nanocarriers, (m) nanoscopic multi-variant carriers, (n) nanogels, (o) hybrid nanocarrier systems consisting of components of two or more particulate delivery systems, (p) nanoparticles, (q) peptide-based drug delivery systems, and (r) polymer- or copolymer-based delivery systems. In certain embodiments, the intracellular delivery system is a nanoparticle.

In certain embodiments, the pharmaceutical composition does not include a nanoparticle delivery system.

The pharmaceutical composition may also include a surfactant.

The pharmaceutical composition may also include a reducing agent.

Another aspect of the present invention relates to a composition comprising one or more different aminothiol-conjugates as described herein. In certain embodiments, the one or more different aminothiol-conjugates have an average molecular weight of 100,000 daltons or less. In certain embodiments, the one or more different aminothiol-conjugates have an average molecular weight of about 100,000 daltons; 20,000 daltons; 10,000 daltons; 5,000 daltons; 3,000 daltons; 2,000 daltons; or 1,000 daltons. In certain embodiments, the average molecular weight is about 9,000 to about 11,000 daltons. In certain embodiments, the average molecular weight is about 9,000 to about 11,000 daltons. In one embodiment, the average molecular weight is about 10,000 daltons. In one embodiment, the average molecular weight is about 10,500 daltons.

Another aspect of the present invention relates to a kit comprising one or more different aminothiol-conjugates as described herein.

Yet another aspect of the present invention relates to the kit, further comprising one or more additional therapeutic agents.

Because some of the aminothiol-conjugate prodrugs may be sensitive to oxidation, it can be desirable to administer the prodrugs in combination with reducing agents including, but not limited to, vitamin C and vitamin E. Other reducing agents include organic aldehydes, hydroxyl-containing aldehydes, and reducing sugars such as glucose, mannose, galactose, xylose, ribose, and arabinose. Other reducing sugars containing hemiacetal or keto groupings can be employed, for example, maltose, sucrose, lactose, fructose, and sorbose. Other reducing agents include alcohols, preferably polyhydric alcohols, such as glycerol, sorbitol, glycols, especially ethylene glycol and propylene glycol, and polyglycols such as polyethylene and polypropylene glycols.

The aminothiol-conjugates and portions thereof described herein also include the pharmaceutically acceptable salts thereof. The terms "pharmaceutically acceptable salts" and "a pharmaceutically acceptable salt thereof" as used herein are broad terms, and are to be given their ordinary and customary meaning to a person of ordinary skill in the art (and are not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; a salt of trifluoroacetic acid; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in compositions. While it may be possible to administer the compounds of the preferred embodiments in the form of pharmaceutically acceptable salts, it is generally preferred to administer the compounds in neutral form.

It is generally preferred to administer the compounds of preferred embodiments orally; however, other routes of administration are contemplated. Contemplated routes of administration include but are not limited to oral, parenteral, intravenous, subcutaneous, intrarectal, intranasal, transdermal, and by inhalation. The prodrugs can be formulated into liquid preparations for, e.g., oral administration. Suitable forms include suspensions, syrups, elixirs, and the like. Particularly preferred unit dosage forms for oral administration include tablets and capsules.

The pharmaceutical compositions of the prodrugs are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In certain embodiments it can be desirable to maintain the active compound in the reduced state. Accordingly, it can be desirable to include a reducing agent, such as vitamin C, vitamin E, or other reducing agents as are known in the pharmaceutical arts, in the formulation.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The prodrugs can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the active compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers. In instances where it is desirable to maintain a compound of a preferred embodiment in a reduced form (in the case of certain active metabolites), it can be desirable to include a reducing agent in the capsule or other dosage form.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

Preferably, each tablet or capsule contains from about 10 mg or less to about 1,000 mg or more of the prodrug of choice, more preferably from about 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. For certain applications, it can be preferred to incorporate two or more of the prodrugs to be administered into a single tablet or other dosage form (e.g., in a combination therapy); however, for other applications it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose. Surfactants as described by U.S. Pat. No. 6,489,312 to Stogniew (which is hereby incorporated by reference in its entirety) may also be used.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of active compound doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

When a selected prodrug is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The pharmaceutical compositions composed of one or more selected prodrug can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, and the like), or can contain materials useful in physically formulating various dosage forms of the preferred embodiments, such as excipients, dyes, thickening agents, stabilizers, preservatives or antioxidants.

The prodrugs can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents. For example, a kit containing one or more compositions comprising one or more prodrugs in combination with one or more additional therapeutic agent (antimicrobials, antipruritics, astringents, local anesthetics, anti-inflammatory agents, reducing agents, and the like) can be provided, or separate pharmaceutical compositions containing one or more selected prodrugs and additional therapeutic agents can be provided. The kit can also contain separate doses of prodrug for serial or sequential administration. The kit can optionally contain one or more diagnostic tools and instructions for use. The kit can contain suitable delivery devices, e.g., syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject.

The prodrugs can be administered prophylactically for the prevention of induction of a stress state or disease state in cells of an individual in need of such therapy. Alternatively, therapy is preferably initiated as early as possible following the onset of signs and symptoms of a stress state or disease state. The administration route, amount administered, and frequency of administration will vary depending on the age of the patient, the severity of the infection, and any associated conditions. Contemplated amounts, dosages, and routes of administration for the prodrugs for treatment of disease states such as cancer or infection with a microbial pathogen are similar to those established for conventional anticancer and antiviral agents. Detailed information relating to administration and dosages of conventional antiretroviral agents can be found in the Physician's Desk Reference, 47th edition, which is hereby incorporated by reference in its entirety. This information can be adapted in designing treatment regimens utilizing the prodrugs.

Contemplated amounts of the prodrugs for oral administration to treat cancer, pathogen/microbial infections, or for cytoprotection range from about 10 mg or less to about 2000 mg or more administered from about every 24 hours or less to about every 6 hours or more (or from about 1 time daily to about 6 times daily) for about 5 days or less to about 10 days or more (40 mg/day or less to about 15,000 mg/day or more) or until there is a significant improvement in the condition. For suppressive therapy to inhibit the onset of cancer or infection in susceptible individuals, doses of from about 10 mg or less to about 1000 mg or more are orally administered once, twice, or multiple times a day, typically for up to about 12 months, or, in certain circumstances, indefinitely (from about 10 mg/day to about 1,000 mg/day). When treatment is long term, it can be desirable to vary the dosage, employing a higher dosage early in the treatment, and a lower dosage later in the treatment.

The single highest dose of amifostine administered to an adult human as documented in the literature was 1330 mg/m2. Children have been administered single doses of amifostine of up to 2700 mg/m2 with no untoward effects. The literature indicates that multiple doses (up to three times the recommended single dose of 740 to 910 mg/m2) have been safely administered within a 24-hour period. Repeated administration of amifostine at two and four hours after the initial dose does not appear to result in an increase in side effects, especially nausea, vomiting, or hypotension. It appears that the most significant deleterious side effect from the administration of amifostine is hypotension.

Contemplated amounts of the compounds of the preferred embodiments, methods of administration, and treatment schedules for individuals with AIDS are generally similar to those described above for treatment of HIV.

Known side effects of amifostine include decrease in systolic blood pressure, nausea, and vomiting. If such side effects are observed for the particular thiophosphate administered, it is generally preferred to administer an antiemetic medication prior to, or in conjunction with the thiophosphate. Suitable antiemetic medications include antihistamines (e.g., buclizine, cyclizine, dimenhydrinate, diphenhydramine, meclizine), anticholinergic agents (e.g., scopolamine), dopamine antagonists (e.g., chlorpromazine, droperidol, metoclopramide, prochlorperazine, promethazine), serotonin antagonists (e.g., dolasetron, granisetron, ondansetron), or other agents (e.g., dexamethasone, methylprednisolone, trimethobenzamide).

EXAMPLES

Example 1—Cytotoxic Effects of 4-Arm-Star-PEG-WR1065 (4-Arm-PEG Conjugated to WR1065) in Six Tumor Cell Lines To evaluate the anticancer activity of 4-arm star polyethylene glycol conjugated to WR-1065 (4SP65), the anticancer efficacy of 4SP65 was determined in some of the same cell lines used by NIH/NCI, and the methodology used was the same as is used by the NCI to evaluate chemotherapeutic agents currently in use (O'Connor et al., "Characterization of the p53 Tumor Suppressor Pathway in Cell Lines of the National Cancer Institute Anticancer Drug Screen and Correlations With the Growth-Inhibitory Potency of 123 Anticancer Agents," *Cancer Res.* 57(19):4285-300 (1997), which is hereby incorporated by reference in its entirety). Testing of 6 cancer types was completed: (i) breast cancer (MDA-MB-231 cells), (ii) lung cancer (A549), (iii) malignant melanoma (SK-MEL-28), (iv) myelogenous leukemia (HL60 cells), (v) ovarian cancer (SK-OV-3), and (vi) prostate cancer (DU-145). The growth inhibitory dose 50% for each cell line is presented in Table 1.

For comparison purposes, the growth inhibitory dose of 4SP65 required to reduce the growth of normal human mammary epithelial cells by 50% was above 300 micromolar. The exact value has not been determined as of yet due to the fact that 4SP65 forms a hydrogel in medium when present at a concentration that exceeds 300 micromolar.

TABLE 1

Average Growth Inhibitory Doses Required to Reduce in Vitro Cell Growth by 50% following a 48 hour exposure to 4SP65

| Tumor Type | Average Growth Inhibitory Dose 50% [EC(50)] (micromolar) |
| --- | --- |
| Breast CA (MDA-MB-231) | 4.5 |
| Lung CA (A549) | 15 |
| Malignant melanoma (SK-MEL-28) | 9.5 |

TABLE 1-continued

Average Growth Inhibitory Doses Required to Reduce in Vitro
Cell Growth by 50% following a 48 hour exposure to 4SP65

| Tumor Type | Average Growth Inhibitory Dose 50% [EC(50)] (micromolar) |
|---|---|
| Myelogenous Leukemia (HL60) | 3 |
| Ovarian CA (SK-OV-3) | 5 |
| Prostate CA (DU-145) | 6.7 |

The methods used to obtain the EC (50) values presented in Table 1 were as follows. Each cell line was grown in medium as recommended by the ATCC or as presented in the literature for that cell line. All cells were cultured in a water jacket incubator at 36-37° C. and in the presence of 5% $CO_2$. To ensure optimal growth and viability, all cells were grown on plates coated with FNC (InVitrogen). Cells were referred with growth medium twice weekly until they had reached 60 to 70% confluence. At this point, the medium was replaced with growth medium supplemented with 4SP65 at doses ranging from 0 to up to 300 micromolar. Cells were allowed to grow in the presence of this supplemented medium for 48 hrs, and then they were removed by trypsinization, stained with Trypan Blue and counted in a hemocytometer. Three to four replicates for each dose group per experiment were performed. The percentage cell death was determined by comparing the average number of surviving cells exposed to 4SP65 versus the average number of surviving sham exposed cells. The average growth inhibitory dose 50% (EC(50)), in micromoles, for each cell line tested are presented in Table 1. It should be noted that the methodology used does not distinguish well between cell killing versus growth arrest of cells, and thus, the EC(50) represents the dose of drug required to induce one or both effects.

Example 2—Unexpected Changes in Drug Anticancer Efficacy

Figure 12:
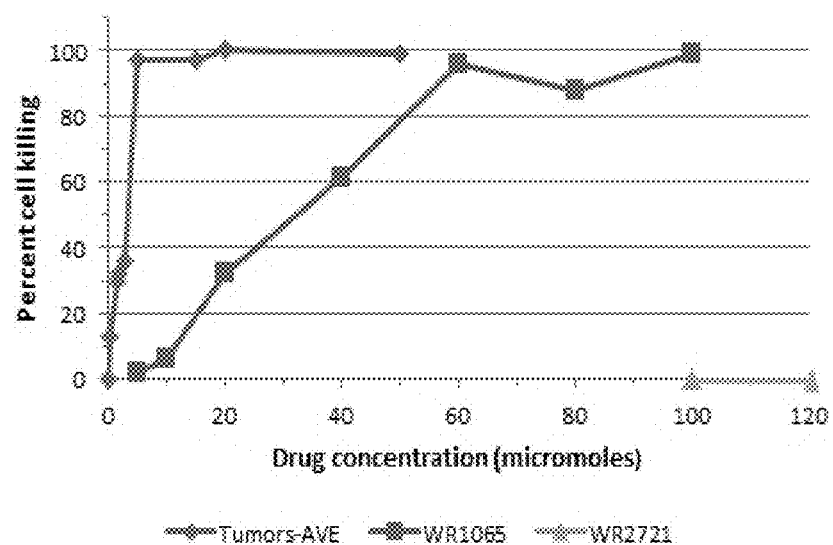
FIG. 12 shows dose response curves for tumor cells (average of all results) exposed to 4SP65, amifostine, or WR1065 alone.

These studies of the anticancer activity of 4SP65 found unexpected drug effects. In brief, these effects were (i) greater anticancer activity for 4SP65 versus amifostine or WR1065 alone than could be predicted based upon the number of WR1065 molecules available per mole of drug, (ii) cytotoxic activity in cell types where amifostine was inactive or where it had a tumor-protective effect, and (iii) a more narrow range of activity across tumor types than seen in the NIH-NCI60 screens for known anticancer agents. FIG. 12 shows average results for all tumors tested (see Table 1), and for amifostine and WR1065 effects in one tumor type (HL60 cells). Results for amifostine and WR1065 in other tumor types were similar to those shown in FIG. 12.

Reported studies found that WR-1065, when delivered as amifostine (WR-2721), had in vitro and/or in vivo anticancer activity against all of the tumors listed in Table 1, with the exception of prostate cancer. What the literature does not show is that substitution of the —PO3 moiety of amifostine with a thiolated 4-arm star PEG molecule increased drug efficacy, when compared on a mole-to-mole basis to the active moiety WR-1065 or to WR-2721. The activity of 4SP65 ranged from 8- to 12-fold greater than that of WR-1065, and 100-fold to several thousand-fold greater than that of amifostine, with differences noted between specific tumor types. On a mole-to-mole basis, each mole of 4-arm star PEG-WR1065 (4SP65) has four molecules of WR1065 for every one molecule of WR-1065 or WR-2721, and as a result, one would expect only a maximum of a 4-fold increase in activity compared to that of WR-1065 or amifostine.

Other reasons that this increased activity could not be anticipated include the following. WR1065 and amifostine have low molecular weights of 134.25 and 214.2 Daltons, respectively. As such, they enter cells primarily through passive diffusion through the cell membrane (Lipinski et al., "Experimental and Computational Approaches to Estimate Solubility and Permeability in Drug Discovery and Development Settings," *Adv. Drug Deliv. Rev.* 46(1-3):3-26 (2001), which is hereby incorporated by reference in its entirety), with WR-1065 having greater facility for passive diffusion than amifostine. Some investigators found evidence that WR-1065 is transported actively into cells via the polyamine transport system (Mitchell et al., "Involvement of the Polyamine Transport System in Cellular Uptake of the Radioprotectants WR-1065 and WR-33278," *Carcinogenesis.* 16(12):3063-8 (1995); Mitchell et al., "Mammalian Cell Polyamine Homeostasis is Altered by the Radioprotector WR1065," *Biochem. J.* 335(Pt 2):329-34 (1998), each of which is hereby incorporated by reference in its entirety) when present at low cell concentrations, but not all investigators agreed with these data (Newton et al., "Transport of Aminothiol Radioprotectors Into Mammalian Cells: Passive Diffusion Versus Mediated Uptake," *Radiat. Res.* 146(2): 206-15 (1996), which is hereby incorporated by reference in its entirety). The drug 4SP65 has a molecular weight of approximately 10,584 Daltons, a size that precludes passive diffusion through cell membranes, and thus, intracellular uptake must occur by other mechanisms such as endocytosis/pinocytosis (Lipinski et al., "Experimental and Computational Approaches to Estimate Solubility and Permeability in Drug Discovery and Development Settings," *Adv. Drug Deliv. Rev.* 46(1-3):3-26 (2001), which is hereby incorporated by reference in its entirety). Since the latter is a slow process compared to passive diffusion or active transport, it is to be expected that the uptake of 4SP65 would be significantly lower than that of WR-1065 or amifostine. Lower uptake results in reduced drug efficacy, not increased drug activity.

The reported literature also does not show that the 4SP65 will have activity in cells where amifostine was inactive or where it had a cytoprotective effect instead of a cytotoxic effect. The activity of amifostine is known to depend, at least in part, upon the levels of expression of cell membrane-bound alkaline phosphatase, but this information alone is not sufficient to be able to predict drug activity (Shen et al., "Binding of the Aminothiol WR-1065 to Transcription Factors Influences Cellular Response to Anticancer Drugs," *J. Pharmacol. Exp. Ther.* 297(3):1067-73 (2001), which is hereby incorporated by reference in its entirety). For example, amifostine is not active in many tumor types, even though the drug is taken up initially from circulation by endothelial cells, which produce abundant amounts of membrane-bound alkaline phosphatase and can metabolize the drug to WR-1065 and pass it on to adjacent tumor cells. Literature reports describe amifostine as having a radioprotective effect upon prostate cancer cells (Quinones et al., "Selective Exclusion by the Polyamine Transporter as a Mechanism for Differential Radioprotection of Amifostine Derivatives," *Clin. Cancer Res.* 8(5):1295-300 (2002), which is hereby incorporated by reference in its entirety), but 4SP65 had a cytotoxic effect against DU-145 cells in vitro. The reasons for these opposite effects cannot be determined from the available literature, and thus, the anticancer efficacy of 4SP65 against cells of a prototypic prostate cancer cell line could not be predicted in advance.

It also should be noted that addition of PEG to a protein, drug, or active moiety of a drug cannot be used as a predictable method for increasing drug efficacy. Such additions or substitutions can result in increased activity, decreased activity, or have no effect on activity (Mehvar, "Modulation of the Pharmacokinetics and Pharmacodynamics of Proteins by Polyethylene Glycol Conjugation," *J. Pharm. Pharm. Sci.* 3(1): 25-36 (2000), which is hereby incorporated by reference in its entirety).

Based upon O'Connor (O'Connor et al., "Characterization of the p53 Tumor Suppressor Pathway in Cell Lines of the National Cancer Institute Anticancer Drug Screen and Correlations With the Growth-Inhibitory Potency of 123 Anticancer Agents," *Cancer Res.* 57(19):4285-300 (1997), which is hereby incorporated by reference in its entirety), the range in EC(50) measurements, from most sensitive to least sensitive tumor cell type, for four commonly used chemotherapeutic agents is about 100-fold. For 4SP65, this range is only about 5-fold. The reasons for this difference are unknown, and cannot be predicted from the available literature.

Example 3—Antiviral Effects of 4-Arm-PEG-WR1065 in Cells Infected with Mouse Coxsackie B Virus (Prophetic)

Mouse cardiomyocytes will be plated at 70 to 80% confluence in growth medium and allowed to plate down and enter the growth cycle for 24 hours. Then, the growth medium will be removed and the cells will be exposed to medium containing dilutions of mouse coxsackie B virus for 30 mins. At the end of this time period, the virus-containing medium will be removed and the cells will be fed with 4-arm-PEG-WR1065-supplemented medium, where the dose of 4-arm-PEG-WR1065 ranges from 0.5 to 20 microM. Plates of control cells will be exposed to medium containing dilutions of coxsackie B virus and then will be referred at 6 hours with unsupplemented growth medium. All plates will be referred with their respective media every three days. At 72 hours, and every three days thereafter, medium will be removed and assayed by RT-PCR for viral replication. Compared to control, virus-infected cells, viral replication is predicted to be reduced by 90% to 99% by 6 days post-exposure. The degree of viral replication is expected to continue to decline for up to 10 days post-exposure

Example 4—Cytotoxic Effect of 4-Arm-PEG-WR1065 (4SP65) Against Bacteria, Yeast, and Fungi (Prophetic)

The antimicrobial activity of 4SP65 will be tested against the bacteria, yeast and fungi described in US Application Publication No. 2008/0027030, titled "Pharmaceutical Compositions Comprising Amifostine and Related Compounds" to Stogniew and Bourthis ("Stogniew and Bourthis"), which is hereby incorporated by reference in its entirety. Experiments as described herein will be performed in which the antimicrobial agent to be tested will be 4SP65 instead of amifostine. The growth inhibitory activity of 4SP65 will be tested alone and also in combination with other drugs. The antimicrobial effects of 4SP65 are predicted to be at least 8- to 12-fold greater than those described for amifostine in Stogniew and Bourthis.

Example 5—Cytoprotective Effects of 4-Arm-PEG-WR1065 in Cells Exposed to Cyclophosphamide TK6 human lymphoblastoid cells in log phase growth were plated in growth medium at 50 to 60% confluence and allowed to proliferate for 24 hours. Then the growth medium was removed and replaced by medium supplemented with one of three types of medium: (i) growth medium supplemented with 1 milliM cyclophosphamide, (ii) growth medium supplemented with 1 milliM cyclophosphamide plus 100 to 400 microM 4-arm-PEG-WR1065, (iii) unsupplemented growth medium (controls). The plates were evaluated 48 and 72 hours later for evidence of cell death. Using the control plates as reference, cell death at 72 hours for the cells exposed to 1 milliM cyclophosphamide was 70% based upon Trypan Blue exclusion, while for the cells exposed to 1 milliM cyclophosphamide plus 100 to 400 microM 4-arm-PEG-WR1065 cells death was approximately 19%.

Example 6—Cytotoxic Effects of 4-Arm-PEG-WR1065 on Normal Human Mammary Epithelial Cells (M99005)

Normal human mammary epithelial cells were grown as described in Example 1, with the exception that the growth medium was as MEBM (purchased from American Type Tissue Culture Collection). When the cells had reach 50 to 60%, the growth medium was removed and medium supplemented with 0 to 300 microM 4SP65 was added to each well containing cells. At 48 hours, the cells were removed by trypsinization stained with Trypan Blue, and counted using a hemocytometer. No inhibition of cell growth was observed at any drug concentration except at the 100 microM exposure level. Cell growth was inhibited by approximately 22% to 40%. Above 100 microM and up to 300 microM no evidence of cell growth inhibition was observed. Thus, the results showed a biphasic curve that did not reach 50% growth inhibition. The finding of a biphasic growth inhibition curve for WR-1065 has been reported previously (Calabro-Jones et al. "The limits to radioprotection of Chinese hamster V79 cells by WR-1065 under aerobic conditions." *Radial Res.* 149: 550-559 (1998), which is hereby incorporated by reference in its entirety).

Example 7—Antiviral Effects of 4-Arm-PEG-WR-1065 Against Zika Virus and/or Other Positive Strand RNA Viruses (Prophetic)

Vero cells or other cells permissive for infection by Zika virus will be grown as described above (see Example 1) until 50 to 70% confluent. Then the cells will be treated with 4SP65 for up to 48 hours at drug levels that range from 0 to 100 microM. At the end of this exposure period, growth medium supplemented with 4SP65 will be removed and replaced with growth medium containing differing infectious units of Zika virus. Evidence of virus-induced cytotoxic effects will be assessed at multiple time points post-virus exposure to determine the ability of 4SP65 to reduce or prevent viral infection. In a similar experiment, cells will be infected with the virus for 30 minutes, and then exposed to 4SP65 at doses ranging from 0 to 100 microM and for time periods that range from 0 to 48 hrs. The antiviral therapeutic efficacy of 4SP65 will be determined and is expected to fall within the range of 0.1 to 13 microM. The same experimental design will be used to test the antiviral efficacy of 4SP65 against other viral pathogens of concern to humans or animals. Antiviral efficacy in the range of 0.1 to 13 microM is expected to be observed for all experiments.

Example 8—Preparation of Compound 7

Step 1. Boc Protection

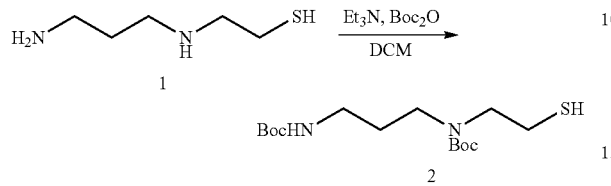

Step 2. Coupling with Disulfide

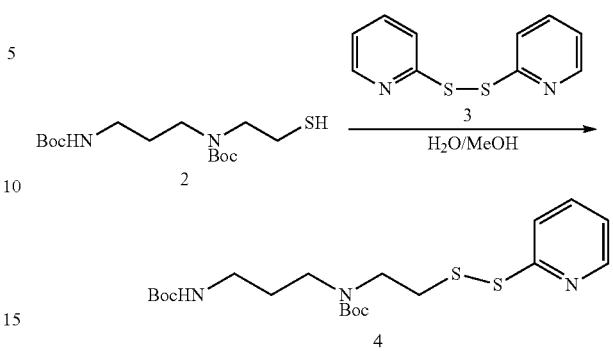

Substrate 1 (as dihydrochloride salt, 1.21 mmol) was dissolved in anhydrous dichloromethane (5 ml). Triethyl amine (6 eq.) and boc anhydride (2.1 eq) were added and the reaction was stirred at ambient temperature overnight under a positive nitrogen atmosphere. The next day, the reaction was diluted with dichloromethane and washed with brine. The organic layer was dried over magnesium sulfate and concentrated in vacuo to give compound 2 as a clear oil in 85% yield. The compound was used in the next step without purification.

Substrate 2 (1.03 mmol) was dissolved in 1/1 water/methanol (10 ml) and disulfide 3 (2 eq.) was added. The reaction was stirred at ambient temperature under nitrogen overnight. Next day the reaction was concentrated in vacuo and diluted with dichloromethane. It was washed with brine and dried over magnesium sulfate. The product 4 was purified by column chromatography with silica gel and hexane/ethyl acetate gradient. The product was isolated in 46% yield.

Step 3. Coupling with Star Polymer

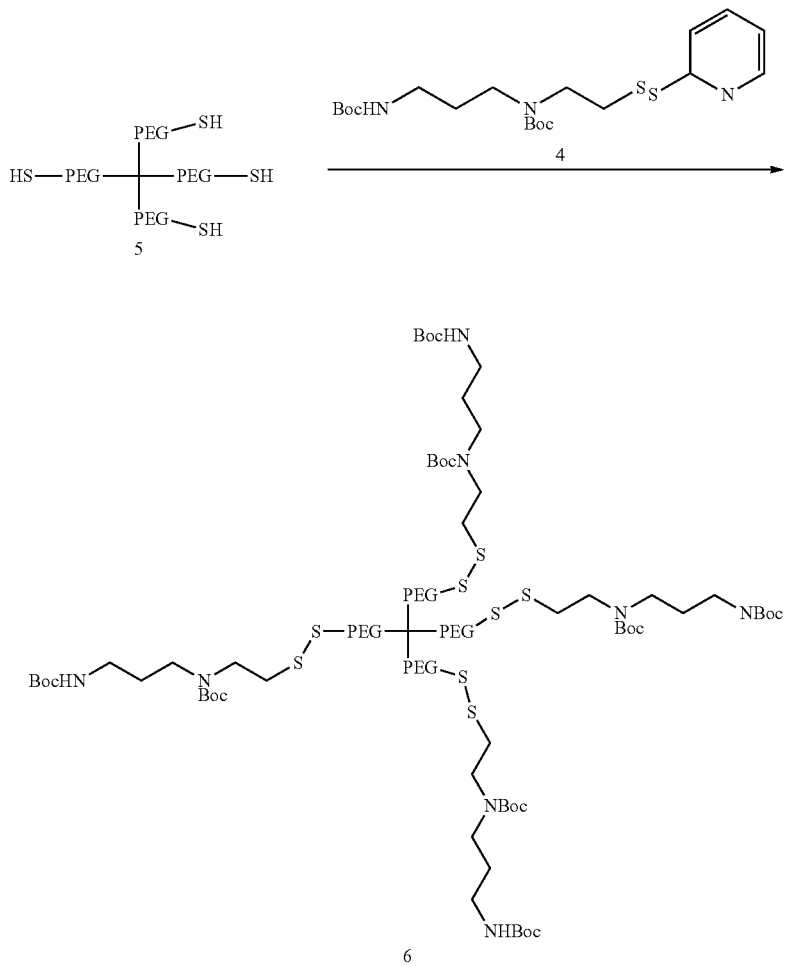

To a solution of star polymer 5 (0.75 g, average molecular weight 10,000) in PBS (8 ml, pH 7.4) was added a solution of disulfide 5 (0.45 mmol) in ethanol (2 ml). The reaction was stirred for 4 hours at ambient temperature and then lyophilized overnight. The crude was dissolved in water (4 ml) and DMSO (2 ml) and was dialyzed against water for 48 hours with four water changes. Afterwards, the solution was lyophilized and 814 mg of conjugate 6 was isolated.

Step 4. Deprotection to Give Conjugate 7

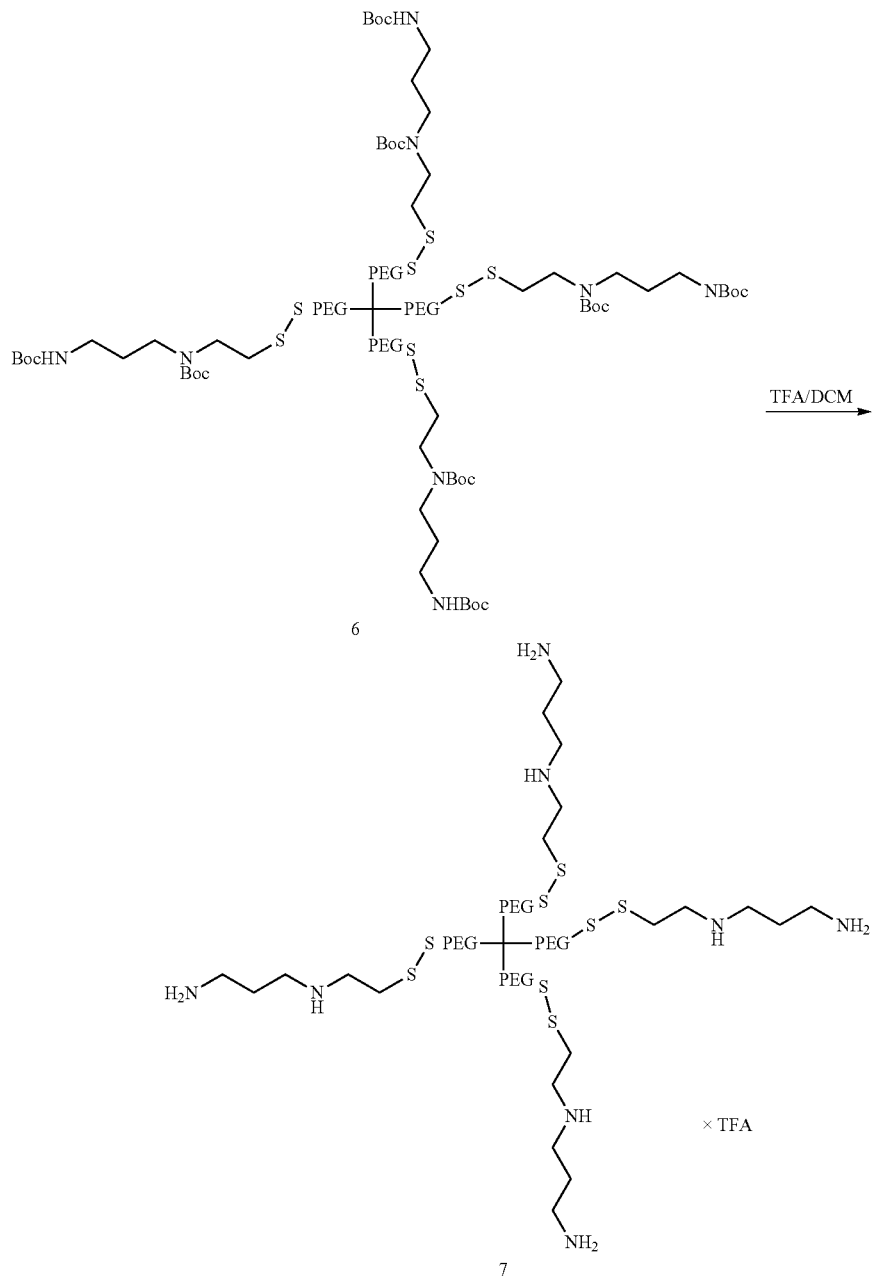

Conjugate 6 (814 mg) was treated with 1/1 TFA/dichloromethane (5 ml) for 30 min. The solvent was removed in vacuo and the residue was dried on a vacuum pump overnight. Next day, the residue was washed with ethyl ether (twice) and further dried on a vacuum pump overnight. 750 mg of conjugate 7 was obtained. MALDI analysis indicated an average mass of 10,531.95, which suggested incorporation of four WR1065 units on average.

Although certain embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a subject in need of aminothiol therapy, the method comprising:

administering to the subject an aminothiol-conjugate having the formula:

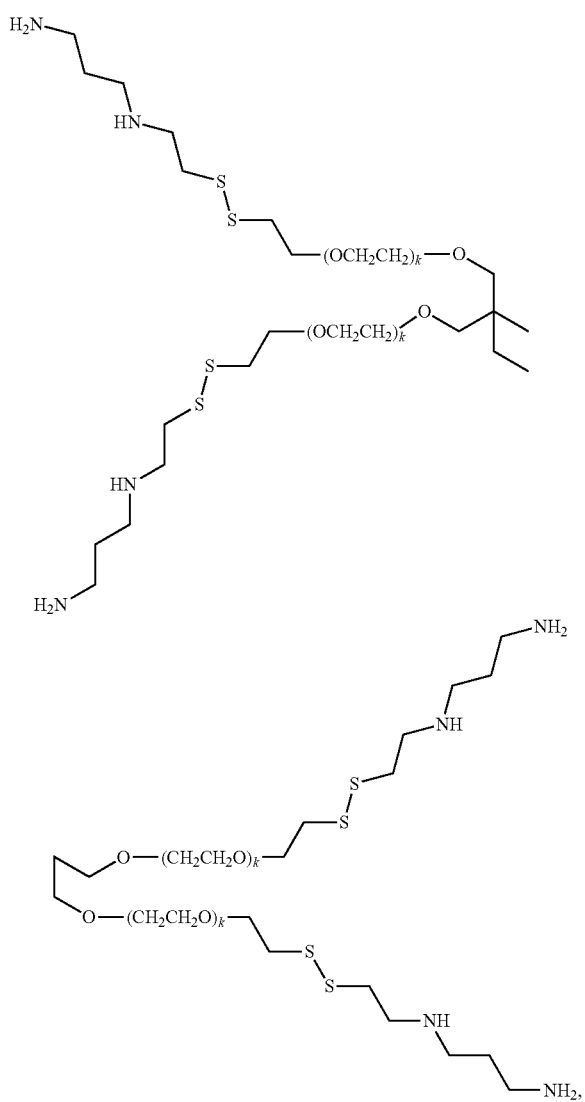

wherein k is independently 1 to 2500, or a pharmaceutically acceptable salt thereof; or a pharmaceutical composition comprising said aminothiol-conjugate or pharmaceutically acceptable salt thereof.

2. The method according to claim 1, wherein the subject is in need of treatment with an antiviral agent, a chemoprotectant, a cytoprotectant, a radioprotectant, an anti-fibrotic agent, an anti-tumor agent, or an antioxidant.

3. The method according to claim 1, wherein the subject is infected with a virus and the aminothiol-conjugate, pharmaceutically acceptable salt thereof, or pharmaceutical composition is administered under conditions effective to treat the virus.

4. The method of claim 3, wherein the subject is infected with HIV, orthomyxovirus, influenza virus, or adenovirus.

5. The method of claim 4, wherein the influenza virus is a type selected from the group consisting of H1N1 and H3N2.

6. The method of claim 4, wherein the adenovirus is a species selected from the group consisting of B, C, and E.

7. The method of claim 3, wherein the subject is not infected with HIV.

8. The method according to claim 1, wherein the subject is suffering from a neoplastic condition and the aminothiol-conjugate, pharmaceutically acceptable salt thereof, or pharmaceutical composition is administered under conditions effective to treat the neoplastic condition.

9. The method according to claim 8, wherein the neoplastic condition is selected from the group consisting of breast, ovary, cervix, colon, lung, skin, lymphoreticular tumors, and combinations thereof.

10. The method according to claim 9, wherein the neoplastic condition is malignant melanoma.

11. The method according to claim 8, wherein the neoplastic condition is a myelodysplastic condition.

12. The method according to claim 1, wherein the subject receives radiation therapy, chemotherapy, or a combination thereof and the aminothiol-conjugate, pharmaceutically acceptable salt thereof, or pharmaceutical composition is administered under conditions effective to reduce or decrease the adverse or undesirable side-effects of the radiation therapy, chemotherapy, or combination thereof.

13. The method according to claim 1, wherein the subject is in need of anti-microbial therapy and the aminothiol-conjugate, pharmaceutically acceptable salt thereof, or pharmaceutical is administered under conditions effective to kill one or more pathogenic microorganisms in the subject.

14. The method according to claim 13, wherein the microorganism is selected from the group consisting of a bacterium, a yeast, a fungus, or a parasite.

15. The method according to claim 14, wherein the parasite is an intracellular parasite.

16. The method according to claim 14, wherein the parasite is an extracellular parasite.

17. The method according to claim 1, wherein the subject is a mammal.

18. The method according to claim 17, wherein the mammal is a human.

* * * * *

UNITED STATES PATENT AND TRADEMARK OFFICE
CERTIFICATE OF CORRECTION

| | | |
|---|---|---|
| PATENT NO. | : 11,554,174 B2 | Page 1 of 1 |
| APPLICATION NO. | : 16/988239 | |
| DATED | : January 17, 2023 | |
| INVENTOR(S) | : Walker et al. | |

It is certified that error appears in the above-identified patent and that said Letters Patent is hereby corrected as shown below:

In the Claims

In Claim 1, Column 69, Lines 1–42, please delete the following compounds:

" 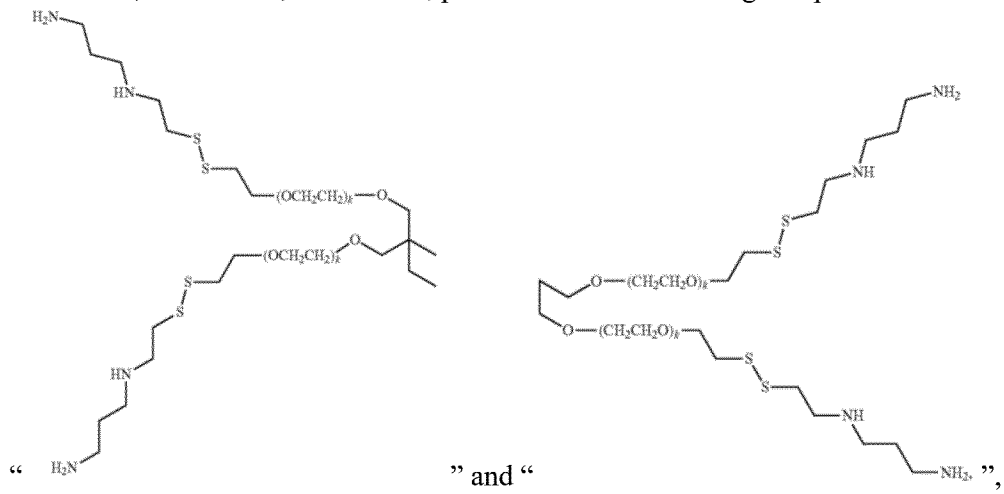 " and " 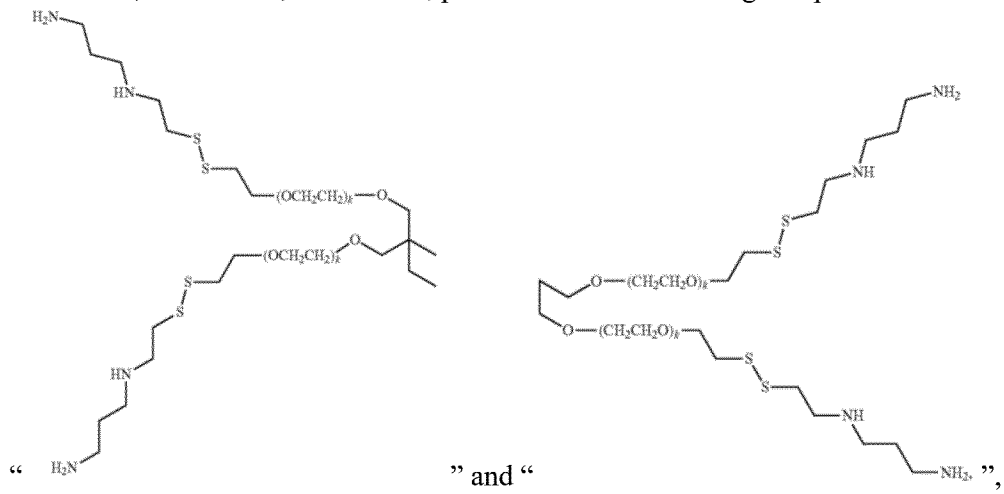 ",

And insert in their place the following compound:

-- 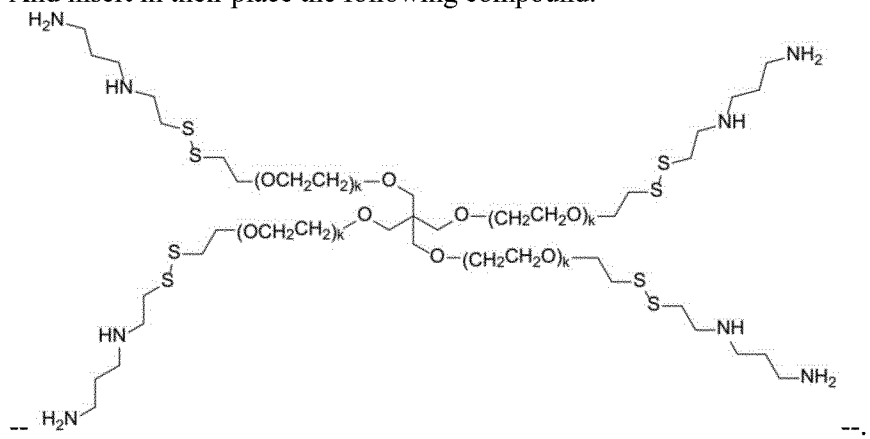 --.

Signed and Sealed this
Thirtieth Day of May, 2023

Katherine Kelly Vidal
*Director of the United States Patent and Trademark Office*